(12) United States Patent
Glenn et al.

(10) Patent No.: US 7,378,097 B2
(45) Date of Patent: *May 27, 2008

(54) USE OF PENETRATION ENHANCERS AND BARRIER DISRUPTION METHODS TO ENHANCE THE IMMUNE RESPONSE OF ANTIGEN AND ADJUVANT

(75) Inventors: Gregory M. Glenn, Cabin John, MD (US); Carl R. Alving, Bethesda, MD (US)

(73) Assignee: The United States of America as represented by the Secretary of the Army, Washington, DC (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/790,715

(22) Filed: Mar. 3, 2004

(65) Prior Publication Data

US 2008/0063696 A1    Mar. 13, 2008

Related U.S. Application Data

(63) Continuation of application No. 09/257,188, filed on Feb. 25, 1999, now Pat. No. 6,797,276, and a continuation-in-part of application No. PCT/US97/21324, filed on Nov. 14, 1997, now abandoned, and a continuation-in-part of application No. 08/896,085, filed on Jul. 17, 1997, now Pat. No. 5,980,898, which is a continuation-in-part of application No. 08/749,164, filed on Nov. 14, 1996, now Pat. No. 5,910,306.

(60) Provisional application No. 60/086,251, filed on May 21, 1998, provisional application No. 60/075,856, filed on Feb. 25, 1998, provisional application No. 60/075,850, filed on Feb. 25, 1998.

(51) Int. Cl.
*A61K 45/00* (2006.01)

(52) U.S. Cl. .............................. 424/184.1; 424/234.1; 424/447; 424/449

(58) Field of Classification Search ............ 424/278.1, 424/184.1
See application file for complete search history.

(56) References Cited

U.S. PATENT DOCUMENTS

| | | | |
|---|---|---|---|
| 3,837,340 A | 9/1974 | Counter |
| 3,948,263 A | 4/1976 | Drake |
| 3,964,482 A | 6/1976 | Gerstel |
| 3,982,536 A | 9/1976 | Krogseng |
| 4,196,191 A | 4/1980 | Almeida |
| 4,220,584 A | 9/1980 | Limjuco |
| 4,235,871 A | 11/1980 | Papahadjopoulos |
| 4,285,931 A | 8/1981 | Limjuco |
| 4,394,448 A | 7/1983 | Szoka |
| 4,411,888 A | 10/1983 | Klipstein |
| 4,455,142 A | 6/1984 | Martins |
| 4,484,923 A | 11/1984 | Amkraut |
| 4,497,796 A | 2/1985 | Salser |
| 4,587,044 A | 5/1986 | Miller |
| 4,692,462 A | 9/1987 | Banerjee |
| 4,725,271 A | 2/1988 | Korol |
| 4,732,892 A | 3/1988 | Sarpotdar |
| 4,743,588 A | 5/1988 | Mirejovsky |
| 4,761,372 A | 8/1988 | Maas |
| 4,764,381 A | 8/1988 | Bodor |
| 4,775,361 A | 10/1988 | Jacques |
| 4,783,450 A | 11/1988 | Fawzi |
| 4,810,499 A | 3/1989 | Nuwayser |
| 4,834,985 A | 5/1989 | Elger |
| 4,876,278 A | 10/1989 | Taylor |
| 4,877,612 A | 10/1989 | Berger |
| 4,892,737 A | 1/1990 | Bodor |
| 4,908,389 A | 3/1990 | Mahjour |
| 4,917,688 A | 4/1990 | Nelson |
| 4,917,895 A | 4/1990 | Lee |
| 4,921,757 A | 5/1990 | Wheatley |
| 4,929,442 A | 5/1990 | Powell |
| 4,946,853 A | 8/1990 | Bannon |
| 4,956,171 A | 9/1990 | Chang |
| 4,960,771 A | 10/1990 | Rajadhyaksha |
| 4,970,206 A | 11/1990 | Alexander |
| 5,003,987 A | 4/1991 | Grinwald |
| 5,008,050 A | 4/1991 | Cullis |
| 5,008,111 A | 4/1991 | Bodor |

(Continued)

FOREIGN PATENT DOCUMENTS

AU        47099/89        6/1990

(Continued)

OTHER PUBLICATIONS

Kuby, 2000, Immunology, 4th ed. p. 47-53.*

(Continued)

*Primary Examiner*—Christina Chan
*Assistant Examiner*—Yunsoo Kim
(74) *Attorney, Agent, or Firm*—Morgan, Lewis & Bockius LLP

(57) ABSTRACT

A transcutaneous immunization system where the topical application of an adjuvant and an antigen or nucleic acid encoding for an antigen, to intact skin induces a systemic or mucosol antibody response. The immune response so elicited can be enhanced by physical or chemical skin penetration enhancement.

108 Claims, 5 Drawing Sheets

U.S. PATENT DOCUMENTS

| | | |
|---|---|---|
| 5,023,252 A | 6/1991 | Hsieh |
| 5,028,435 A | 7/1991 | Katz |
| 5,030,629 A | 7/1991 | Rajadhyaksha |
| 5,032,402 A | 7/1991 | Digenis |
| 5,041,439 A | 8/1991 | Kasting |
| 5,045,317 A | 9/1991 | Chess |
| 5,049,386 A | 9/1991 | Eppstein |
| 5,049,387 A | 9/1991 | Amkraut |
| 5,059,189 A | 10/1991 | Cilento |
| 5,059,421 A | 10/1991 | Loughrey |
| 5,069,904 A | 12/1991 | Masterson |
| 5,082,866 A | 1/1992 | Wong |
| 5,108,921 A | 4/1992 | Low |
| 5,133,970 A | 7/1992 | Petereit |
| 5,142,044 A | 8/1992 | Minaskanian |
| 5,162,315 A | 11/1992 | Rajadhyaksha |
| 5,164,406 A | 11/1992 | Helman |
| 5,166,320 A | 11/1992 | Wu |
| 5,169,637 A | 12/1992 | Lenk |
| 5,182,109 A | 1/1993 | Tamura |
| 5,196,410 A | 3/1993 | Francoeur |
| 5,200,393 A | 4/1993 | Weiner |
| 5,204,339 A | 4/1993 | Minaskanian |
| 5,215,520 A | 6/1993 | Shroot |
| 5,225,182 A | 7/1993 | Sharma |
| 5,232,935 A | 8/1993 | Colas |
| 5,234,959 A | 8/1993 | Minaskanian |
| 5,238,944 A | 8/1993 | Wick |
| 5,240,846 A | 8/1993 | Collins |
| 5,250,023 A | 10/1993 | Lee |
| 5,252,334 A | 10/1993 | Chiang |
| 5,256,422 A | 10/1993 | Albert |
| 5,260,066 A | 11/1993 | Wood |
| 5,270,346 A | 12/1993 | Minaskanian |
| 5,279,544 A | 1/1994 | Gross |
| 5,308,835 A | 5/1994 | Clements |
| 5,326,566 A | 7/1994 | Parab |
| 5,326,790 A | 7/1994 | Thornfeldt |
| 5,328,470 A | 7/1994 | Nabel |
| 5,332,576 A | 7/1994 | Mantelle |
| 5,332,577 A | 7/1994 | Gertner |
| 5,340,588 A | 8/1994 | Domb |
| 5,352,449 A | 10/1994 | Beltz |
| 5,399,346 A | 3/1995 | Anderson |
| 5,411,738 A | 5/1995 | Hind |
| 5,428,132 A | 6/1995 | Hirsch |
| 5,445,611 A | 8/1995 | Eppstein . |
| 5,458,140 A | 10/1995 | Eppstein |
| 5,462,743 A | 10/1995 | Turner |
| 5,464,386 A | 11/1995 | Hofmann |
| 5,472,946 A | 12/1995 | Peck |
| 5,482,965 A | 1/1996 | Rajadhyaksha |
| 5,492,698 A | 2/1996 | Von Kleinsorgen |
| 5,505,956 A | 4/1996 | Kim |
| 5,505,958 A | 4/1996 | Bello |
| 5,533,995 A | 7/1996 | Corish |
| 5,534,260 A | 7/1996 | Petersen |
| 5,536,263 A | 7/1996 | Rolf |
| 5,540,931 A | 7/1996 | Hewitt |
| 5,547,932 A | 8/1996 | Curiel |
| 5,573,778 A | 11/1996 | Therriault |
| 5,578,475 A | 11/1996 | Jessee |
| 5,580,859 A | 12/1996 | Felgner |
| 5,589,466 A | 12/1996 | Felgner |
| 5,593,972 A | 1/1997 | Weiner |
| 5,601,827 A | 2/1997 | Collier |
| 5,607,691 A | 3/1997 | Hale |
| 5,612,382 A | 3/1997 | Fike |
| 5,614,212 A | 3/1997 | D'Angelo |
| 5,614,503 A | 3/1997 | Chaudhary |
| 5,620,896 A | 4/1997 | Hermann |
| 5,626,866 A | 5/1997 | Ebert |
| 5,643,578 A | 7/1997 | Robinson |
| 5,658,587 A | 8/1997 | Santus |
| 5,661,025 A | 8/1997 | Szoka |
| 5,661,130 A | 8/1997 | Meezan |
| 5,674,503 A | 10/1997 | Olafson |
| 5,676,954 A | 10/1997 | Brigham |
| 5,679,647 A | 10/1997 | Carson |
| 5,686,100 A | 11/1997 | Wille |
| 5,688,523 A | 11/1997 | Garbe |
| 5,693,024 A | 12/1997 | Flower |
| 5,693,622 A | 12/1997 | Wolff |
| 5,695,991 A | 12/1997 | Lindholm |
| 5,697,901 A | 12/1997 | Eriksson |
| 5,698,416 A | 12/1997 | Wolf |
| 5,703,057 A | 12/1997 | Johnston |
| 5,705,151 A | 1/1998 | Dow |
| 5,718,914 A | 2/1998 | Foldvari |
| 5,720,948 A | 2/1998 | Brucks |
| 5,722,397 A | 3/1998 | Eppstein |
| 5,723,114 A | 3/1998 | Thornfeldt |
| 5,731,303 A | 3/1998 | Hsieh |
| 5,733,572 A | 3/1998 | Unger |
| 5,733,762 A | 3/1998 | Midoux |
| 5,736,154 A | 4/1998 | Fuisz |
| 5,736,392 A | 4/1998 | Hawley-Nelson |
| 5,736,524 A | 4/1998 | Content |
| 5,738,647 A | 4/1998 | Bernhard |
| 5,739,118 A | 4/1998 | Carrano |
| 5,741,510 A | 4/1998 | Rolf |
| 5,756,117 A | 5/1998 | D'Angelo |
| 5,760,096 A | 6/1998 | Thornfeldt |
| 5,766,899 A | 6/1998 | Kuo |
| 5,770,580 A | 6/1998 | Ledley |
| 5,773,022 A | 6/1998 | Nyqvist-Mayer |
| 5,780,050 A | 7/1998 | Jain |
| 5,783,567 A | 7/1998 | Hedley |
| 5,789,230 A | 8/1998 | Cotton |
| 5,804,214 A | 9/1998 | Wong |
| 5,804,566 A | 9/1998 | Carson |
| 5,811,406 A | 9/1998 | Szoka |
| 5,814,599 A | 9/1998 | Mitragotri |
| 5,814,617 A | 9/1998 | Hoffman |
| 5,824,538 A | 10/1998 | Branstrom |
| 5,827,703 A | 10/1998 | Debs |
| 5,827,705 A | 10/1998 | Dean |
| 5,830,876 A | 11/1998 | Weiner |
| 5,830,877 A | 11/1998 | Carson |
| 5,834,010 A | 11/1998 | Quan |
| 5,837,289 A | 11/1998 | Grasela |
| 5,837,533 A | 11/1998 | Boutin |
| 5,840,059 A | 11/1998 | March |
| 5,843,913 A | 12/1998 | Li |
| 5,844,107 A | 12/1998 | Hanson |
| 5,846,540 A | 12/1998 | Restifo |
| 5,846,949 A | 12/1998 | Wagner |
| 5,849,719 A | 12/1998 | Carson |
| 5,853,751 A | 12/1998 | Masiz |
| 5,856,187 A | 1/1999 | Restifo |
| 5,858,784 A | 1/1999 | Debs |
| 5,866,553 A | 2/1999 | Donnelly |
| 5,877,159 A | 3/1999 | Powell |
| 5,877,302 A | 3/1999 | Hanson |
| 5,879,326 A | 3/1999 | Godshall |
| 5,885,211 A | 3/1999 | Eppstein |
| 5,885,971 A | 3/1999 | German |
| 5,910,306 A | 6/1999 | Alving |
| 5,910,488 A | 6/1999 | Nabel |
| 5,914,114 A | 6/1999 | Cassels |
| 5,916,879 A | 6/1999 | Webster |
| 5,935,838 A | 8/1999 | Askeloef |
| 5,961,979 A | 10/1999 | Srivastava |
| 5,980,898 A | 11/1999 | Glenn |

| | | |
|---|---|---|
| 5,985,847 A | 11/1999 | Carson |
| 5,993,849 A | 11/1999 | Assmus |
| 5,993,852 A | 11/1999 | Foldvari |
| 6,019,982 A | 2/2000 | Clements |
| 6,022,316 A | 2/2000 | Eppstein |
| 6,033,673 A | 3/2000 | Clements |
| 6,033,684 A | 3/2000 | Norcia |
| 6,039,969 A | 3/2000 | Tomai |
| 6,063,399 A | 5/2000 | Assmus |
| 6,087,341 A | 7/2000 | Khavari |
| 6,090,790 A | 7/2000 | Eriksson |
| 6,142,939 A | 11/2000 | Eppstein |
| 6,149,919 A | 11/2000 | Domenighini |
| 6,165,458 A | 12/2000 | Foldvari |
| 6,165,500 A | 12/2000 | Cevc |
| 6,173,202 B1 | 1/2001 | Eppstein |
| 6,180,136 B1 | 1/2001 | Larson |
| 6,183,434 B1 | 2/2001 | Eppstein |
| 6,190,367 B1 | 2/2001 | Hall |
| 6,190,689 B1 | 2/2001 | Hoffmann |
| 6,207,184 B1 | 3/2001 | Ikeda |
| 6,210,672 B1 | 4/2001 | Cowing |
| 6,256,533 B1 | 7/2001 | Yuzhakov |
| 6,290,991 B1 | 9/2001 | Roser |
| 6,312,612 B1 | 11/2001 | Sherman |
| 6,331,266 B1 | 12/2001 | Powell |
| 6,331,310 B1 | 12/2001 | Roser |
| 6,334,856 B1 | 1/2002 | Allen |
| 6,348,212 B2 | 2/2002 | Hymes |
| 6,348,450 B1 | 2/2002 | Tang |
| 6,365,178 B1 | 4/2002 | Venkateshwaran |
| 6,379,324 B1 | 4/2002 | Gartstein |
| 6,406,705 B1 | 6/2002 | Davis |
| 6,413,523 B1 | 7/2002 | Clements |
| 6,440,096 B1 | 8/2002 | Lastovich |
| 6,451,240 B1 | 9/2002 | Sherman |
| 6,454,755 B1 | 9/2002 | Godshall |
| 6,471,903 B2 | 10/2002 | Sherman |
| 6,797,276 B1 | 9/2004 | Glenn |

FOREIGN PATENT DOCUMENTS

| | | |
|---|---|---|
| EP | 0 891 770 | 1/1999 |
| WO | WO 92/03122 | 3/1992 |
| WO | WO 94/21230 | 9/1994 |
| WO | WO 95/17211 | 6/1995 |
| WO | WO 96/06627 | 3/1996 |
| WO | WO 96/19976 | 4/1996 |
| WO | WO 96/14074 | 5/1996 |
| WO | WO 96/14855 | 5/1996 |
| WO | WO 96/25190 | 8/1996 |
| WO | WO 96/37256 | 11/1996 |
| WO | WO 97/04832 | 2/1997 |
| WO | WO 97/07734 | 3/1997 |
| WO | WO 97/24447 | 7/1997 |
| WO | WO 97/31119 | 8/1997 |
| WO | WO 97/35957 | 10/1997 |
| WO | WO 98/00193 | 1/1998 |
| WO | WO 98/01538 | 1/1998 |
| WO | WO 98/10750 | 3/1998 |
| WO | WO 98/20734 | 5/1998 |
| WO | WO 98/29134 | 7/1998 |
| WO | WO 98/42375 | 10/1998 |
| WO | WO 98/46208 | 10/1998 |
| WO | WO 99/04009 | 1/1999 |
| WO | WO 99/08689 | 2/1999 |
| WO | WO 99/08713 | 2/1999 |
| WO | WO 99/13915 | 3/1999 |
| WO | WO 99/26662 | 6/1999 |
| WO | WO 99/41366 | 8/1999 |
| WO | WO 99/43350 | 9/1999 |
| WO | WO 99/47164 | 9/1999 |
| WO | WO 99/47165 | 9/1999 |
| WO | WO 99/47167 | 9/1999 |
| WO | WO 99/53960 | 10/1999 |
| WO | WO 99/60167 | 11/1999 |
| WO | WO 99/61078 | 12/1999 |
| WO | WO 99/62537 | 12/1999 |
| WO | WO 00/33812 | 6/2000 |
| WO | WO 00/44349 | 8/2000 |
| WO | WO 00/61184 | 10/2000 |
| WO | WO 00/74714 | 12/2000 |
| WO | WO 00/74763 | 12/2000 |
| WO | WO 00/74763 A3 | 12/2000 |
| WO | WO 00/74766 | 12/2000 |
| WO | WO 01/34185 | 5/2001 |
| WO | WO 01/90758 | 11/2001 |
| WO | WO 02/02179 | 1/2002 |
| WO | WO 02/05889 | 1/2002 |
| WO | WO 02/07813 | 1/2002 |
| WO | WO 02/64162 | 8/2002 |
| WO | WO 02/64193 | 8/2002 |
| WO | WO 02/74244 | 9/2002 |

OTHER PUBLICATIONS

Allison "Hydrogen bonding between sugar and protein is responsible for inhibition of dehydration-induced protein unfolding" Arch Biochem Biophys 365 (1999) 289-298.

Allison "Optimization of storage stability of lyophilized actin using combinations of disaccharides and dextran" J Pharm Sci 89 (2000) 199-214.

Andya "The effect of formulation excipients on protein stability and aerosol performance of spray-dried powders of a recombinant humanized anti-IgE monoclonal antibody" Pharm Res 16 (1999) 350-358.

Arakawa "Protein-solvent interactions in pharmaceutical formulations" Pharma Res 8 (1991) 285-291.

Arany "Correlation between pretreatment levels of interferon response genes and clinical responses to an immune response modifier (imiquimod) in genital warts" Antimicrob Agents Chemother 44 (2000) 1869-1873.

Alving "Effectiveness of liposomes as potential carriers of vaccines: Applications to cholera toxin and human malaria sporozoite antigen" Vaccine 4 (1986) 166-172.

Alving "Liposomes as carriers of antigens and adjuvants" J Immunol Methods 140 (1991) 1-13.

Alving "Lipopolysaccharide, lipid A, and liposomes containing lipid A as immunologic adjuvants" Immunobioly 187 (1993) 430-446.

Alving "Novel adjuvant strategies for experimental malaria and AIDS vaccines" Ann NY Acad Sci 690 (1993) 265-275.

Alving "The preparation and use of liposomes in immunological studies" in: *Liposome Technology*, vol. 3, CRC Press (1993) pp. 317-343.

Alving "Cytotoxic T lymphocytes induced by liposomal antigens: Mechanisms of immunological presentation" AIDS Res Hum Retroviruses 10 suppl 2 (1994) S91-S94.

Alving "Liposomes as carriers of peptide antigens: induction of antibodies and cytotoxic T lymphocytes to conjugated and unconjugated peptides" Immunol Rev 145 (1995) 5-31.

Becker "Mechanism in allergic contact dermatitis" Exp Dermatol 2 (1993) 63-69.

Birch "Trehaloses" Adv Carb Chem Biochem 18 (1963) 201-2225.

Blauvelt "Human Langerhans cells express E-cadherin" J Invest Dermatol 104 (1995) 293-296.

Bos "The 500 dalton rule for the skin penetration of chemical compounds and drugs" Exp Dermatol 9 (2000) 165-169.

Bovsun "DNA vaccine rubbed on skin provokes immune response" Biotechnol Newswatch (Sep. 20, 1999) p. 4.

Bowen "Cholera toxin acts as a potent adjuvant for the induction of cytotoxic T-lymphocyte responses with non-replicating antigens" Immunol 81 (1994) 338-342.

Buates "Treatment of experimental Leishmaniasis with the immunomodulators imiquimod and S-28463: Efficacy and mode of action" J Infect Dis 179 (1999) 1485-1494.

Chen "Induction of systemic immune responses in sheep by topical application of cholera toxin to skin" Vet Immunol Immunopathol 77 (2000) 191-199.

Chin "Antibody response against *Pseudomonas aeruginosa* membrane proteins in experimentally infected sheep" Vet Microbiol 43 (1995) 21-32.

Chin "Manipulating systemic and mucosal immune responses with skin-deliverable adjuvants" J Biotechnol 44 (1996) 13-19.

Condon "DNA-based immunization by in vivo transfection of dendritic cells" Nature Med 2 (1996) 1122-1128.

Costantino "Effect of excipients on the stability and structure of lyophilized recombinant human growth hormone" J Pharm Sci 87 (1998) 1412-1420.

Craig "Cutaneous responses to cholera skin toxin in man. I. Responses in unimmunized American males" J Infect Dis 125 (1972) 203-215.

De Haan "Liposomes as an immunoadjuvant system for stimulation of mucosal and systemic antibody responses against inactivated measles virus administered intranasally to mice" Vaccine 13 (1995) 1320-1324.

Egbaria "Liposomes as topical drug delivery system" Adv Drug Delivery Rev 5 (1990) 287-300.

Enk "An essential role for Langerhans cell-derived IL-1 beta in the initiation of primary immune responses in skin" J Immunol 151 (1993) 2390-2398.

Fan "Immunization via hair follicles by topical application of naked DNA to normal skin" Nature Biotechnol 17 (1999) 870-872.

Fleisher "Topical delivery of growth hormone releasing peptide using liposomal systems: An in vitro study using hairless mouse skin" Life Sci 57 (1995) 1293-1297.

Frank "Long-term stabilization of biologicals" Bio/Technology 12 (1994) 253-256.

Gekko "Mechanism of protein stabilization by glycerol: Preferential hydration in glycerol-water mixtures" Biochemistry 20 (1981) 4667-4676.

Glenn "Murine IgG subclass antibodies to antigens incorporated in liposomes containing lipid A" Immunol Lett 47 (1995) 73-78.

Glenn "Skin immunization made possible by cholera toxin" Nature 391 (1998) 851.

Glenn "Transcutaneous immunization with cholera toxin protects mice against lethal mucosal toxin challenge" J Immunol 161 (1998) 3211-3214.

Glenn "Transcutaneous immunization with bacterial ADP-ribosylating exotoxins as antigens and adjuvants" Infect Immun 67 (1999) 1100-1106.

Glenn "Transcutaneous immunisation" Exp Opin Invest Drugs 8 (1999) 797-805.

Glenn "Transcutaneous immunization" In: *The Jordan Report 2000*, NIAID, pp. 91-93.

Glenn "Transcutaneous immunization: A human vaccine delivery strategy using a patch" Nature Med 6 (2000) 1403-1406.

Glenn "Transcutaneous immunization" In: *Vaccine Adjuvants*, Humana Press (Apr. 2000) pp. 315-326.

Glenn "Transcutaneous immunization" In: *New Vaccine Technologies*, Landes Biosciences (Jun. 2001) pp. 292-304.

Goodnow "Chance encounters and organized rendezvous" Immunol Rev 156 (1997) 5-10.

Gupta "Adjuvants for human vaccines—current status, problems and future prospects" Vaccine 13 (1995) 1263-1276.

Hammond "Transcutaneous immunization of domestic animals: Opportunities and challenges" Adv Drug Delivery Rev 43 (2000) 45-55.

Hammond "Transcutaneous immunization: T cell responses and boosting of existing immunity" Vaccine 19 (2001) 2701-2707.

Hanson "Introduction to formulation of protein pharmaceuticals" In: *Stability of Protein Pharmaceuticals*, Plenum (1992) pp. 209-233.

Hoelzle "Increased accumulation of trehalose in rhizobia cultured under 1% oxygen" Appl Environ Microbiol 56 (1990) 3213-3215.

Hsiung *Diagnostic Virology* 3rd Ed., Yale Univ. Press (1982) pp. 29-34.

Iizuka "Two simple methods for the evaluation of topically active anti-inflammatory steroidal ointments" Agents Actions 11 (1981) 254-259.

Izutsu "Increased stabilizing effects of amphiphilic excipients on freeze-drying of lactate dehydrogenase (LDH) by dispersion into sugar matrices" Pharm Res 12 (1995) 838-843.

Johnson "Vaccination onto bare skin" Nature 388 (1997) 729-730.

Kahan "Immunosuppressive therapy" Current Opin Immunol 4 (1992) 553-560.

Knop "Cellular and molecular mechanisms in the induction phase of contact sensitivity" Intl Arch Allergy Immunol 107 (1995) 231-232.

Korting "Topical liposome drugs to come: what the patent literature tells us" J Am Acad Dermatol 25 (1991) 1068-1071.

Korting "Interaction of liposomes with human epidermis reconstructed in vitro" Br J Dermatol 132 (1995) 571-579.

Kosecka "Pertussis toxin stimulates hypersensitivity and enhances nerve-mediated antigen uptake in rat intestines" Am J Physiol 267 (1994) G745-G752.

Lane "In vitro-evaluation of human lymphocyte function" In: *Handbook of Experimental Immunology* 4th Ed., vol. 2, Blackwell (1986) pp. 66.5-66.7.

Luo "Synthetic DNA delivery systems" Nature Biotechnol 18 (2000) 33-37.

Mahmoud "Parasitic protozoa and helminths: Biological and immunological challenges" Science 246 (1989) 1015-1022.

Marinaro "Mucosal effect of cholera toxin in mice results from induction of T helper 2 (Th2) cells and IL-4" J Immunol 155 (1995) 4621-4629.

Mengiardi "Virosomes as carriers for combined vaccines" Vaccine 13 (1995) 1306-1315.

Mezei "Liposomes—a selective drug delivery system for the topical route of administration. Lotion dosage form" Life Sci 26 (1980) 1473-1477.

Moghimi "Current progress and future prospects of liposomes in dermal drug delivery" J Microencapsul 10 (1993) 155-162.

Norimatsu "Effects of aluminum adjuvant on systemic reactions of lipopolysaccharides in swine" Vaccine 13 (1995) 1325-1329.

Paul "Transdermal immunization with large proteins by means of ultradeformable drug carriers" Eur J Immunol 25 (1995) 3521-3524.

Paul "Noninvasive administration of protein antigens: Transdermal immunization with bovine serum albumin in transferosomes" Vaccine Res 4 (1995) 145-164.

Peters "Dendritic cells: From ontogenetic orphans to myelomonocytic descendants" Immunol Today 17 (1996) 273-278.

Powers "In previously immunized elderly adults inactivated influenza A (H1N1) virus vaccines induce poor antibody responses that are not enhanced by liposome adjuvant" Vaccine 13 (1995) 1330-1335.

Ranade "Drug delivery systems. 6. Transdermal drug delivery" J Clin Pharmacol 31 (1991) 401-418.

Rao "Intracellular processing of liposome-encapsulated antigens by macrophages depends upon the antigen" Infect Immun 63 (1995) 2396-2402.

Sanchez "Formulation strategies for the stabilization of tetanus toxoid in poly(lactide-co-glycolide) microspheres" Intl J Pharm 185 (1999) 255-266.

Sauzet "Long-lasting anti-viral cytotoxic T lymphocytes induced in vivo with chimeric-multirestricted lipopeptides" Vaccine 13 (1995) 1339-1345.

Schaefer-Korting "Liposome preparations: A step forward in topical drug therapy for skin disease?" J Am Acad Dermatol 21 (1989) 1271-1275.

Scharton-Kersten "Principles of transcutaneous immunization using cholera toxin as an adjuvant" Vaccine 17 suppl 2 (1999) S37-S43.

Scharton-Kersten "Transcutaneous immunization with bacterial ADP-ribosylating exotoxins, subunits, and unrelated adjuvants" Infect Immun 68 (2000) 5306-5313.

Schmitt "Bacterial toxins: Friends or foes" Emerging Infect Dis 5 (1999) 224-234.

Schwarzenberger "Contact allergens and epidermal proinflammatory cytokines modulate Langerhans cell E-cadherin expression in situ" J Invest Dermatol 106 (1996) 553-558.

Seo "Percutaneous peptide immunization via corneum barrier-disrupted murine skin for experimental tumor immunoprophylaxis" Proc Natl Acad Sci USA 97 (2000) 371-376.

Small, In: *Handbook of Lipid Research*, Plenum, 4:43-87 and 89-96.

Stacey "Macrophages ingest and are activated by bacterial DNA" J Immunol 157 (1996) 2116-2122.

Steinman "Dendritic cells in the T-cell areas of lymphoid organs" Immunol Rev 156 (1997) 25-37.

Stingl "The immune functions of epidermal cells" Immunol Ser 46 (1989) 3-72.

Suzuki "Imiquimod, a topical immune response modifier, induces migration of Langerhans cells" J Invest Dermatol 114 (2000) 135-141.

Udey "Cadherins and Langerhans cell immunobiology" Clin Exp Immunol 107 suppl 1 (1997) 6-8.

Vassell. "Activation of Langerhans cells following transcutaneous immunization" 13 FASEB J (1999) A633.

Verma "Phagocytosis of liposomes by macrophages: intracellular fate of liposomal malaria antigen" Biochim Biophys Acta 1066 (1991) 229-238.

Verma "Adjuvant effects of liposomes containing lipid A: enhancement of liposomal antigen presentation and recruitment of macrophages" Infect Immun 60 (1992) 2438-2444.

Vutla "Transdermal iontophoretic delivery of enkephalin formulated in liposomes" J Pharm Sci 85 (1996) 5-8.

Walker "The role of percutaneous penetration enhancers" Adv Drug Delivery Rev 18 (1996) 295-301.

Wang "Induction of protective polyclonal antibodies by immunization with a *Plasmodium yoelii* circumsporozite protein multiple antigen peptide vaccine" J Immunol 154 (1995) 2784-2793.

Wang "Epicutaneous exposure of protein antigen induces a predominant Th2-like response with high IgE production in mice" J Immunol 156 (1996) 4077-4082.

Wassef "Liposomes as carriers for vaccines" Immunomethods 4 (1994) 217-222.

Weiner "Topical delivery of liposomally encapsulated interferon evaluated in a cutaneous herpes guinea pig model" Antimicrob Agents Chemotherap 33 (1989) 1217-1221.

White "Induction of cytolytic and antibody responses using *Plasmodium falciparum* repeatless circumsporozoite protein encapsulated in liposomes" Vaccine 11 (1993) 1341-1346.

White "Antibody and cytotoxic T-lymphocyte responses to a single liposome associated peptide antigen" Vaccine 13 (1995) 1111-1122.

Yasutomi "A vaccine-elicited, single viral epitope-specific cytotoxic T lymphocyte response does not protect against intravenous, cell-free simian immunodeficiency virus challenge" J Virol 69 (1995) 2279-2284.

Zellmer "Interaction of phosphatidylcholine liposomes with the human stratum corneum" Biochim Biophys Acta 1237 (1995) 176-182.

Becker "Dengue fever virus and Japanese encephalitis virus synthetic peptides, with motifs to fit HLA class I haplotypes prevalent in human populations in endemic regions, can be used for application to skin Langerhans cells to prime antiviral CD8+ cytotoxic T cells (CTLs)—A novel approach to the protection of human" Virus Genes 9 (1994) 33-45.

Becker "An analysis of the role of skin Langerhans cells (LC) in the cytoplasmic processing of HIV-1 peptides after "peplotion" transepidermal transfer and HLA class I presentation to CD8+ CTLs—An approach to immunization of humans" Virus Genes 9 (1995) 133-147.

Castle "Clinical relevance of age-related immune dysfunction" Clin Infect Dis 31 (2000) 578-585.

Chen "Adjuvation of epidermal powder immunization" Vaccine 19 (2001) 2908-2917.

Chen "Serum and mucosal immune responses to an inactivated influenza virus vaccine induced by epidermal powder immunization" J Virol 75 (2001) 7956-7965.

El-Ghorr "Transcutaneous immunization with herpes simplex virus stimulates immunity in mice" FEMS Immunol Med Microbiol 29 (2000) 255-61.

Feng "P55, an immunogenic but nonprotective 55-kilodalton *Borrelia burgdorferi* protein in murine Lyme disease" Infect Immun 64 (1996) 363-365.

Glueck "Safety and immunogenicity of intranasally administered inactivated trivalent virosome-formulated influenza vaccine *Escherichia coli* heat-labile toxin as a mucosal adjuvant" J Infect Dis 181 (2000) 1129-1132.

Gockel "Transcutaneous immunization induces mucosal and systemic immunity: a potent method for targeting immunity to the female reproductive tract" Mol Immunol 37 (2000) 537-544.

Hagiwar "Effectiveness and safety of mutant *Escherichia coli* heat-labile enterotoxin (LT H44A) as an adjuvant for nasal influenza vaccine" Vaccine 19 (2001) 2071-2079.

Hagiwara "Effects of intranasal administration of cholera toxin (or *Escherichia coli* heat-labile enterotoxin) B subunits supplemented with a trace amount of the holotoxin on the brain" 19 Vaccine (2001) 1652-1660.

Hioe "Comparison of adjuvant formulations for cytotoxic T cell induction using synthetic peptides" Vaccine 14 (1996) 412-418.

Janeway Immunobiology (1994) 10:78-10:79.

Kalbitz "Modulation der wirkstoffpenetration in die haut" Pharmazie 51 (1996) 619-637.

Katoh "Acute cutaneous barrier perturbation induces maturation of Langerhans' cells in hairless mice" Acta Derm Venereol 77(1997) 65-69.

Kumamoto "Induction of tumor-specific protective immunity by in situ Langerhans cell vaccine" Nat Biotechnol 20 (2002) 64-69.

Liu "Topical application of HIV DNA vaccine with cytokine-expression plasmids induces strong antigen-specific immune responses" Vaccine 20 (2001) 42-48.

Lu "Mutant *Escherichia coli* heat-labile enterotoxin [LT(R192G)] enhances protective humoral and cellular immune responses to orally administered inactivated influenza vaccine" Vaccine 20 (2002) 1019-1029.

Murphy "Antigen-Induced Protective and Nonprotective Cell-Mediated Immune Components against *Cryptococcus neoformans*" Infect Immun 66 (1998) 2632-2639.

Ockenhouse "Sequestrin, a CD36 recognition protein on *Plasmodium falciparum* malaria-infected erythrocytes identified by anti-idiotype antibodies" Proc Natl Acad Sci 88 (1991) 3175-3179.

Ogra "Vaccination strategies for mucosal immune responses" Clin Microbiol Rev 14 (2001) 430-445.

Podda "The adjuvanted influenza vaccines with novel adjuvants: Experience with the MF59-adjuvated vaccine" Vaccine 19 (2001) 2673-2680.

Williams "Skin absorption enhancers" Critical Rev in Therapeutic Drug Carrier Systems 9 (1992) 305-353.

Takigawa "Percutaneous peptide immunization via corneum barrier-disrupted murine skin for experimental tumor immunoprophylaxis" Ann N Y Acad Sci 941 (2001) 139-146.

Tang "Vaccination onto bare skin" Nature 388 (1997) 729-730.

"Tuberculin, Purified protein Derivative, Tine Test" Physician's desk Reference, 3 pages (2001).

Watabe "Protection against influenza virus challenge by topical application of influenza DNA vaccine" Vaccine 14 (2001) 4434-4444.

Vaccine Adjuvants—Preparation Methods and Research Protocols, Edited by D.T. O'Hagan, Humana Press, Totowa, N.J. 2000, pp. 1-5.

US 6,008,200, 12/1999, Krieg (withdrawn)

* cited by examiner

SEQUENCE LISTING

```
<160> NUMBER OF SEQ ID NOS: 2

<210> SEQ ID NO 1
<211> LENGTH: 21
<212> TYPE: DNA
<213> ORGANISM: Artificial Sequence
<220> FEATURE:
<223> OTHER INFORMATION: Synthetic Oligonucleotide

<400> SEQUENCE: 1
tccaatgagc ttcctgagtc t                                        21

<210> SEQ ID NO 2
<211> LENGTH: 20
<212> TYPE: DNA
<213> ORGANISM: Artificial Sequence
<220> FEATURE:
<223> OTHER INFORMATION: Synthetic Oligonucleotide

<400> SEQUENCE: 2
tccatgacgt tcctgacgtt                                          20
```

USE OF PENETRATION ENHANCERS AND BARRIER DISRUPTION METHODS TO ENHANCE THE IMMUNE RESPONSE OF ANTIGEN AND ADJUVANT

RELATED APPLICATIONS

The present application is a continuation application of U.S. application Ser. No. 09/257,188, filed Feb. 25, 1999, now U.S. Pat. No. 6,797,276, which is a continuation-in-part of U.S. application Ser. No. 08/749,164, filed Nov. 14, 1996, now U.S. Pat. No. 5,910,306; U.S. application Ser. No. 08/896,085, filed Jul. 17, 1997, now U.S. Pat. No. 5,980,898; and PCT/US97/21324 designating the U.S., filed Nov. 14, 1997, now abandoned, published under PCT Article 21(2) in English. U.S. application Ser. No. 09/257,188 claims the benefit of U.S. Provisional Application No. 60/075,850, filed Feb. 25, 1998; U.S. Provisional Application No. 60/075,856, filed Feb. 25, 1998; and U.S. Provisional Application No. 60/086,251, filed May 21, 1998. All of the foregoing documents are herein incorporated by reference in their entirety.

BACKGROUND OF THE INVENTION

1. Field of the Invention

The invention relates to transcutaneous immunization using an ADP-ribosylating exotoxin or other adjuvants with an antigen, and the use of penetration enhancers and barrier disruption agents to enhance the immune response. The invention also relates to activation of the antigen, adjuvant, their targets in the skin, or a combination thereof to enhance the antigen-specific immune response induced thereto.

2. Description of the Related Art

Skin, the largest organ of the human body, is an important part of the body's defense against invasion by infectious agents and contact with noxious chemicals (see Bos, 1997). Unwanted skin reactions such as allergic or atopic dermatitis are known, but induction of a systemic immune response by application of an adjuvant and antigen which elicits specific immune effectors and provides a therapeutic advantage by simple application of adjuvant and antigen to skin does not appear to have been taught or suggested prior to our invention.

Cholera toxin (CT) and heat labile interotoxin from *E. coli* (LT) are examples of a noxious chemical, which one would have expected the protective layers of skin to protect against penetration by the noxius substances. Craig (1965) reported that stool filtrates of cholera patients injected intracutaneously into rabbits or guinea pigs produced a characteristic delayed, sustained edematous induration (swelling), which was induced by the presence of toxin in the skin. The swelling and vascular leakage was so dramatic that it was ascribed to an unknown permeability factor which was later shown to be CT itself. Thus, one could have reasonably expected that CT would be extremely reactogenic when placed on the skin, if it were to enter the skin, causing similar redness and swelling. The Craig test injecting CT into the skin, became a standard measurement for the presence and amount of CT in stool filtrates or culture media. Data confirmed that this skin reactivity was due to cholera toxin (see Finkelstein and LoSpallutto, 1969).

Craig (1965) cautioned, "The absence of skin lesions in clinical cholera certainly does not preclude the possibility that the noxa responsible for gut damage could also have a deleterious effect upon the skin provided it is applied to skin in sufficient concentration". The extreme reactogenicity of cholera toxin in the skin was used as a test for its toxicity and the prior art evidenced an expectation that cholera toxin would be reactogenic if applied to the skin, producing an undesirable reaction. Such adverse reactions have been well documented by known authorities in the field (Craig, 1972).

In contrast, we have shown cholera toxin to be immunogenic, acting as both antigen and adjuvant, when placed on the skin but without any resulting local or systemic side effects. This lack of reactogenicity when cholera toxin was placed on the skin for transcutaneous immunization was surprising and contradicted conclusions one would have drawn from the prior art. Specifically, CT placed on the skin according to our invention acts as a non-toxic, non-reactogenic adjuvant, in contrast to the expectations of Craig, while injection of CT into the skin results in swelling and redness. Thus, it was not obvious prior to our invention that cholera toxin or other ADP-ribosylating exotoxins or allow adjuvants applied topically would be useful for transcutaneous immunization. In fact large doses of heat labile enterotoxin (LT) placed on the skin of humans has been shown to induce a systemic immune response without local or systemic toxicity.

This unexpected absence of reactogenicity is extremely important to the use of vaccines. Vaccine antigens and adjuvants are useful when immunization produces a protective immune response without significant unwanted reactions. Historically, reactogenicity of vaccines such as swelling, tenderness and pain at the site of injection has in some cases (e.g., typhoid and pertussis) been accepted because of the benefits of vaccination. However, high levels of reactogenicity and other side effects are not desirable, and would be problematic for development of new vaccine adjuvant and antigen candidates. Research efforts are focused on making vaccine adjuvants that are stimulatory and do not inducing unwanted reactions. Whole cell pertussis vaccines induce systemic and local side effects and, as a result, this effective vaccine and time tested vaccine is being replaced by acellular pertussis vaccines solely because they are less reactogenic.

The present invention differs from that of U.S. Pat. No. 5,830,877 which teaches the use of a naked plasmid that encodes for biologically active peptides into a mammalian host. The invention described herein teaches the use of an adjuvant and antigen or nucleic acid administered together on the skin to induce an immune response. The invention described herein further differs from that of U.S. Pat. No. 5,830,877 which teaches away from the use of peptides that are not encoded in a nucleic acid and produced by the host cell because of the toxicity associated with biologically active peptides, the problems and cost of isolating, purifying and synthesizing peptides and their short half life in vivo resulting form degradation by proteases present in the target tissue. This clearly teaches away from the addition of an adjuvant such a cholera toxin to a coadministered antigen or nucleic acid. In fact the novelty of the ability of a large molecule such as CT to induce an immune response by application through the skin without toxicity has led to a number of scientific papers describing this novelty and public excitement over the potential implication of delivery of proteins for vaccination by skin application. Unlike U.S. Pat. No. 5,830,877 the present invention is not dependent on stimulation of local inflammation or irritation. Unlike U.S. Pat. No. 5,830,877 the invention does not depend on irritation or local inflammation to increase the permeability of cell membranes to enhance the uptake of the antigens, plasmids or RNA. In fact the striking feature regarding Transcutaneous Immunization is the absence of local inflammation.

Unlike the present invention, U.S. Pat. No. 5,824,313 teaches the application of extremely small (less than 500 daltons) lymphoid organ modifying agents such as 1,25-dihydroxy-16-ene Vitamin D.sub.3 and calcipotriene or dehydroepiandrosterone (DHEA), DHEA congeners and DHEA-derivatives with the intramuscular injection of an antigen to affect antibody responses.

Transcutaneous immunization requires both passage of an antigen through the outer barriers of the skin, which was thought to be impervious to such passage, and an immune response to the antigen. Fisher's Contact Dermatitis states that molecules of greater than 500 daltons cannot normally penetrate the skin. There is a report by Paul et al. (1995) of induction of an immune response with transferosomes, a lipid structure distinct from liposomes. In this publication, the transferosomes were used as a vehicle for antigen (bovine serum albumin and gap junction proteins) and complement-mediated lysis of antigen-sensitized liposomes was assayed. The limit to penetration of the skin by antigen was stated to be 750 daltons. In their study, an immune response was not induced when a solution containing antigen was placed on the skin; only transferosomes were able to induce an immune response. Paul and Cvec (1995) also stated that it is "impossible to immunize epicutaneously with simple peptide or protein solutions".

Such references explain why our successful use of a molecule like cholera toxin (which is 85,000 daltons) as an antigen or adjuvant in immunization was greeted with surprise by the field because such large molecules were not expected to penetrate the skin and, therefore, would not be expected to induce a specific immune response.

However, we have shown in U.S. application Ser. No. 08/749,164 (filed Nov. 14, 1996); U.S. application Ser. No. 08/896,085 (filed Jul. 17, 1997); and international application PCT/US97/21324 (filed Nov. 14, 1997) that using an ADP-ribosylating exotoxin, such as cholera toxin, as an antigen could elicit a strong antibody response that is highly reproducible. When an ADP-ribosylating exotoxin, such as cholera toxin, was used as an immunoadjuvant and applied to the skin in a saline solution with a separate antigen (e.g., diphtheria toxoid), a systemic and mucosal antigen-specific antibody response could be elicited. In the present application, we disclose that transcutaneous immunization using a penetration enhancer, a barrier disruption agent, or combinations thereof may improve the adjuvant activity of a bacterial exotoxin.

We have shown that like cholera toxin (CT), heat-labile enterotoxin from *E. coli* (LT), *Pseudomonas* exotoxin A (ETA), pertussis toxin (PT) and a wide variety of antigens including killed rabies virus, recombinants such as HIV p55 gag, polysaccharide conjugates such as Hib, sonicates, pertactin for example, are able to pass through the skin and induce an immune response. Additionally CT, LT, ETA and PT and bacterial DNA and cytobines, can act as adjuvants to induce an immune response to antigens co-administered on the skin. Thus tetanus toxoid, not immunogenic by itself on the skin, can induce a strong immune response when placed on the skin with CT. We have proposed that the Langerhans cell population underlying the site of application are a preferred antigen presenting cell for delivering antigen to the immune system. Adjuvant may act on the antigen presenting cell directly, or through lymphocytes recognizing antigen.

We propose to enhance the immune response to transcutaneously adjuvant and/or antigen utilizing penetration enhancement techniques. According to Hurley, "Skin owes its durability to the dermis, but its chemical impermeability resides in the epidermis and almost exclusively in its dead outer layer, the stratum corneum". For transcutaneous immunization using, for example, an ADP-ribosylating exotoxin as adjuvant and a soluble protein antigen such as diphtheria toxoid, penetration of the stratum corneum must occur. Penetration enhancement techniques would be designed to increase the movement of transcutaneous antigens and adjuvants through the stratum corneum layer of skin.

Further, we propose that transcutaneous immunization using activation of at least one of the antigen, adjuvant and skin component will enhance the immune response as assayed by quantitative and qualitative parameters. Antigen-adjuvant of the formulation may be activated by trypsin cleavage of a bacterial exotoxin (e.g., trypsin-cleaved LT, with or without reduction). Activation of the skin at the application site of the formulation may be accomplished by the use of barrier disruption agents (e.g., acetone, alcohol) which increases the size or activation of the underlying Langerhans cell population, or by an enzyme or combination of enzymes (e.g., enzymes with sialidase activity) which increases the amount or accessibility of ganglioside GM1 receptor.

SUMMARY OF THE INVENTION

An object of the invention is to provide an enhanced system for transcutaneous immunization which induces an immune response (e.g., humoral and/or cellular effector) in a subject, a subject being an animal or human. This delivery system provides simple application to intact skin of an organism of a formulation comprised of antigen and adjuvant to induce a specific immune response against the antigen. Although not required for induction of an immune response by this simple delivery system, supplementation of the aforementioned process with penetration enhancement or barrier disruption may enhance immunization and/or vaccination.

In particular, the adjuvant or antigen or skin may assist in the penetration of the stratum corneum or epidermis to encounter the antigen presenting cells of the immune system (e.g., Langerhans cells in the epidermis, dermal dendritic cells, dendritic cells, follicular dendritic cells, macrophages, B lymphocytes) and/or induce the antigen presenting cells to phagocytose the antigen. The antigen presenting cells then present the antigen to T and B cells. In the instance of Langerhans cells, the antigen presenting cells then may migrate from the skin to the lymph nodes and present antigen to lymphocytes (e.g., B and/or T cells), thereby inducing an antigen-specific immune response.

In addition activation of the antigen, adjuvant, skin, or any combination thereof may be accomplished to supplement the immunization process.

In addition to eliciting immune reactions leading to generation of an antigen-specific B lymphocyte and/or T lymphocyte, including a cytotoxic T lymphocyte (CTL), another object of the invention is to positively and/or negatively regulate components of the immune system by using the transcutaneous immunization system to affect antigen-specific helper (Th1 and/or Th2) or delayed-type hypersensitivity (DTH) T-cell subsets. This can be exemplified by the differential behavior of CT and LT which can result in different T-helper responses or different levels of protection in in-vivo challenge molds using transcutaneous immunization.

DESCRIPTION OF PREFERRED EMBODIMENTS

Figure 1A:
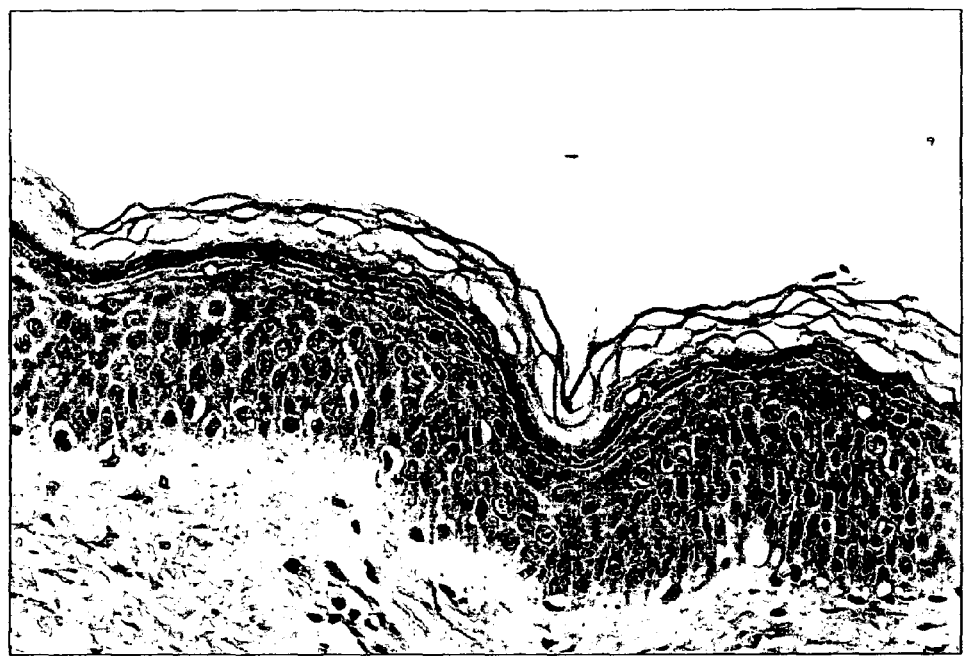
FIGS. 1a-f are photographs showing no inflammation at the site of immunization (A,B), Langerhans cell activation by LT in human skin at the site of immunization (C,E) and the absence of Langerhans cell activation in skin from the contralateral arm (D,F).

In one embodiment of the invention, a formulation containing antigen and adjuvant such as CT and DT, is applied to intact skin of an organism after penetration enhancement of the skin, the antigen is presented to immune cells, and an antigen-specific immune response is induced without perforating the skin. The formulation may include additional antigens or nucleic acids such that transcutaneous application of the formulation induces an immune response to multiple antigens, or nucleic acids encoding for antigens preferably from 2 to 20 but possibly up to 200. In such a case, the antigens may or may not be derived from the same source, but the antigens will have different chemical structures so as to induce immune responses specific for the different antigens. Antigen-specific lymphocytes may participate in the immune response and, in the case of participation by B lymphocytes, antigen-specific antibodies may be part of the immune response.

In another embodiment of the invention, the invention is used to treat an organism. If the antigen is derived from a pathogen, the treatment vaccinates the organism against infection by the pathogen or against its pathogenic effects such as those caused by toxin secretion. A formulation that includes a tumor antigen may provide a cancer treatment; a formulation that includes an allergen may be used to treat for allergic disease; a formulation that includes an autoantigen may provide a treatment for a disease caused by the organism's own immune system (e.g., autoimmune disease). The invention may be used therapeutically to treat existing disease, protectively to prevent disease, or to reduce the severity and/or duration of disease.

In a further embodiment of the invention, a patch for use in the above methods is provided. The patch may comprise a dressing, and effective amounts of antigen or nucleic acids and adjuvant. The dressing may be occlusive or non-occlusive. The patch may contain penetration enhancers or may include a device for physical penetration enhancement. The patch may include additional antigens such that application of the patch induces an immune response to multiple antigens. In such a case, the antigens may or may not be derived from the same source, but the antigens will have different chemical structures so as to induce an immune response specific for the different antigens. For effective treatment; multiple patches may be applied at frequent intervals or constantly over a period of time.

Moreover, in yet another embodiment of the invention, the formulation is applied to intact skin overlying more than one draining lymph node field using either single or multiple applications or a separate patch for adjuvant or antigen/nucleic acid. The formulation may include additional antigens such that application to intact skin induces an immune response to multiple antigens. In such a case, the antigens may or may not be derived from the same source, but the antigens will have different chemical structures so as to induce an immune response specific for the different antigens.

The formulation may be applied to the skin to boost or prime the immune response in conjunction with other routes of immunization. Thus, priming with transcutaneous immunization with either single or multiple applications may be followed with oral, nasal, or parenteral techniques for boosting immunization with the same or altered antigens. The formulation may include additional antigens such that application to intact skin induces an immune response to multiple antigens. In such a case, the antigens may or may not be derived from the same source, but the antigens will have different chemical structures so as to induce an immune response specific for the different antigens.

In addition to antigen and activated adjuvant, the formulation may comprise a vehicle. For example, the formulation may comprise AQUAPHOR (an emulsion of petrolatum, mineral oil, mineral wax, wool wax, panthenol, bisabol, and glycerin), emulsions (e.g., aqueous creams), microemulsions, gels, oil-in-water emulsions (e.g., oily creams), anhydrous lipids and oil-in-water emulsions, anhydrous lipids and water-in-oil emulsions, fats, waxes, oil, silicones, and humectants (e.g., glycerol).

The antigen may be derived from a pathogen that can infect the organism (e.g., bacterium, virus, fungus, or parasite), or a cell (e.g., tumor cell or normal cell) or allergen or biological warfare agent. The antigen may be a tumor antigen or an autoantigen. Chemically, the antigen may be a carbohydrate, glycolipid, glycoprotein, lipid, lipoprotein, phospholipid, polypeptide, or fusion protein (recombinant) or chemical conjugate of the above. The molecular weight of the antigen may be greater than 500 daltons, preferably greater than 800 daltons, and more preferably greater than 1000 daltons.

Antigen may be obtained by recombinant means, chemical synthesis, or purification from a natural source. One advantage of transcutaneous immunization may be that purification of an antigen is not necessary e.g. a whole organism may be sonicated and used for immunization. The level of toxicity associated with injecting a product from such a preparation is often too toxic to be tolerated, such as LPS, which can be fatal if injected, but is non-toxic on the skin. Preferred are proteinaceous antigen or conjugates with polysaccharide. Antigen may be at least partially purified in cell-free form. Alternatively, antigen may be provided in the form of a live virus, an attenuated live virus, or an inactivated virus, sonicated or lysed whole bacterium, parasite or detergent treated virus, or fraction thereof.

Inclusion of an adjuvant may allow potentiation or modulation of the immune response. Moreover, selection of a suitable antigen or adjuvant may allow preferential induction of a humoral or cellular immune pr mucosal response, specific antibody isotypes (e.g., IgM, IgD, IgA1, IgA2, IgE, IgG1, IgG2, IgG3, and/or IgG4), and/or specific T-cell subsets (e.g., CTL, Th1, Th2 and/or $T_{DTH}$). Optionally, antigen, adjuvant, may be provided in the formulation by means of a nucleic acid (e.g., DNA, RNA, cDNA, cRNA) encoding the antigen or adjuvant as appropriate with a antigen or adjuvant that has been added to the nucleic acid. This technique is called genetic immunization.

The term "antigen" as used in the invention, is meant to describe a substance that induces a specific immune response when presented to immune cells of an organism. An antigen may comprise a single immunogenic epitope, or a multiplicity of immunogenic epitopes recognized by a B-cell receptor (i.e., antibody on the membrane of the B cell)

or a T-cell receptor. A molecule may be both an antigen and an adjuvant (e.g., cholera toxin) and, thus, the formulation may contain only one component. Antigen may be provided as a whole organism such as, for example, a bacterium or virion; antigen may be obtained from an extract or lysate, either from whole cells or membrane alone; or antigen may be chemically synthesized for produced by recombinant means.

The term "adjuvant" as used in the invention, is meant to describe a substance added to the formulation to assist in inducing an immune response to the antigen.

The term "effective amount" as used in the invention, is meant to describe that amount of antigen which induces an antigen-specific immune response. Such induction of an immune response may provide a treatment such as, for example, immunoprotection, desensitization, immunosuppression, modulation of autoimmune disease, potentiation of cancer immunosurveillance, or therapeutic vaccination against an established infectious disease.

By the epidermis we mean the cells of the skin from the basal layer of kertinoctyes and basal lamina up to and through the stratum corneum.

The definition of transdermal is generally held to be: Relating to, being, or supplying a medication in a form for absorption through the skin into the bloodstream (~drug delivery) (~nitroglycerin) (~nicotine patch). [2]Frederick C. Mish et al., eds., *Merriam-Webster's Collegiate Dictionary*, 10th ed. (Springfield, Mass.: Merriam-Webster, Incorporated, 1997), 861.

The term draining lymph node field as used in the invention means an anatomic area over which the lymph collected is filtered through a set of defined set of lymph nodes (e.g., cervical, axillary, inguinal, epitrochelear, popliteal, those of the abdomen and thorax).

Skin penetration may be enhanced using techniques that increase skin hydration. According to Roberts and Walker (1993), "The state of hydration of the stratum corneum (SC) is one of the most important factors in determining the rate of percutaneous absorption of a given solute". The state of hydration interacts with the principal of diffusion in determining the rate of absorption of a substance through the skin. Furthermore, Hurley stated:

"Absorption of substances through the stratum corneum is believed to occur by diffusion in accordance with Fick's laws of diffusion in which the rate of absorption of a chemical is proportional to the concentration difference across the membrane. Thus, a concentration gradient between the high concentration of solute on the skin surface and its absence or low concentration below the stratum corneum is the driving force in this process. Transcorneal movement of absorption is classically represented as 'percellular', that is, directly through the cell walls of the compacted corneum and not intercellularly. Intracellular protein filaments are described as the pathways for polar (water soluble) compounds and the medium between filaments serves as the route for nonpolar (lipid-soluble) substances . . . Hydration increases the permeability of the stratum corneum for most substances by a number of cytophysical mechanisms that are not completely clarified."

Thus, while skin hydration is generally known to enhance skin penetration, the mechanisms by which this occurs are not entirely clear and, thus, not predictable prior to the present invention and not thought to allow penetration of large molecules. (7750 daltons).

The use of vehicles for increasing hydration is well known. Occlusive dressings, such as vapor-impenetrable plastic films (e.g., polyvinylidine, polyethylene) enhance absorbtion principally through increased hydration of the stratum corneum, a result of swelling of the corneocytes, and uptake of water into the intercellular corridors. Hydrocolloid patches may also be used to enhance skin penetration. Absorbtion of steroids can be increase over 100 fold using plastic occlusive film. Generally, greases, oils or impermeable plastic induce the most hydration by occlusion. See, for example, Idson (1978); Hollingsbee (1995); and Mckenzie and Stoughton (1962). The use of hydration or vehicle for hydration with an antigen and adjuvant were not known prior to our invention as penetration. The skin was thought to be limited to small molecules even in the hydrated state.

Suitable agents which are known to enhance absorption of drugs through skin are described in Sloan, Use of Solubility Parameters from Regular Solution Theory to Describe Partitioning-Driven Processes, Ch. 5, "Prodrugs: Topical and Ocular Drug Delivery" (Marcel Dekker, 1992), and at places elsewhere in the text.

It is expected that these techniques (and others which are conventionally used to facilitate drug delivery) may be adapted to preparation of nucleic acids for use in the methods of the invention by those of ordinary skill in the art without undue experimentation. Specific examples illustrating this suitability are set forth below.

The state of the art in skin penetration enhancement is described in Pharmaceutical Skin Penetration Enhancement Edited by Kenneth A. Walters and Jonathan Hadgraft, Published by Marcel Dekker, Inc., New York, 1993.

Skin permeability and/or skin hydration may be expected by selecting an appropriate vehicle from different classes, such as humectant (e.g., glycols, glycerols), powder, (e.g., clays, shake lotions), oil/water (O/W) emulsion (e.g., aqueous creams), water/oil emulsion (e.g., oily creams), emulsifying base (e.g., anhydrous lipid and O/W emulsifiers), absorbtion base (e.g., anhydrous lipid and W/O emulsifiers), lipophilic (e.g., fats, waxes, oils, silicones), and occlusive dressing (e.g., plastic wrap).

Other methods that disrupt the stratum corneum proteins to enhance penetration in the present invention may be employed. Salicylic acid is a keratinolytic that may increase absorption. Urea acts both as a keratinolytic and hydrater of the skin, and may act as a penetration enhancer. Phospholipase A2 and phosphatidylcholine dependent phospholipase C may be used as epidermal enzymes to enhance penetration. Other penetration enhancers may include ethanol, acetone, detergents, bases, nair©, propylene glycol, pyrriolidones, dimethylacetamide, dimethylformamide, dimethylsulfoxide, alkyl sulfoxide, phosphine oxide, surfactants and caprolactams such as azone. Other compounds that may be used for penetration enhancement include amines and amides, alkyl N,N-distributed-amino acetates, decylmethylsulfoxide, pyrrolidones, pirotiodecane (HPE-101), benzlyalkonium, benzylalkonium chloride polymers, silicone based polymers, fatty acids, cyclic ureas, terpenes, liposomes, and cyclodextrins. Penetration enhancers are well known in the art, for example as described in Pharmaceutical Penetration Enhancement, (Marcel Dekker, 1993) Other techniques that may be employed for penetration include iontophoresis, ultrasound, electroporation, tape stripping, the use of gene guns or other propellant devices, tines such as used for TB tine tests (as provided by Mono-Vacc system) or microneedles which penetrate the outer surface of the skin, or abrasives which remove the outer layers of the skin and lipid extraction.

A device which may be used for disruption of the stratum corneum (which is distributed in the U.S. by Connaught Laboratories, Inc. of Swiftwater, Pa.) consists of a plastic container having a syringe plunger at one end and a tyne disk at the other. The tyne disk supports a multiplicity of narrow diameter tynes of a length which will just scratch the outermost layer of epidermal cells but not penetrate the epidermis. Each of the tynes in the MONO-VACC kit is coated with old tuberculin; in the present invention, each needle may be coated with a pharmaceutical composition of antigen/nucleic acid and adjuvant. Use of the device with the present invention may not be according to the manufacturer's written instructions included with the device product because when used with the present invention does not penetrate the epidermis. Hereto, the device may be used for surface disruption to disrupt the outermost layes of the skin, the stratum corneum and upper epidermis, to enhance the transcutaneous immunization. Similar devices which may also be used in this embodiment are those which are currently used to perform allergy tests.

Other approaches include barrier disruption. Inhibition of cholesterol synthesis using systemically administered HMG CoA reductase inhibitors and similar drugs interfere with barrier function and may allow enhanced penetration of the formulation component.

It is also conceivable that the skin can be transformed to enhance the transcutaneous immune response. CT and LT exert their effect via the ganglioside GM1 binding by the B subunit. Ganglioside GM1 is a ubiquitous cell membrane glycolipid found in all mammalian cells. In the gastrointestinal tract, when the pentameric CT B subunit binds to the cell surface, a hydrophilic pore is formed which allows the A subunit to penetrate across the lipid bilayer. The skin contains gangliosides at a concentration of 30-35 nmol NeuAC/gm. Skin gangliosides are possible targets for initiating transcutaneous immunization via mechanisms such as Langerhans cells activation as described above.

One possible method to activate the skin for enhancing the effect of transcutaneous immunization with ADP ribosylating exotoxins by increasing the number of GM1 ganglioside molecules in skin cells. This could be achieved by activation of receptor cells using sialidase to convert gangliosides that do not bind the toxin into the sialidase-stable cholera toxin binding ganglioside GGnSLC (ganglioside GM1):

"It is interesting that the cholera *vibrio* is perhaps the best-known source of sialidase (or neuraminidase, as it is often called). Could this sialidase play a part in the natural history of the disease by making more receptors available for the toxin? If so, should any active immunizing agent the disease contain an anti-neuriminidase element? Incubation of intestinal scrapings with sialidase leads to a considerable increase in their ability to bind the toxin, which is due not only to conversion of sialidase-labile ganglioside to cholera toxin-binding ganglioside, but also, apparently to the unmasking of otherwise unapproachable ganglioside binding sites possibly by breaking down glycoproteins. Pretreatment of dog intestine with sialidase makes it produce more fluid in response to cholera toxin; treatment of adrenal cells with sialidase increases their responsiveness to cholera toxin; pretreatment of pigeon red cells with sialidase increases the activation of the adenylate cyclase in them by cholera toxin.

The biochemistry of cholera, In: Cholera: The American Scientific Experience, 1947-1980, van Heyningen, W. E., and Seal, J. R., Eds, Waterview Press, Boulder, 1983, page 263 (citations omitted).

The effect of treatment of the skin with sialidase may enhance the binding of an ADP ribosylating exotixin such as CT to the immune cells targeted by transcutaneous immunization. This represents a kind of activation of the skin for transcutaneous immunization. Additionally, neuraminidase may act as an epidermal enzyme concurrently enhancing penetration.

The use of a penetration enhancer may be used in conjunction with activation of the skin. Activation of the skin for transcutaneous immunization may also be after treatments such as acetone or alcohol swabbing. It has been shown that skin barrier disruption using acetone swabbing of the skin increased Langerhans cell density by 80% and increased the reaction to contact allergens in vivo. If the density of Langerhans cells is increased, then the potency of the immune response may be increased. Similar chemical disruption might be expected to increase the number of Langerhans cells and result in activation of the skin component of transcutaneous immunization, by tape stripping, sodium dodecyl sulfate, the use of alcohol swabbing, or a depilatory such as calcium hydroxide. See Proksch and Brasch (1996, 1997) for use of penetration enhancers and barrier disruption in allergic contact dermatitis.

Penetration enhancement may be achieved by performance of simple maneuvers such as alcohol swabbing immediately prior to immunization, by concurrent use of penetration enhancement compounds or techniques or by techniques such as acetone swabbing 24 hours prior to increase the number of Langerhans cells.

Processes for preparing a pharmaceutical formulation are well-known in the art, whereby the antigen and adjuvant is combined with a pharmaceutically acceptable carrier vehicle. Suitable vehicles and their preparation are described, for example, in Remington's Pharmaceutical Sciences by E. W. Martin. Such formulations will contain an effective amount of the antigen and adjuvant together with a suitable amount of vehicle in order to prepare pharmaceutically acceptable compositions suitable for administration to a human or animal. The formulation may be applied in the form of an cream, emulsion, gel, lotion, ointment, paste, solution, suspension, or other forms known in the art. In particular, formulations that enhance skin hydration, penetration, or both are preferred. There may also be incorporated other pharmaceutically acceptable additives including, for example, diluents, excipients, binders, stabilizers, preservatives, and colorings.

Without being bound to any particular theory but only to provide an explanation for our observations, it is presumed that the transcutaneous immunization delivery system carries antigen to cells of the immune system where an immune response is induced. The antigen may pass through the normal protective outer layers of the skin (i.e., stratum corneum) and induce the immune response directly, or through an antigen presenting cell (e.g., macrophage, tissue macrophage, Langerhans cell, dendritic cell, dermal dendritic cell, B lymphocyte, or Kupffer cell) that presents processed antigen to a T lymphocyte (see Stingl et al., 1989; Streilein and Grammer, 1989; Tew et al., 1997). Optionally, the antigen may pass through the stratum corneum via a hair follicle or a skin organelle (e.g., sweat gland, oil gland).

Transcutaneous immunization with bacterial ADP-ribosylating exotoxins (bAREs) may target the epidermal Langerhans cell, known to be among the most efficient of the antigen presenting cells (APCs). We have found that bAREs activate Langerhans cells when applied epicutaneously to the skin in saline solution. Adjuvants such as activated LT may greatly enhance Langerhans cell activation. The Langerhans cells direct specific immune responses through phagocytosis of the antigens, and migration to the lymph nodes where they act as APCs to present the antigen to lymphocytes, and thereby induce a potent antibody response. Although the skin is generally considered a barrier to invading organisms, the imperfection of this barrier is attested to by the numerous Langerhans cells distributed throughout the epidermis that are designed to orchestrate the immune response against organisms invading via the skin. According to Udey (1997):

"Langerhans cells are bone-marrow derived cells that are present in all mammalian stratified squamous epithelia. They comprise all of the accessory cell activity that is present in uninflamed epidermis, an in the current paradigm are essential for the initiation and propagation of immune responses directed against epicutaneously applied antigens. Langerhans cells are members of a family of potent accessory cells ('dendritic cells') that are widely distributed, but infrequently represented, in epithelia and solid organs as well as in lymphoid tissue.

"It is now recognized that Langerhans cells (and presumably other dendritic cells) have a life cycle with at least two distinct stages. Langerhans cells that are located in epidermis constitute a regular network of antigen-trapping 'sentinel' cells. Epidermal Langerhans cells can ingest particulates, including microorganisms, and are efficient processors of complex antigens. However, they express only low levels of MHC class I and II antigens and costimulatory molecules (ICAM-1, B7-1 and B7-2) and are poor stimulators of unprimed T cells. After contact with antigen, some Langerhans cells become activated, exit the epidermis and migrate to T-cell-dependent regions of regional lymph nodes where they local as mature dendritic cells. In the course of exiting the epidermis and migrating to lymph nodes, antigen-bearing epidermal Langerhans cells (now the 'messengers') exhibit dramatic changes in morphology, surface phenotype and function. In contrast to epidermal Langerhans cells, lymphoid dendritic cells are essentially non-phagocytic and process protein antigens inefficiently, but express high levels of MHC class I and class II antigens and various costimulatory molecules and are the most potent stimulators of naive T cells that have been identified."

We envision that the potent antigen presenting capability of the epidermal Langerhans cells can be exploited for transcutaneously delivered vaccines. A transcutaneous immune response using the skin immune system would require delivery of vaccine antigen only to Langerhans cells in the stratum corneum (the outermost layer of the skin consisting of cornified cells and lipids) via passive diffusion and subsequent activation of the Langerhans cells to take up antigen, migrate to B-cell follicles and/or T-cell dependent regions, and present the antigen to B and/or T cells. If antigens other that bAREs (for example diptheria toxoid) are to be phagocytosed by the Langerhans cells, then these antigens could also be taken to the lymph node for presentation to T-cells and subsequently induce an immune response specific for that antigen (e.g., diptheria toxoid). Thus, a feature of transcutaneous immunization is the activation of the Langerhans cell, presumably by bacterial ADP-ribosylating exotoxins, ADP-ribosylating exotoxin binding subunits (e.g., cholera toxin B subunit), or other adjuvants or Langerhans cell activating substance. Increasing the skin population of Langerhans cells using strategies such as acetone swabbing could then be expected to enhance the transcutaneous immune response.

The spectrum of more commonly known skin immune responses is represented by contact dermatitis and atopy. Contact dermatitis, a pathogenic manifestation of LC activation, is directed by Langerhans cells which phagocytose antigen, migrate to lymph nodes, present antigen, and sensitize T cells that migrate to the skin and cause the intense destructive cellular response that occurs at affected skin sites (Dahl, 1996; Leung, 1997). Atopic dermatitis may utilize the Langerhans cell in a similar fashion, but is identified with Th2 cells and is generally associated with high levels of IgE antibody (Dahl, 1996; Leung, 1997).

Transcutaneous immunization with cholera toxin and related bAREs on the other hand is a novel immune response with an absence of superficial and microscopic post-immunization skin findings (i.e., non-inflamed skin) shown by the absence of lymphocyte infiltration 24, 48 and 120 hours after immunization. This is strikingly shown by completion of a Phase I trial in which humans were immunized with LT under a simple occlusive patch. Potent anti-LT IgG and IgA antibodies were stimulated. Two volunteers had biopsies performed at the site of immunization. Micro-scopic evaluation confirmed the clinical observation that no inflammation was seen. This suggests that Langerhans cells, which "comprise all of the accessory cell activity that is present in uninflammed epidermis, and in the current paradigm are essential for the initiation and propagation of immune responses directed against epicutaneously applied antigens" (Udey, 1997) may have been recruited. The uniqueness of the transcutaneous immune response here is also indicated by the both high levels of antigen-specific IgG antibody, and the type of antibody produced (e.g., IgG1, IgG2a, IgG2b, IgG3 and IgA) and the absence of anti-CT IgE antibody. However, other immune cells may be engaged and speculation on the mechanism should not limit the invention.

Thus, we have found that bacterial-derived toxins applied to the surface of the skin can activate Langerhans cells and that TCI induces a potent immune response manifested as high levels of antigen-specific circulating IgG antibodies and would expect that penetration enhancement would enhance the immune response. Transcutaneous adjuvant and penetration enhancer may be used in transcutaneous immunization to enhance the IgG antibody or T-cell response to proteins not otherwise immunogenic by themselves when placed on the skin.

Transcutaneous targeting of Langerhans cells may also be used to deactivate their antigen presenting function, thereby preventing immunization or sensitization. Techniques to mobilize Langerhans cells or other skin immune cells yet negatively modulate them include, for example, the use of anti-inflammatory steroidal or non-steroidal agents (NSAID), cyclophosphamide or other imnunosuppressants, interleukin-10, TGFβ monoclonal antibody to interleukin-1, ICE inhibitors or depletion via superantigens such as through staphylococcal enterotoxin-A (SEA) induced epidermal Langerhans cell depletion.

Transcutaneous immunization may be induced via the ganglioside GM1 binding activity of CT, LT or subunits such as CTB. Ganglioside GM1 is a ubiquitous cell membrane glycolipid found in all mammalian cells. When the pentameric CT B subunit binds to the cell surface a hydrophilic pore is formed which allows the A subunit to penetrate across the lipid bilayer.

We have shown that transcutaneous immunization by CT or CTB may require ganglioside GM1 binding activity. When mice are transcutaneously immunized with CT, CTA and CTB, only CT and CTB resulted in an immune response. CTA contains the ADP-ribosylating exotoxin activity but only CT and CTB containing the binding activity are able to induce an immune response indicating that the B subunit was necessary and sufficient to immunize through the skin. We conclude that the Langerhans cell or other immune cells may be activated by CTB binding to its cell surface, but more activated by the concurrent presence of the A-subunit.

In addition to activation of the skin component in the immunization process of the present invention, the antigen and/or adjuvant may be activated to enhance immunization. When CT is secreted, cleavage occurs at the trypsin recognition site and the toxin is activated. LT however, is secreted with its trypsin recognition site intact. When LT is secreted in the gastrointestinal tract and thereby exposed to gastrointestinal agents such as trypsin, the proteolytically sensitive residues that join A1 and A2 subunits of LT are cleaved, allowing the A1 subunit to ADP-ribosylate G proteins and therefore exert its toxic effects. The lack of trypsin or related agents in the skin may prevent trypsin cleavage of the proteolytically sensitive residues that join A1 and A2 subunits of LT, diminishing its adjuvant activity.

These two bacterial enterotoxins have many features in common. LT and CT have the same subunit number (A2:B5) and arrangement, and the same biological mechanism of action. An amino acid sequence similarity of 75-77% is found for both chains when comparing LT and CT, and the most significant difference occurs in the respective A chains at positions 192-195. At this site the cleavage of the A chain by trypsin occurs and the site is situated between two cysteine residues that form the internal disulfide bond of the A chain. See, for example, Mekalanos et al. (1979), Spangler (1992), and Sniderman (1995). We propose that these structural differences between the molecules are a significant influence not only on their enterotoxic properties, but also on their ability to function as adjuvants.

Unlike CT produced by *V. cholerae*, LT is not fully biologically active when first isolated from the bacterial cell. Consistent with the A-B model for bacterial toxins, LT requires trypsin proteolysis and disulfide reduction to be fully active (Sniderman, 1995). In the absence of proteolytic processing, the enzymatically active A1 moiety is unable to dissociate from the A2 component and cannot reach its target substrate (adenylate cyclase) on the basolateral surface of the intestinal epithelial cell. This difference in activation of the isolated material results in differences in response thresholds for LT and CT in biologic systems. For instance, CT induces detectable net fluid secretion in the mouse intestine at a dose of 5 to 10 µg. LT induces detectable net secretion in this assay at 50 to 100 µg. In the rabbit ligated illeal loop, the difference is more dramatic and clear cut. Significantly however, when LT is exposed to proteolytic enzymes with trypsin-like specificity, the molecule becomes indistinguishable from CT in any biologic assay system (Clements and Finkelstein, 1979; Dickenson and Clements, 1995).

According to Spangler (1992, citations omitted):

"Subunit A is synthesized as a single polypeptide in both *V. cholerae* and *E. coli*. CTA is proteolytically "nicked" between residues 192 and 195 during secretion from the *vibrio* by *V. cholerae* hemagglutinin/protease, giving rise to two polypeptides, A1 (Mr=28,826) and A2 (Mr=5,407), covalently linked through a disulfide bridge between residues 187 and 199. In contrast, LT remains in the *E. coli* periplasm and is not nicked. Introduced into a genetically engineered strain of *V. cholerae*, LT remained unnicked, although it was secreted in the same manner as CT. Proteolytic processing is therefore not a prerequisite for secretion. Purified LTh can, however, be nicked in vitro, suggesting that the mutant *vibrio* used by Hirst et al. contained insufficient soluble hemagglutinin to catalyze nicking, rather than indicating an inability of LTA to be nicked. CT, when introduced via an engineered plasmid into *E. coli*, remains unnicked and cell associated in *E. coli*. Therefore, the defect in processing of CT and LT in *E. coli* is related to the failure of *E. coli* to nick and secrete either toxin. This defect may explain the reduced severity of *E. coli*-induced enteric disease when compared with cholera. In both CT and LT, the disulphide bond linking A1 to A2 remains unreduced and the toxin is therefore essentially inactive, until it enters a cell.

"Both the intact A subunit and the holotoxin are relatively inactive ADP-ribosyltransferases compared with the A1 polypeptide. Catalytic activity requires the reduction of the disulfide bond (A1:Cys-187-A2:Cys-199) linking A1 to A2. The cleavage (nicking) between residues A1-Arg 192 and the start of the A2 polypeptide at A2:Met-195 takes place during secretion of CT from the *vibrio*. tryptic digestion serves the purpose in vitro for LT. Reduction, which releases CTA1 from CTA2, may be accomplished by a variety of agents, usually dithiothreitol or 2-mercaptoethanol in vitro or a thiol: protein oxireductase. The endogenous reducing agent and mechanisms of reduction are not known. An observed time lag of about 16 min between the apparent binding of the toxin to the membrane receptor and the first appearance of the modified substrate intracellularly may be related to the time required for this step to occur following or during insertion or translocation".

LTh stands for LT holoezyme. Thus, if trypsin-treated LT were to be used for transcutaneous immunization, we propose similar mechanisms for disrupting disulphide bonds would occur. This may be shown for trypsin activation of LT in which trypsin-activated LT is similarly potent or of greater potentcy compared to CT and much greater in potency to untreated LT in the mouse Y-1 bioassay (see Dickinson and Clements, 1995).

We propose to activate components of the formulation such as LT using trypsin or similar compounds prior to application the skin to enhance the adjuvant activity and immunogenicity of LT. Activation of LT could also be expected to enhance the immune response to LT as an antigen. The activated adjuvant for transcutaneous immunization is preferably an ADP-ribosylating exotoxin. Optionally, hydration or occlusive dressings may be used in the transcutaneous delivery system in addition to the activation of the adjuvant.

In addition, LT has an unusual affinity for carbohydrate-containing matrices. Specifically, LT binds to an array of biological molecules containing galactose, including glycoproteins and lipopolysaccharides. This lectin-like binding property of LT results in a broader receptor distribution on mammalian cells for LT than for CT, which binds only to GM1. The two molecules also have many immunologic differences, as demonstrated by immunodiffusion studies, against LT-associated *E. coli* diarrhea in volunteers receiving B-subunit whole whole-cell cholera vaccine. LT and CT induce different helper T-cell responses. When used as a mucosal adjuvant, CT selectively induces in some cases Th2-type cells in Peyers patches and spleens as manifested by production of interleukins 4 and 5, but not interleukin 2 or gamma interferon; while LT induces both Th1 and Th2 cells and predominantly antigen-specific IgA responses. Taken together, these findings demonstrate that LT and CT are unique molecules, despite their apparent structural similarities. Such differential behavior makes the ability to activate LT so that it has potency similar to CT useful in manipulating the type of immune response produced to both the toxin itself and to antigens for which LT can be used as an adjuvant. It may also be possible that genetically altered toxoids such as mutants of the trypsin cleavage site may be active by transcutaneous immunication. Such a mutant toxin may be useful as it avoids the risks associated with ingestion or inhaling native toxins.

In a similar manner, PT may be activated to enhance its adjuvant and antigen activities. The S1 subunit of the hexameric PT protein contains the ADP-ribosyltransferase activity while the remaining subunits constitute the B domain. Similar to LT, PT has both trypsin cleavage sites and disulphide binding sites that play a role in association of the S1 subunit with the B oligomer. It is conceivable that activation by trypsin cleavage, disruption of the disulphide bond or both may enhance the adjuvant and antigen activities of PT in the context of transcutaneous immunization. Activation may also take the form of targeting, achieved by disruption of the hexamer into subunits. For example, the PT subunit S3 binds exclusively to the glycolipids of monocytes and could be used to target Langerhans cells in the skin.

Activation of the antigen or adjuvant could be extended to the concept of transcutaneous immunization using DNA by production of a fusion protein comprised of antigen and adjuvant domains. By this method a plasmid encoding an ADP-ribosylating exotoxin such as CT or LT and constructed to express a separate antigen such as a malaria or HIV antigen simultaneously could be placed on the skin in a hydrating solution or occlusive patch, and then taken up by Langerhans cells. Expression of the an ADP-ribosylating exotoxin component of the fusions protein such as CT or LT could activate the Langerhans cell, causing it to migrate and present antigen in the lymph node and thereby induce an immune response to the encoded antigen. Another embodiment could include the conjugation of an adjuvant with a plasmid; an Fc portion of IgG to a plasmid to target APCs. A similar immunization could be achieved using separate plasmids for expressing an ADP-ribosylating exotoxin such as CT or LT and another for expressing the antigen such as a malaria or HIV antigen. It is conceivable that multiple genes on a single construct for multiple antigens could be used or multiple plasmids could be used to simultaneously deliver antigens for multivalent immunization. Plasmids encoding other molecules or compounds such as chemokines (e.g., defensins 1 or 2, RANTES, MIP1-α, MIP-2, interleukin-8) or a cytokine (e.g., interleukin-1β, -2, -6, -10 or -12; γ-interferon; tumor necrosis factor-α; or granulocyte-monocyte-colony stimulating factor) (reviewed in Nohria and Rubin, 1994), a heat shock protein or a derivative, a derivative of *Leishmania major* LeIF (Skeiky et al., 1995), cholera toxin toxin B, a lipopolysaccharide (LPS) derivative (e.g., lipid A or monophosphoryl lipid A), or superantigen (Saloga et al., 1996), or other ADP-ribosylating exotoxins might be delivered with protein antigens.

Other means of activating the transcutaneous adjuvants may be effective, such as adding detergents and phospholipid to the formulation to enhance CT activity by ADP-ribosylation factor (see, for example, Spangler, 1992).

For immunization using adjuvant or antigen activation, modification of the adjuvant or antigen component of the formulation may reduce its effectiveness in parenteral immunization without destroying the utility of the formulation in transcutaneous immunization when the adjuvant and/or antigen is activated. Undesirable properties (e.g., toxicity, allergic reactivity, other side effects) of the adjuvant or antigen in the formulation may be reduced by modification without destroying its effectiveness in transcutaneous immunization. Activation of such modified adjuvant or antigen may involve, for example, removal of a reversible chemical modification (e.g., proteolysis) or a coating which reversibly isolates a component of the formulation from the immune system (i.e., an encapsulated formulation). Alternatively, the adjuvant and/or antigen comprising the formulation may be encapsulated in a particle (e.g., microspheres, nanoparticles). Phagocytosis of a particle may, by itself, enhance activation of an antigen presenting cell by upregulating expression of major histocompatibility antigens and/ or costimulatory molecules (e.g., MHC class II, B7-2).

Antigen

Antigen of the invention may be expressed by recombinant means, preferably as a fusion with an affinity or epitope tag (Summers and Smith, 1987; Goeddel, 1990; Ausubel et al., 1996); chemical synthesis of an oligopeptide, either free or conjugated to carrier proteins, may be used to obtain antigen of the invention (Bodanszky, 1993; Wisdom, 1994). Oligopeptides are considered a type of polypeptide. Oligopeptide lengths of 6 residues to 20 residues are preferred. Polypeptides may also be synthesized as branched structures such as those disclosed in U.S. Pat. Nos. 5,229,490 and 5,390,111. Antigenic polypeptides include, for example, synthetic or recombinant B-cell and T-cell epitopes, universal T-cell epitopes, and mixed T-cell epitopes from one organism or disease and B-cell epitopes from another. Antigen obtained through recombinant means or peptide synthesis, as well as antigen of the invention obtained from natural sources or extracts, may be purified by means of the antigen's physical and chemical characteristics, preferably by fractionation or chromatography (Janson and Ryden, 1989; Deutscher, 1990; Scopes, 1993). A multivalent antigen formulation may be used to induce an immune response to more than one antigen at the same time. Conjugates may be used to induce an immune response to multiple antigens, to boost the immune response, or both. Additionally, toxins may be boosted by the use of toxoids, or toxoids boosted by the use of toxins. Transcutaneous immunization may be used to boost responses induced initially by other routes of immunization such as by oral, nasal or parenteral routes. Antigen includes, for example, toxins, toxoids, subunits thereof, or combinations thereof (e.g., cholera toxin, tetanus toxoid); additionally, toxins, toxoids, subunits thereof, or combinations thereof may act as both antigen and adjuvant.

Antigen may be solubilized in a buffer. Suitable buffers include, but are not limited to, phosphate buffered saline $Ca^{++}/Mg^{++}$ free (PBS), normal saline (150 mM NaCl in water), and Tris buffer. Glycerol may be a suitable non-aqueous buffer for use in the present invention. Antigen may also be in suspension. The detergent may be left in the immunizing solution to enhance penetration.

Hydrophobic antigen can be solubilized in a detergent, for example a polypeptide containing a membrane-spanning domain. Furthermore, for formulations containing liposomes, an antigen in a detergent solution (e.g., a cell membrane extract) may be mixed with lipids, and liposomes then may be formed by removal of the detergent by dilution, dialysis, or column chromatography. See, Gregoriadis (1993). Certain antigens such as, for example, those from a virus (e.g., hepatitis A) need not be soluble per se, but can be incorporated directly into a lipid membrane (e.g., a virosome as described by Morein and Simons, 1985), in a suspension of virion alone, or suspensions of microspheres nanoparticles or heat-inactivated bacteria which may be taken up by and activate antigen presenting cells (e.g., opsonization).

Plotkin and Mortimer (1994) provide antigens which can be used to vaccinate animals or humans to induce an immune response specific for particular pathogens, as well as methods of preparing antigen, determining a suitable dose of antigen, assaying for induction of an immune response, and treating infection by a pathogen (e.g., bacterium, virus, fungus, or parasite).

Bacteria include, for example: anthrax, *campylobacter*, cholera, clostridia, diphtheria, enterotoxigenic *E. coli*, *giardia*, gonococcus, *Helicobacter pylori* or urease produced by *H. pylori* (Lee and Chen, 1994), *Hemophilus influenza* B, *Hemophilus influenza* non-typable, meningococcus, *mycobacterium*, pertussis, pneumococcus, *salmonella, shigella, staphylococcus, Streptococcus B, tetanus, Vibrio cholerae, Borrelia burgdorfi* and *Yersinia*; and products thereof.

Viruses include, for example: adenovirus, dengue serotypes 1 to 4 (Delenda et al., 1994; Fonseca et al., 1994; Smucny et al., 1995), ebola (Jahrling et al., 1996), enterovirus, hanta virus, hepatitis serotypes A to E (Blum, 1995; Katkov, 1996; Lieberman and Greenberg, 1996; Mast, 1996; Shafara et al., 1995; Smedila et al., 1994; U.S. Pat. Nos. 5,314,808 and 5,436,126), herpes simplex virus 1 or 2, human immunodeficiency virus (Deprez et al., 1996), human papilloma virus, influenza, measles, Norwalk, Japanese equine encephalitis, papilloma virus, parvovirus B19, polio, rabies, respiratory syncytial virus, rotavirus, rubella, rubeola, St. Louis encephalitis, vaccinia, vaccinia constructs containing genes coding for other antigens such as malaria antigens, varicella, and yellow fever; and products thereof.

Parasites include, for example: *Entamoeba histolytica* (Zhang et al., 1995); *Plasmodium* (Bathurst et al., 1993; Chang et al., 1989, 1992, 1994; Fries et al., 1992a, 1992b; Herrington et al., 1991; Khusmith et al., 1991; Malik et al., 1991; Migliorini et al., 1993; Pessi et al., 1991; Tam, 1988; Vreden et al., 1991; White et al., 1993; Wiesmueller et al., 1991), *Leishmania* (Frankenburg et al., 1996), and the Helminthes; and products thereof.

Other viruses which can be used in the present invention are disclosed in Gordon, 1997 and include, for example, Adenovirus (respiratory disease), Coronavirus (respiratory and enteric disease), Cytomegalovirus (mononucleosis), Dengue virus (dengue fever, shock syndrome), Epstein-Barr virus (mononucleosis, Burkitt's lymphoma), Hepatitis A, B and C virus (liver disease), Herpes simplex virus type 1 (encephalitis, stomatitis), Herpes simplex virus type 2 (genital lesions), Human herpesvirus-6 (unknown, possibly Kaposi's sarcoma), Human immunodeficiency virus types 1 and 2 (acquired immunodeficiency syndrome-AIDS), Human T-cell lymphotropic virus type 1 (T-cell leukemia), Influenza A, B, and C (respiratory disease), Japanese encephalitis virus (pneumonia, encephalopathy), Measles virus (subacute sclerosing panencephalitis), Mumps virus (meningitis, encephalitis), Papillomavirus (warts, cervical carcinoma), Parvovirus (respiratory disease, anemia), Poliovirus (paralysis), Polyomavirus JC (multifocal leukoencephalopathy), Polyomavirus BK (hemorrhagic cystitis), Rabies virus (nerve dysfunction), Respiratory syncytial virus (respiratory disease), Rhinovirus (common cold), Rotavirus (diarrhea), Rubella virus (fetal malformations), Vaccinia virus (generalized infection), Yellow fever virus (jaundice, renal and hepatic failure), Varicella zoster virus (chickenpox).

Other bacteria which can be used in the present invention are disclosed in Gordon, 1997 and include, for example, *Bacillus anthracis* (anthrax); *Bordetella pertussis* (whooping cough), *Borrelia burgdorferi* (lyme disease), *Campylobacter jejuni* (gastroenteritis), *Chlamydia trachomatis* (pelvic inflammatory disease, blindness), *Clostridium botulinum* (botulism), *Corynebacterium* dipththeriae (diphtheria), *Escherichia coli* (diarrhea, urinary tract infections), *Haemophilus influenzae* (pneumonia), *Helicobacter pylori* (gastritis, duodenal ulcer), *Legionella pneumophila* (Legionnaires' disease), *Listeria monocytogenes* (meningitis, sepsis), *Mycobacterium leprae* (leprosy), *Mycobacterium tuberculosis* (tuberculosis), *Neisseria gonorrhoeae* (gonorrhea), *Neisseria meningitidis* (sepsis, meningitis), *Pseudomonas aeruginosa* (nosocomial infections), *Pseudomonas aeruginosa* (nosocomial infections), *Rickettsia* (Rocky Mountain spotted fever), *Salmonella* (typhoid fever, gastroenteritis), *Shigella* (dysentery), *Staphylococcus aureus* (impetigo, toxic shock syndrome), *Streptococcus pneumoniae* (pneumonia, otitis media), *Streptococcus pyogenes* (Rheumatic fever, pharyngitis), *Treponema pallidum* (syphilis), *Vibrio cholerae* (cholera), *Yersinia pestis* (bubonic plague).

Other parasites which can be used in the present invention are disclosed in Gordon, 1997 and include, for example, African trypanosomes (trypanosomiasis), *Entamoeba histolytica* (amebic dysentery), *Giardia lamblia* (diarrheal disease), *Leishmania* (lesions of the spleen, tropical sores), *Plasmodium* (malaria), Microfilariae (filariasis), Schistosomes (schistosomiasis), *Toxoplasma gondii* (toxoplasmosis), *Trichomonas vaginalis* (vaginitis), *Trypanosoma cruzi* (Chagas disease).

Fungi which can be used in the present invention are disclosed in Gordon, 1997 and include, for example, *Candida albicans* (mucosal infections), *Histoplasma* (lung, lymph node infections), *Pneumocystis carinii* (pneumonia in AIDS), *Aspergillus fumigatis* (aspergillosis).

Adjuvant

The formulation also contains an adjuvant, although a single molecule may contain both adjuvant and antigen properties (e.g., cholera toxin) (Elson and Dertzbaugh, 1994). Adjuvants are substances that are used to specifically or non-specifically potentiate an antigen-specific immune response. Usually, the adjuvant and the formulation are mixed prior to presentation of the antigen but, alternatively, they may be separately presented within a short interval of time.

Adjuvants are usually products of bacteria, parasites or even viruses or bacteria, but may be derived from other natural or synthetic sources. Adjuvants include, for example, an oil emulsion (e.g., complete or incomplete Freund's adjuvant), a chemokine (e.g., defensins 1 or 2, RANTES, MIP1-α, MIP-2, interleukin-8) or a cytokine (e.g., interleukin-1β, -2, -6, -10 or -12; γ-interferon; tumor necrosis factor-α; or granulocyte-monocyte-colony stimulating factor) (reviewed in Nohria and Rubin, 1994), a muramyl dipeptide derivative (e.g., murabutide, threonyl-MDP or muramyl tripeptide), a heat shock protein or a derivative, a derivative of *Leishmania major* LeIF (Skeiky et al., 1995), cholera toxin or cholera toxin B, bARES, a lipopolysaccharide (LPS) derivative (e.g., lipid A or monophosphoryl lipid A, synthetic lipid A analogues), or superantigen (Saloga et al., 1996) block copolymers or other polymers known in the art. Also, see Richards et al. (1995) for other adjuvants useful in immunization.

An adjuvant may be chosen to preferentially induce antibody or cellular effectors, specific antibody isotypes (e.g., IgM, IgD, IgA1, IgA2, secretory IgA, IgE, IgG1, IgG2, IgG3, and/or IgG4), or specific T-cell subsets (e.g., CTL, Th1, Th2 and/or $T_{DTH}$) (Munoz et al., 1990; Glenn et al., 1995).

CpGs are among a class of structures which have patterns allowing the immune system to recognize their pathogenic origins to stimulate the innate immune response leading to adaptive immune responses (Medzhitov and Janeway, 1997). These structures are called pathogen-associated molecular patterns (PAMPs) and include lipopolysaccharides, teichoic acids, unmethylated CpG motifs, double stranded RNA and mannins, for example.

PAMPs induce endogenous danger signals that can enhance the immune response, act as costimulators of T-cell function and control the effector function. The ability of PAMPs to induce these responses play a role in their potential as adjuvants and their targets are APCs such as macrophages and dendritic cells. The antigen presenting cells of the skin could likewise be stimulated by PAMPs transmitted through the skin. For example, Langerhans cells, a type of dendritic cell, could be activated by a PAMP in solution on the skin with a transcutaneously poorly immunogenic molecule and be induced to migrate and present this poorly immunogenic molecule to T-cells in the lymph node, inducing an antibody response to the poorly immunogenic molecule. PAMPs could also be used in conjunction with other skin adjuvants such as cholera toixn to induce different costimulatory molecules and control different effector functions to guide the immune response, for example from a Th2 to a Th1 response.

Cholera toxin is a bacterial exotoxin from the family of ADP-ribsoylating exotoxins (referred to as bAREs). Most bAREs are organized as A:B dimer with a binding B subunit and an A subunit containing the ADP-ribosyltransferase. Such toxins include diphtheria, *Pseudomonas* exotoxin A, cholera toxin (CT), *E. coli* heat-labile enterotoxin (LT), pertussis toxin (PT), *C. botulinum* toxin C2, *C. botulinum* toxin C3, *C. limosum* exoenzyme, *B. cereus* exoenzyme, *Pseudomonas* exotoxin S, *Staphylococcus aureus* EDIN, and *B. sphaericus* toxin.

Cholera toxin is an example of a bARE that is organized with A and B subunits. The B subunit is the binding subunit and consists of a B-subunit pentamer which is non-covalently bound to the A subunit. The B-subunit pentamer is arranged in a symmetrical doughnut-shaped structure that binds to GM1-ganglioside on the target cell. The A subunit serves to ADP ribosylate the alpha subunit of a subset of the hetero trimeric GTP proteins (G proteins) including the Gs protein which results in the elevated intracellular levels of cyclic AMP. This stimulates release of ions and fluid from intestinal cells in the case of cholera.

Cholera toxin (CT) and its B subunit (CTB) have adjuvant properties when used as either an intramuscular or oral immunogen (Elson and Dertzbaugh, 1994; Trach et al., 1997). Heat-labile enterotoxin from *E. coli* (LT) is 75-77% homologous at the amino acid level with CT and possesses similar binding properties; it also appears to bind the GM1-ganglioside receptor in the gut and has similar ADP-ribosylating exotoxin activities. Another bARE, *Pseudomonas* exotoxin A (ETA), binds to the α2-macroglobulin receptor-low density lipoprotein receptor-related protein (Kounnas et al., 1992). bAREs are reviewed by Krueger and Barbieri (1995). CT, CTB, LT, ETA and PT, despite having different cellular binding sites, are potent adjuvants for transcutaneous immunization, inducing high levels of IgG antibodies but not IgE antibodies. CTB without CT can also induce high levels of IgG antibodies. Thus, both bAREs and a derivative thereof can effectively immunize when epicutaneouly applied to the skin in a simple solution.

All licensed vaccines require a level of antibody for approval—no other immune component such as T-cell proliferation is used. Protection against the life-threatening infections diphtheria, pertussis, and tetanus (DPT) can be achieved by inducing high levels of circulating anti-toxin antibodies. Pertussis may be an exception in that some investigators feel that antibodies directed to other portions of the invading organism are necessary for protection, although this is controversial (see Schneerson et al., 1996) and most new generation acellular pertussis vaccines have PT as a component of the vaccine (Krueger and Barbieri, 1995). The pathologies in the diseases caused by DPT are directly related to the effects of their toxins and anti-toxin antibodies most certainly play a role in protection (Schneerson et al., 1996).

In general, toxins can be chemically inactivated to form toxoids which are less toxic but remain immunogenic. We envision that the one embodiment of transcutaneous immunization system will use toxin-based immunogens and adjuvants to achieve anti-toxin levels adequate for protection against these diseases. The anti-toxin antibodies may be induced through immunization with the toxins, or genetically-detoxified toxoids themselves, or with toxoids and adjuvants such as CT. Genetically toxoided toxins which have altered ADP-ribosylating exotoxin activity, or trypsin cleavage site mutations or other mutations are envisioned to be especially useful as non-toxic activators of antigen presenting cells used in transcutaneous immunization. Mutants based on inactivating the catalytic activity of the ADP-ribosyl transferase by genetic deletion retain the binding capabilities, but lack the toxicity, of the natural toxins. This approach is described by Burnette et al. (1994), Rappuoli et al. (1995), and Rappuoli et al. (1996). Such genetically toxoided exotoxins could be useful for transcutaneous immunization system in that they would not create a safety concern as the toxoids would not be considered toxic. There are other genetically altered toxins which have, for example, deletions of the trysin cleavage site and use both non-toxic and immunogeneric on the skin. However, activation through a technique such as trypsin cleavage would be expected to enhance the adjuvant qualities of LT through the skin which is lacking inherent trypsin enzymes. Additionally, several techniques exist to chemically toxoid toxins which can address the same problem (Schneerson et al., 1996). These techniques could be important for certain applications, especially pediatric applications, in which ingested toxins (e.g., diphtheria toxin) might possibly create adverse reactions.

Optionally, an activator of Langerhans cells may be used as an adjuvant. Examples of such activators include: an inducer of heat shock protein; contact sensitizer (e.g., trinitrochlorobenzene, dinitrofluorobenzene, nitrogen mustard, pentadecylcatechol); toxin (e.g., Shiga toxin, Staph enterotoxin B); lipopolysaccharide, lipid A, or derivatives thereof; bacterial DNA (Stacey et al., 1996); cytokine (e.g., tumor necrosis factor-α, interleukin-1β, -10, -12); calcium ions in solution; calcium ionophores, and chemokine (e.g., defensins 1 or 2, RANTES, MIP-1α, MIP-2, interleukin-8).

If an immunizing antigen has sufficient Langerhans cell activating capabilities then a separate adjuvant may not be required, as in the case of CT which is both antigen and adjuvant. It is envisioned that whole cell preparations, live viruses, attenuated viruses, DNA plasmids, and bacterial DNA could be sufficient to immunize transcutaneously then an adjuvant is present. It may be possible to use low concentrations of contact sensitizers or other activators of Langerhans cells to induce an immune response without inducing skin lesions.

Practical Aspects of Transcutaneous Immunization

Efficient immunization can be achieved with the present invention because transcutaneous delivery of antigen may target the Langerhans cell. These cells are found in abundance in the skin and are efficient antigen presenting cells leading to T-cell memory and potent immune responses. Because of the presence of large numbers of Langerhans cells in the skin, the efficiency of transcutaneous delivery may be related to the surface area exposed to antigen and adjuvant. In fact, the reason that transcutaneous immunization is so efficient may be that it targets a larger number of these efficient antigen presenting cells than intramuscular immunization.

We envision the present invention will enhance access to immunization, while inducing a potent immune response. Because transcutaneous immunization does not involve physical penetration of the skin and the complications and difficulties thereof, the requirements of trained personnel, sterile technique, and sterile equipment are reduced. Furthermore, the barriers to immunization at multiple sites or to multiple immunizations are diminished. Immunization by a single application of the formulation is also envisioned, but boosting is generally needed. Needle free immunization is a priority for the World Health Organization (WHO) because of the reuse of needles which causes needle-borne disease.

Immunization may be achieved using epicutaneous application of a simple solution of antigen and adjuvant impregnated in gauze under an occlusive patch, or by using other patch technologies; creams, gels, immersion, ointments and sprays are other possible methods of application. The immunization could be given by untrained personnel, and is amenable to self-application. Large-scale field immunization could occur given the easy accessibility to immunization. Additionally, a simple immunization procedure would improve access to immunization by pediatric patients and the elderly, and populations in Third World countries.

For previous vaccines, their formulations were injected through the skin with needles. Injection of vaccines using needles carries certain drawbacks including the need for sterile needles and syringes, trained medical personnel to administer the vaccine, discomfort from the injection, and potential complications brought about by puncturing the skin with the needle. Immunization through the skin without the use of needles (i.e., transcutaneous immunization) represents a major advance for vaccine delivery by avoiding the aforementioned drawbacks.

Moreover, transcutaneous immunization may be superior to immunization using needles as more immune cells would be targeted by the use of several locations targeting large surface areas of skin. A therapeutically effective amount of antigen sufficient to induce an immune response may be delivered transcutaneously either at a single cutaneous location, or over an area of intact skin covering multiple draining lymph node fields (e.g., cervical, axillary, inguinal, epitrochelear, popliteal, those of the abdomen and thorax). Such locations close to numerous different lymphatic nodes at locations all over the body will provide a more widespread stimulus to the immune system than when a small amount of antigen is injected at a single location by intradermal subcutaneous or intramuscular injection.

Antigen passing through or into the skin may encounter antigen presenting cells which process the antigen in a way that induces an immune response. Multiple immunization sites may recruit a greater number of antigen presenting cells and the larger population of antigen presenting cells that were recruited would result in greater induction of the immune response. It is conceivable that absorption through the skin may deliver antigen to phagocytic cells of the skin such as, for example, dermal dendritic cells, macrophages, and other skin antigen presenting cells; antigen may also be delivered to phagocytic cells of the liver, spleen, and bone marrow that are known to serve as the antigen presenting cells through the blood stream or lymphatic system. Langerhans cells, dendritic cells, and macrophages may be specifically targeted using Fc receptor conjugated to or recombinantly produced as a protein fusion with adjuvant; also, complement receptors (C3, C5) may be conjugated to or recombinantly produced as a protein fusion with protein A or protein G to target surface immunoglobulin of B cells. The result would be targeted distribution of antigen to antigen presenting cells to a degree that is rarely, if ever achieved, by current immunization practices.

The transcutaneous immunization system may be applied directly to the skin and allowed to air dry; rubbed into the skin or scalp; held in place with a dressing, patch, or absorbent material; immersion; otherwise held by a device such as a stocking, slipper, glove, or shirt; or sprayed onto the skin to maximize contact with the skin. The formulation may be applied in an absorbant dressing or gauze. The formulation may be covered with an occlusive dressing such as, for example, AQUAPHOR (an emulsion of petrolatum, mineral oil, mineral wax, wool wax, panthenol, bisabol, and glycerin from Beiersdorf, Inc.), plastic film, COMFEEL (Coloplast) or vaseline; or a non-occlusive dressing such as, for example, DUODERM (3M) or OPSITE (Smith & Napheu). An occlusive dressing completely excludes the passage of water. The formulation may be applied to single or multiple sites, to single or multiple limbs, or to large surface areas of the skin by complete immersion. The formulation may be applied directly to the skin.

Genetic immunization has been described in U.S. Pat. Nos. 5,589,466, 5,593,972, and 5,703,055. The nucleic acid(s) contained in the formulation may encode the antigen, the adjuvant, or both. It would generally be expected that the immune response would be enhanced by the coadministration of an adjuvant, for example, CT, LT or CpGs to the nucleic acid encoding for the antigen. The nucleic acid may or may not be capable of replication; it may be non-integrating and non-infectious. For example, the nucleic acid may encode a fusion polypeptide comprising antigen and a ubiquitin domain to direct the immune response to a class I restricted response. The nucleic acid may further comprise a regulatory region (e.g., promoter, enhancer, silencer, transcription initiation and termination sites, RNA splice acceptor and donor sites, polyadenylation signal, internal ribosome binding site, translation initiation and termination sites) operably linked to the sequence encoding the antigen. The nucleic acid may be complexed with an agent that promotes transfection such as cationic lipid, calcium phosphate, DEAE-dextran, polybrene-DMSO, or a combination thereof; also, immune cells can be targeted by conjugation of DNA to Fc receptor or protein A/G, or encapsulating DNA in an agent linked to Fc receptor or protein A/G. The nucleic acid may comprise regions derived from viral genomes. Such materials and techniques are described by Kriegler (1990) and Murray (1991).

An immune response may comprise humoral (i.e., antigen-specific antibody) and/or cellular (i.e., antigen-specific lymphocytes such as B cells, CD4$^+$ T cells, CD8$^+$ T cells, CTL, Th1 cells, Th2 cells, and/or $T_{DTH}$ cells) effector arms. Moreover, the immune response may comprise NK cells that mediate antibody-dependent cell-mediated cytotoxicity (ADCC).

The immune response induced by the formulation of the invention may include the elicitation of antigen-specific antibodies and/or cytotoxic lymphocytes (CTL, reviewed in Alving and Wassef, 1994). Antibody can be detected by immunoassay techniques, and the detection of various isotypes (e.g., IgM, IgD, IgA1, IgA2, secretory IgA, IgE, IgG1, IgG2, IgG3, or IgG4) may be expected. An immune response can also be detected by a neutralizing assay. Antibodies are protective proteins produced by B lymphocytes. They are highly specific, generally targeting one epitope of an antigen. Often, antibodies play a role in protection against disease by specifically reacting with antigens derived from the pathogens causing the disease.

CTLs are particular protective immune cells produced to protect against infection by a pathogen. They are also highly specific. Immunization may induce CTLs specific for the antigen, such as a synthetic oligopeptide based on a malaria protein, in association with self-major histocompatibility antigen. CTLs induced by immunization with the transcutaneous delivery system may kill pathogen infected cells. Immunization may also produce a memory response as indicated by boosting responses in antibodies and CTLs, lymphocyte proliferation by culture of lymphocytes stimulated with the antigen, and delayed type hypersensitivity responses to intradermal skin challenge of the antigen alone.

In a viral neutralization assay, serial dilutions of sera are added to host cells which are then observed for infection after challenge with infectious virus. Alternatively, serial dilutions of sera may be incubated with infectious titers of virus prior to innoculation of an animal, and the innoculated animals are then observed for signs of infection.

The transcutaneous immunization system of the invention may be evaluated using challenge models in either animals or humans, which evaluate the ability of immunization with the antigen to protect the subject from disease. Such protection would demonstrate an antigen-specific immune response. In lieu of challenge, for example achieving antidiphtheria antibody titers of 5 IU/ml or greater is generally assumed to indicate optimum protection and serves as a surrogate marker for protection (Plotkin and Mortimer, 1994).

Vaccination has also been used as a treatment for cancer and autoimmune disease. For example, vaccination with a tumor antigen (e.g., prostate specific antigen) may induce an immune response in the form of antibodies, CTLs and lymphocyte proliferation which allows the body is immune system to recognize and kill tumor cells. Tumor antigens useful for vaccination have been described for melanoma (U.S. Pat. Nos. 5,102,663, 5,141,742, and 5,262,177), prostate carcinoma (U.S. Pat. No. 5,538,866), and lymphoma (U.S. Pat. Nos. 4,816,249, 5,068,177, and 5,227,159). Vaccination with T-cell receptor oligopeptide may induce an immune response that halts progression of autoimmune disease (U.S. Pat. Nos. 5,612,035 and 5,614,192; Antel et al., 1996; Vandenbark et al., 1996). U.S. Pat. No. 5,552,300 also describes antigens suitable for treating autoimmune disease.

The following is meant to be illustrative of the present invention; however, the practice of the invention is not limited or restricted in any way by the examples.

EXAMPLES

Immunization procedure. Twenty four hours prior to immunization, the back of the mouse is shaved from the distal aspect of the scapula to 0.5 cm above the base of the tail. In the case of C57BL/6 mice, the animals are lightly anesthetized (40 mg/kg ketamine:4 mg/kg xylazine mixture in saline) prior to shaving. On the day of immunization the animals are immunized with 0.04 ml of an anesthesia mixture (2.3 mL sterile saline (Sigma): 5 mL ketamine (100 mg/mL, Parke-Davis): 0.5 mL xylazine (100 mg/mL, Phoenix Pharmaceuticals)) which delivers a final dose of approximately 110 mg/kg ketamine and 11 mg/kg xylazine. For procedures requiring alcohol swabbing, the back is wiped 10× (5× sweeping up the back towards the head, flip over alcohol pad and sweep back 5× more) using an isopropyl pad. The alcohol is allowed to evaporate for 5 minutes. Hydration of the back is accomplished by gently rubbing the back with a sterile water-saturated gauze pad so as to form a pool of water on the back. After a 5 minute hydration period, the back is blotted dry with a dry gauze pad. Next, antigen—generally $\leq 100$ μg of antigen and adjuvant in 100 μl final volume, is applied to the back using a pipette and tip and left on the skin for 60 to 120 minutes. After the defined immunization period has been reached, any excess solution in the immunized area is blotted with cotton gauze. The animals are then rinsed animals under a slow steady stream of lukewarm tap water for 10 seconds to remove any excess antigen, blotted dry and the rinsing procedure repeated. The cages are then placed onto the heating pads until they are fully recovered from the anesthesia.

Measurement of Human anti-LT Antibody Titers. Anti-LT IgG titers were determined as previously described (Svennerholm A-M., Holmgren, J., Black, R., Levine, M. & Merson, M. Serologic differentiation between antitoxin responses to infection with *Vibrio cholerae* and enterotoxin-producing *Escherichia coli*. J. Infect. Dis. 147, 541-522 (1983). 96 well (Type-Russell) plates were coated overnight with monosialoganglioside-$G_{M1}$ (Sigma, St. Louis, Mo.) of LT (Sigma), blocked with 5% dry milk in PBS-0.05% Tween. Responses were detected using goat anti-human IgG(γ)-HRP (Kirkegaard and Perry, Gaithersburg, Md., and 2,2'-azino-di[3-ethylbenzthiazoline sulfonate (Kirkegaard and Perry) as substrate and plates were read at 405 nm. Results are reported in ELISA units (EU) which are defined as the inverse dilution of sample which yields an OD of 1.0. Anti-LT IgA was determined in the same manner as anti-LT IgG except that goat anti-human IgA(α)-HRP (Kirkegaard and Perry) was used as secondary antibody and ODs were plotted against a standard IgA curve yielding results expressed in ng/ml. The standard IgA curve and total serum IgA were determined by using unlabeled goat anti-human IgA (Kirkegaard and Perry) followed by blocking as above and then application of serial dilutions of IgA standard Example 1

Swabbing the skin with a treated or untreated swab is thought to physically and chemically remove a small portion of the stratum corneum and thus enhance skin penetration. Swabs can be made of materials such as, for example, cotton, nylon, rayon and polyethylene. Alcohol swabbing is thought to remove a small portion of the stratum corneum and acts both as a physical means and chemical means of penetration enhancement. In the example above, the enhancement of the immune response to transcutaneous immunization can be seen with this penetration enhancement method. BALB/c mice 6 to 8 weeks of age were anesthetized and shaved as described in the "immunization procedure". Twenty four hours later, the backs of the animals were either wiped with a gauze pad saturated in water "water" or wiped for approximately 10 seconds with an alcohol prep pad containing 70% isopropyl alcohol "isopropanol". The alcohol was allowed to evaporate for approximately 5 minutes. The excess water was removed from the backs of the "water" group by blotting. All animals were then treated with 20 μg of CT (100 μl of a 0.2 mg/ml solution). Removal of excess antigen was conducted as described in the "immunization procedure."

The anti-CT antibody titers were determined using ELISA as described above for "ELISA IgG (H+L)" 3 weeks after a single immunization. The results are shown in Table 1. While CT was clearly immunogenic in both groups, the group treated with the alcohol prep pads exhibited a geometric mean titer that was 6 fold higher and the individual titers were more consistent than the "water" animals. Thus it appears that chemical and physical disruption of the skin surface with alcohol swabs enhances delivery of antigen by the transcutaneous route.

TABLE 1

Enhancement of transcutaneous immunization by chemical penetration enhancement: Anti-CT titers in mice that had the skin treated with an alcohol prep pad before application of the antigen.

| | | anti-CT IgG (H + L) ELISA units | |
|---|---|---|---|
| Animal # | treatment | prebleed | week 3 |
| 7146 | water | | 1275 |
| 7147 | water | | 69 |
| 7148 | water | | 7420 |
| 7149 | water | | 6025 |
| 7150 | water | | 388 |
| geometric mean | | | 1088 |
| pooled prebleed | | 7 | |
| 7161 | isopropanol | | 3100 |
| 7162 | isopropanol | | 14797 |
| 7163 | isopropanol | | 6670 |
| 7164 | isopropanol | | 7426 |
| 7165 | isopropanol | | 7024 |
| geometric mean | | | 6928 |
| pooled prebleed | | 7 | |

Example 2

To assess whether chemical penetration enhancement alone might augment transcutaneous immunization a detergent was used on the skin. BALB/c mice 6 to 8 weeks of age were anesthetized and shaved as described in the "immunization procedure." Twenty-four hours later, the backs of the "water" group were wiped with a gauze pad saturated in water and a pool of water was placed on the back. Approximately 5 minutes later, any excess water was removed and 25 μg of CT (50 μl of a 0.5 mg/ml solution) was applied to the back. Alternatively, 24 hours after shaving, the backs of the "5% SDS" group were treated by dripping 300 μl of 5% SDS (Sodium Dodecyl Sulfate—a 1 to 1 mixture of deionized water and commercial stock of 10% SDS), a detergent, for approximately 12 minutes followed by blotting off any excess SDS with a dry gauze pad. SDS can be applied to the skin in a carrier such as, for example, a pad and then any excess SDS can be removed with a dry gauze pad. Thereafter the animals were hydrated and immunized as per the "water" group. Removal of excess antigen was conducted as described in the "immunization procedure."

The anti-CT antibody titers were determined using ELISA as described above for "ELISA IgG (H+L)" 2 weeks after a single immunization. The results are shown in tables 2a and 2b. While CT was clearly immunogenic in both groups, the geometric mean titer in the 5% SDS treated group approximately 2 fold higher and the titers were more consistent among the latter animals as compared with the "water" animals. Thus it appears that chemical disruption of the skin surface with detergent (5% SDS) enhances delivery of antigen by the transcutaneous route.

TABLE 2a

Enhancement of transcutaneous immunization by chemical penetration enhancement: Anti-CT titers in mice that had the skin treated with detergent (5% SDS) before application of the antigen.

| | | anti-CT IgG (H + L) ELISA units | |
|---|---|---|---|
| Animal # | treatment | prebleed | week 2 |
| 546 | water | | 4629 |
| 547 | water | | 3154 |
| 548 | water | | 7288 |
| 549 | water | | 1719 |
| 550 | water | | 11779 |
| geometric mean | | | 3678 |
| pooled prebleed | | 5 | |
| 596 | 5% SDS | | 6945 |
| 597 | 5% SDS | | 2244 |
| 598 | 5% SDS | | 8604 |
| 599 | 5% SDS | | 7093 |
| 600 | 5% SDS | | 12583 |
| geometric mean | | | 5553 |
| pooled prebleed | | 1 | |

TABLE 2b

Enhancement of transcutaneous immunization by chemical penetration enhancement: Anti-CT titers in mice that had the skin treated with detergent (5% SDS) before application of the antigen.

| | | anti-CT IgG (H + L) ELISA units | |
|---|---|---|---|
| Animal # | treatment | prebleed | week 3 |
| 546 | water | | 22525 |
| 547 | water | | 8939 |
| 548 | water | | 11885 |
| 549 | water | | 5121 |
| 550 | water | | 37770 |
| geometric mean | | | 10521 |
| pooled prebleed | | 11 | |
| 596 | 5% SDS | | 102387 |
| 597 | 5% SDS | | 6597 |
| 598 | 5% SDS | | 47245 |
| 599 | 5% SDS | | 45565 |
| 600 | 5% SDS | | 38413 |
| geometric mean | | | 34725 |
| pooled prebleed | | 6 | |

Example 3

Another form of chemical penetration enhancement, a depilatory (such as, for example, calcium hydroxide or the like) is widely used in dermatologic experiments and was shown to enhance transcutaneous immunization. BALB/c mice 6 to 8 weeks of age were anesthetized and shaved as described in the "immunization procedure." Twenty-four hours later, the backs of the "water" group were wiped with a gauze pad saturated in water and a pool of water was placed on the back. Approximately 5 minutes later, any excess water was removed and 25 µg of CT (50 µl of a 0.5 mg/ml solution) was applied to the back. Alternatively, twenty-four hours after shaving, the backs of the "nair©" group were treated with 100 µl of nair© cream for approximately 12 minutes followed by wiping off of the formulation with a gauze pad saturated in water. Such treatment can continue for from about 0.1 to 30 minutes preferably about 20 minutes and more preferably about 12 minutes. Thereafter the animals were hydrated and immunized as per the "water" group. Removal of excess antigen was conducted as described in the "immunization procedure."

The anti-CT antibody titers were determined using ELISA as described above for "ELISA IgG (H+L)" 2 weeks after a single immunization. The results are shown in tables 3a and 3b. While CT was clearly immunogenic in both groups, the geometric mean titer in the nair treated group was 3 fold higher and the titers were more consistent among the latter animals as compared with the "water" animals. Thus it appears that chemical disruption of the skin surface with calcium hydroxide, the active ingredient in nair© cream, enhances delivery of antigen by the transcutaneous route.

TABLE 3a

Enhancement of transcutaneous immunization by chemical penetration enhancement: Anti-CT titers in mice that had the skin treated with calcium hydroxide (nair ©) before application of the antigen.

| | anti-CT IgG (H + L) ELISA units | | |
|---|---|---|---|
| Animal # | treatment | prebleed | week 2 |
| 546 | water | | 4629 |
| 547 | water | | 3154 |
| 548 | water | | 7288 |
| 549 | water | | 1719 |
| 550 | water | | 11779 |
| geometric mean | | | 3678 |
| pooled prebleed | | 5 | |
| 581 | nair © | | 17621 |
| 582 | nair © | | 12261 |
| 583 | nair © | | 7235 |
| 584 | nair © | | 7545 |
| 585 | nair © | | 5997 |
| geometric mean | | | 10421 |
| pooled prebleed | | 4 | |

TABLE 3b

Enhancement of transcutaneous immunization by chemical penetration enhancement: Anti-CT titers in mice that had the skin treated with calcium hydroxide (nair ©) before application of the antigen.

| | anti-CT IgG (H + L) ELISA units | | |
|---|---|---|---|
| Animal # | treatment | prebleed | Week 3 |
| 546 | water | | 22525 |
| 547 | water | | 8939 |
| 548 | water | | 11885 |
| 549 | water | | 5121 |
| 550 | water | | 37770 |
| geometric mean | | | 10521 |
| pooled prebleed | | 11 | |
| 581 | nair © | | 34222 |
| 582 | nair © | | 45674 |
| 583 | nair © | | 50224 |
| 584 | nair © | | 27270 |
| 585 | nair © | | 21832 |

TABLE 3b-continued

Enhancement of transcutaneous immunization by chemical penetration enhancement: Anti-CT titers in mice that had the skin treated with calcium hydroxide (nair ©) before application of the antigen.

| | anti-CT IgG (H + L) ELISA units | | |
|---|---|---|---|
| Animal # | treatment | prebleed | Week 3 |
| geometric mean | | | 38251 |
| pooled prebleed | | 15 | |

Example 4

Further studies were conducted to evaluate the effect of chemical penetration enhancement using a keratinolytic formulation (such as a salicylate). BALB/c mice 6 to 8 weeks of age were anesthetized and shaved as described in the "immunization procedure." Twenty-four hours later, the backs of the "water" group were wiped with a gauze pad saturated in water and a pool of water was placed on the back. Approximately 5 minutes later, any excess water was removed and 25 µg of CT (50 µl of a 0.5 mg/ml solution) was applied to the back. Alternatively, twenty-four hours after shaving, the backs of the "salicylate/water" group were treated with a gauze pad saturated with a 10% salicylate suspension (1 tablet (325 mg) Certified brand aspirin dissolved in 3.25 ml deionized water). Such treatment can continue for from about 0.1 to 30 minutes preferably about 20 minutes and more preferably about 10 minutes. Approximately 10 minutes later any remaining solution was blotted off, the backs of the animals were hydrated with water for 5 minutes, followed by removal of excess water, and then topical application of 25 µg of CT. Removal of excess antigen was conducted as described in the "immunization procedure."

The anti-CT antibody titers were determined using ELISA as described above for "ELISA IgG (H+L)" 2 weeks after a single immunization. The results are shown in Table 4. While CT was clearly immunogenic in both groups, the geometric mean titer in the salicylate treated group was 4 fold higher and the titers were more consistent among the latter animals as compared with the "water" animals. Thus it appears that chemical disruption of the skin surface with salicylate enhances delivery of antigen by the transcutaneous route.

TABLE 4

Enhancement of transcutaneous immunization by chemical penetration enhancement: Anti-CT titers in mice that had the skin treated with salicylate (aspirin) before application of the antigen.

| | anti-CT IgG (H + L) ELISA units | | |
|---|---|---|---|
| Animal # | treatment | prebleed | week 2 |
| 741 | water | | 272 |
| 742 | water | | not available |
| 743 | water | | 456 |
| 744 | water | | 443 |
| 745 | water | | 1395 |
| geometric mean | | | 526 |
| pooled prebleed | | 7 | |
| 756 | salicylate/water | | 2279 |
| 757 | salicylate/water | | 4581 |
| 758 | salicylate/water | | 4658 |
| 759 | Salicylate/water | | 2771 |
| 760 | Salicylate/water | | 593 |

TABLE 4-continued Enhancement of transcutaneous immunization by chemical penetration enhancement: Anti-CT titers in mice that had the skin treated with salicylate (aspirin) before application of the antigen.

| | anti-CT IgG (H + L) ELISA units | | |
|---|---|---|---|
| Animal # | treatment | prebleed | week 2 |
| geometric mean | | | 2402 |
| pooled prebleed | | 36 | |

Example 5

To assess the role of physical/mechanical penetration enhancement, an abrasive, in the form of a common emory board, was used to remove a portion of the stratum corneum. BALB/c mice 6 to 8 weeks of age were anesthetized and shaved as described in the "immunization procedure." Twenty four hours later, the backs of the animals were either wiped with a gauze pad saturated in water "water" or brushed 10 times with a medium grain emory board "emory board." and then wiped with a gauze pad saturated in water Approximately five minutes after the water treatment, any excess water was removed and 20 µg of CT (100 µl of a 0.2 mg/ml) solution applied to the back. Removal of excess antigen was conducted as described in the "immunization procedure."

The anti-CT antibody titers were determined using ELISA as described above for "ELISA IgG (H+L)" 3 weeks after a single immunization. The results are shown in Table 5. While CT was clearly immunogenic in both groups, the geometric mean titer in the emory board treated group was 10 fold higher and the titers were more consistent among the latter animals as compared with the "water" animals. Thus it appears that physical disruption of the outer surface of the skin with an emory board enhances delivery of antigen by the transcutaneous route. This can be differentiated from techniques that seek to pierce the skin and deliver antigen through the skin, such as in subcutaneous, intradermal or intramuscular injection.

This simple device could be replaced by other physical disrupting devices to deliver antigens and adjuvants into the epidermis such as microneedles that are of length to disrupt only the stratum corneum or superficial epidermis, devices used for TB tine testing, gas powered guns which do not penetrate the dermis, adhesive tape for tape stripping, or other barrier disruption devices known to disrupt only the stratum corneum or superficial epidermis.

TABLE 5

Enhancement of transcutaneous immunization by physical penetration enhancement: Anti-CT titers in mice that had the skin treated with an emory board before application of the antigen.

| | anti-CT IgG (H + L) ELISA units | | |
|---|---|---|---|
| Animal # | treatment | prebleed | week 3 |
| 7146 | water | | 1275 |
| 7147 | water | | 69 |
| 7148 | water | | 7420 |
| 7149 | water | | 6025 |
| 7150 | water | | 388 |
| geometric mean | | | 1088 |
| pooled prebleed | | 7 | |
| 7151 | emory board | | 6632 |

TABLE 5-continued

Enhancement of transcutaneous immunization by physical penetration enhancement: Anti-CT titers in mice that had the skin treated with an emory board before application of the antigen.

| | anti-CT IgG (H + L) ELISA units | | |
|---|---|---|---|
| Animal # | treatment | prebleed | week 3 |
| 7152 | emory board | | 9380 |
| 7153 | emory board | | 31482 |
| 7154 | emory board | | 11142 |
| 7155 | emory board | | 11761 |
| geometric mean | | | 12074 |
| pooled prebleed | | 9 | |

Example 6

Another means of physical/mechanical penetration enhancement was employed using an abrasive pad to remove a portion of the stratum corneum and allow access to the underlying epidermis. BALB/c mice 6 to 8 weeks of age were anesthetized and shaved as described in the "immunization procedure". Twenty four hours later, the backs of the animals were either wiped with a gauze pad saturated in water, "water", or wiped with a gauze pad saturated in water followed by rubbing for 10 seconds with a nylon sponge (buf puf ©) to remove the outermost layers of the stratum corneum, "buf-puf ©". Excess water was removed from the backs of the "water" group and then 20 µg of CT (100 µl of a 0.2 mg/ml solution) was applied to the backs of all animals. Removal of excess antigen was conducted as described in the "immunization procedure."

The anti-CT antibody titers were determined using ELISA as described above for "ELISA IgG (H+L)" 3 weeks after a single immunization. The results are shown in Table 6. While CT was clearly immunogenic in both groups, the geometric mean titer in the buff puff treated group was 2 fold higher and the titers among individual animals were more consistent among the latter animals compared with the "water" animals. Thus it appears that physical disruption of the skin surface with a buff-puf © enhances delivery of antigen by the transcutaneous route.

This simple device could be replaced by other physical penetration devices to deliver antigens and adjuvants into the epidermis such as a needle and tuberculin syringe used for intradermal injection, microneedles that are of length to penetrate only the stratum corneum or superficial dermis, devices used for TB tine testing, abrading patches which have dissolvable crystals such as sucrose or sodium chloride or biodegradable polymers that are impregnated into the patch and rubbed on the skin before securing the patch with antigen either contained in the crystal or in the matrix, gas powered guns, adhesive tape for tape stripping, or other devices known to penetrate only into the epidermis or superficial dermis.

TABLE 6

Enhancement of transcutaneous immunization by physical penetration enhancement: Anti-CT titers in mice that had the skin treated with an abrasive pad (such as, for example, buf-puf ©) before application of the antigen.

| | | anti-CT IgG (H + L) ELISA units | |
|---|---|---|---|
| Animal # | treatment | prebleed | week 3 |
| 7146 | water | | 1275 |
| 7147 | water | | 69 |
| 7148 | water | | 7420 |
| 7149 | water | | 6025 |
| 7150 | water | | 388 |
| geometric mean | | | 1088 |
| pooled prebleed | | 7 | |
| 7166 | buf puf © | | 5376 |
| 7167 | buf puf © | | 2319 |
| 7168 | buf puf © | | 1209 |
| 7169 | buf puf © | | 2871 |
| 7170 | buf puf © | | 2785 |
| geometric mean | | | 2607 |
| pooled prebleed | | 8 | |

Example 7

Transcutaneous immunization with bacterial ADP-ribosylating exotoxins such as CT and LT appear to provide significant 'danger' signals to the immune system stimulating a potent immune response. Such compounds act as adjuvants. It was a surprise to find that simple mixtures of such adjuvants placed on the skin in a manner that hydrates the skin, resulting in potent immune responses. This was described in earlier patents (PCT/US97/21324). However, given that an adjuvant such as CT (86 KD) can act as an adjuvant on the skin, it would be expected that other adjuvants, particularly those based on bacterial products or motifs, would be stimulatory when placed on the skin in a manner that hydrates the skin and/or with the use of penetration enhancers.

We used bacterial DNA to confirm that this expectation is correct. BALB/c mice 6 to 8 weeks of age were shaved and anesthetized as described above for the "immunization procedure". On the day of immunization the backs of the mice were wiped with isopropanol to enhance penetration. After the alcohol had evaporated (approximately 5 minutes), 100 µl of phosphate buffered saline (PBS) containing 100 µg of DNA (CpG1 or CpG2) and 100 µg of diphtheria toxoid (DT) was applied to the back for 90 to 120 minutes. Oligonucleotides were synthesized by Oligos Etc with a phosphorothioate backbone to improve stability. Removal of excess antigen was conducted as described in the "immunization procedure." The immunization was repeated 4 and 8 weeks later. Ten weeks after the primary immunization the animals were bled and the anti-DT titers determined using an ELISA as described above for "ELISA IgG (H+L)". The results are shown in Table 7A.

Co-administration of DT and a control DNA sequence (SEQ ID NO:1; CpG2: TCCAATGAGCTTCCTGAGTCT) failed to induce a detectable rise in the anti-DT titers. In contrast, addition of a DNA sequence containing an unmethylated CpG dinucleotide flanked by two 5' purines and two 3' pyrimidines (SEQ ID NO:2; CpG1 (immunostimulatory DNA): TCCATGA<u>CG</u>TTCCTGACGTT) resulted in a detectable increase in the serum anti-DT IgG titer in 5 of 5 animals. Thus it appears that bacterial DNA containing appropriate motifs such as CPGs (6 KD) can be used as adjuvant to enhance delivery of antigen through the skin for induction of antigen specific antibody responses.

TABLE 7A

Adjuvant activity of bacterial DNA applied to the skin using penetration enhancement: humoral immune response.

| | | Anti-DT IgG (H + L) ELISA units | |
|---|---|---|---|
| Animal # | adjuvant/antigen | prebleed | week 10 |
| 7261 | CpG1/DT | | 1171 |
| 7262 | CpG1/DT | | 22750 |
| 7263 | CpG1/DT | | 4124 |
| 7264 | CpG1/DT | | 126 |
| 7265 | CpG1/DT | | 115 |
| Geometric mean | | | 1096 |
| pooled prebleed | | 6 | |
| 7266 | CpG2/DT | | 19 |
| 7267 | CpG2/DT | | 12 |
| 7268 | CpG2/DT | | 5 |
| 7269 | CpG2/DT | | 5 |
| 7270 | CpG2/DT | | 11 |
| geometric mean | | | 9 |
| pooled prebleed | | 5 | |

The transcutaneous effect of transcutaneous immunization can also be detected by T-cell proliferation. BALB/c mice 6 to 8 weeks of age were shaved and anesthetized as described above for the "immunization procedure". On the day of immunization the backs of the mice were wiped with isopropanol. After the alcohol had evaporated (approximately 5 minutes), 100 µl of phosphate buffered saline (PBS) containing 100 µg of DNA (CpG1 or CpG2) and 100 µg of diphtheria toxoid (DT) was applied to the back for 90 to 120 minutes. Oligonucleotides were synthesized by Oligos Etc with a phosphorothioate backbone to improve stability. Removal of excess antigen was conducted as described in the "immunization procedure." The immunization was repeated 4 and 8 weeks later. Twelve weeks after the primary immunization draining (inguinal) LNs were removed and pooled from five immunized animals. The capacity to proliferate in response to media or antigen (DT) was assessed in a standard 4 day proliferation assay using 3-H incorporation as a readout. The results are shown in Table 7B. Co-administration of DT and a DNA sequence containing an unmethylated CpG dinucleotide flanked by two 5' purines and two 3' pyrimidines (SEQ ID NO:2) resulted in a detectable increase in the antigen specific proliferative response. Thus it appears that bacterial DNA containing appropriate motifs can be used as adjuvant to enhance delivery of antigen through the skin for induction of proliferative responses.

TABLE 7B

Adjuvant effect of bacterial DNA applied to the skin: LN cell proliferation

| | proliferation (cpm) 3-H incorporation in vitro to antigens | |
|---|---|---|
| antigens applied in vivo | media | DT |
| normal LN | 339 | 544 |
| CpG1/DT | 1865 | 5741 |

Example 8

Transcutaneous immunization with bacterial ADP-ribosylating exotoxins such as CT and LT appear to provide significant 'danger' signals to the immune system stimulating a potent immune response. Such compounds act as adjuvants. It was a surprise to find that simple mixtures of such adjuvants placed on the skin in a manner that hydrates the skin, resulting in potent immune responses. This was described in earlier patents (PCT/US97/21324). However, given that an adjuvant such as CT can act as an adjuvant on the skin, it would be expected that other adjuvants, would be stimulatory when placed on the skin in a manner that hydrates the skin. Genetically altered toxins were used to confirm this expectation. BALB/c mice 6 to 8 weeks of age were anesthetized, shaved, and immunized as described in the "immunization procedure". The animals were boosted 3 and 5 weeks after the primary immunization and serum collected 2 weeks after the final immunization. The adjuvants used were the genetically altered toxins; LTK63, an enzymatically inactive LT derivative, and LTR72, an LT derivative which retains 0.6% of the enzymatic activity. Diphtheria toxoid (DT) 100 µg was used as antigen.

Anti-DT antibody titers were determined using ELISA as described above for "ELISA IgG (H+L)". The results are shown in Table 8. Anti-DT titers were clearly elevated in serum from animals immunized with either LTR63 or LTR72 and DT when compared with titers in serum collected prior to immunization (prebleed). Thus it appears that genetically detoxified mutants of heat labile enterotoxin (LT) can be used as adjuvants on the skin.

TABLE 8

Use of genetically altered toxins, LTK63 and LTR72, as adjuvants on the skin.

| | | anti-DT IgG (H + L) ELISA units | |
|---|---|---|---|
| Animal # | adjuvant/antigen | prebleed | week 7 |
| 653 | LTK63/DT | | 20228 |
| 654 | LTK63/DT | | not available |
| 655 | LTK63/DT | | 342 |
| 656 | LTK63/DT | | 2445 |
| 657 | LTK63/DT | | <100 |
| geometric mean | | | 1140 |
| pooled prebleed | | <100 | |
| 663 | LTR72/DT | | 12185 |
| 664 | LTR72/DT | | 10917 |
| 665 | LTR72/DT | | 151 |
| 666 | LTR72/DT | | 2057 |
| 667 | LTR72/DT | | 50923 |
| geometric mean | | | 4620 |
| pooled prebleed | | <100 | |

Example 9

Another class of compounds, cytobines which are known to act as adjuvants illustrate the principle that adjuvants in general could be expected to act in a fashion similar to cholera toxin. TNFα is also known to be a Langerhan cell activating compound.

BALB/c mice 6 to 8 weeks of age were shaved and anesthetized as described above for the "immunization procedure". On the day of immunization the backs of the mice were wiped with isopropanol. After the alcohol had evaporated (approximately 5 minutes), 100 µl of phosphate buffered saline (PBS) containing 0.83 µg TNF-alpha (recombinant mouse TNF-alpha, Endogen), IL-2 (1 µg recombinant mouse IL-2 (Sigma)) or mock adjuvant (CpG2) was applied to the skin on the back with 100 µg of diphtheria toxoid (DT) for 90 to 120 minutes. Oligonucleotides were synthesized by Oligos Etc with a phosphorothioate backbone to improve stability Removal of excess antigen was conducted as described in the "immunization procedure." The immunization was repeated 4 and 8 weeks later. Ten weeks after the primary immunization the animals were bled and the anti-DT titers determined using an ELISA as described above for "ELISA IgG (H+L)". The results are shown in Table 9.

Co-administration of DT and a mock adjuvant (CpG2) failed to induce a detectable rise in the anti-DT titers. In contrast, topical application of TNF-alpha (0.8 µg) resulted in a detectable increase in the serum anti-DT IgG titer in 3 of 5 animals when compared with either anti-DT titers in the mock adjuvant treated mice or sera collected prior to immunization (prebleed). Similarly, topical application of IL-2 (1 µg) resulted in a detectable increase in the serum anti-DT IgG titer in 4 of 5 animals when compared with either anti-DT titers in the mock adjuvant treated mice or sera collected prior to immunization (prebleed). Thus it appears that the cytokines such as IL-2 and TNF-alpha can be used as an adjuvant on the skin and that langerhans cell activating compounds can be used for transcutaneous immunization.

TABLE 9

Adjuvant activity of the cytokine TNF-alpha applied to the skin.

| | | Anti-DT IgG (H + L) ELISA units | |
|---|---|---|---|
| Animal # | adjuvant/antigen | prebleed | week 10 |
| 7326 | TNF-alpha/DT | | 1808 |
| 7327 | TNF-alpha/DT | | 830 |
| 7328 | TNF-alpha/DT | | 7 |
| 7329 | TNF-alpha/DT | | 1477 |
| 7330 | TNF-alpha/DT | | 7 |
| geometric mean | | | 159 |
| pooled prebleed | | 1 | |
| 7331 | IL-2/DT | | 13 |
| 7332 | IL-2/DT | | 111 |
| 7333 | IL-2/DT | | 345 |
| 7334 | IL-2/DT | | 49 |
| 7335 | IL-2/DT | | 35 |
| geometric mean | | | 61 |
| pooled prebleed | | 2 | |
| 7266 | CpG2/DT | | 19 |
| 7267 | CpG2/DT | | 12 |
| 7268 | CpG2/DT | | 5 |
| 7269 | CpG2/DT | | 5 |
| 7270 | CpG2/DT | | 11 |
| geometric mean | | | 9 |
| pooled prebleed | | 5 | |

Example 10

The B-subunit of cholera toxin is another class of adjuvants lack the A-subunit and therefore ADP-ribsyltransferase activity of CT. As such CTB represents an adjuvant that is unique and may be useful as it is not toxic when ingested.

C57BL/6 mice 6 to 8 weeks of age were anesthetized and shaved as described in the "immunization procedure". On the day of immunization the backs of the mice were wiped with isopropanol. After the alcohol had evaporated (approximately 5 minutes), 100 µl of phosphate buffered saline (PBS) containing 100 µg of purified cholera toxin B subunit (CTB) and/or 100 µg of diphtheria toxoid (DT) was applied to the back for 90 to 120 minutes. Removal of excess antigen was conducted as described in the "immunization procedure." The immunization was repeated 4 and 8 weeks later. Ten weeks after the primary immunization the animals were bled and the anti-DT titers determined using an ELISA as described above for "ELISA IgG (H+L)". The results are shown in Table 10.

Anti-DT titers were clearly elevated in serum from animals immunized with CTB and DT when compared with titers in serum from animals treated with DT alone or those in prebleed serum samples as shown in Table 10. Thus it appears that purified CTB can be used as an adjuvant on the skin.

TABLE 10

Use of purified cholera toxin B subunit from *V. cholerae* as an adjuvant on the skin.

| | Anti-DT IgG (H + L) ELISA units | | |
|---|---|---|---|
| Animal # | adjuvant/antigen | prebleed | week 10 |
| 51 | DT | | 11 |
| 52 | DT | | 7 |
| 53 | DT | | 4 |
| 54 | DT | | 8 |
| 55 | DT | | 7 |
| geometric mean | | | 7 |
| pooled prebleed | | 4 | |
| 81 | CTB/DT | | 14880 |
| 82 | CTB/DT | | 371 |
| 83 | CTB/DT | | 14810 |
| 84 | CTB/DT | | 108 |
| 85 | CTB/DT | | 27 |
| geometric mean | | | 751 |
| pooled prebleed | | 5 | |

Example 11

Adjuvants that are structurally different are likely to exert their enhancement by different effects. Adjuvants that induce their effects by different mechanisms may have either additive or synergistic effects on enhancing the immune response. We found that the use of two adjuvants simultaneously augmented the response to transcutaneous immunization compared to the individual adjuvants alone.

BALB/c mice 6 to 8 weeks of age were shaved and anesthetized as described above for the "immunization procedure". On the day of immunization the backs of the mice were wiped with isopropanol. After the alcohol had evaporated (approximately 5 minutes), 100 μl of phosphate buffered saline (PBS) containing 100 μg of immunostimulatory DNA (CpG1) and/or cholera toxin (CT) 100 μg was applied to the back with 100 μg of a soluble leishmanial antigen extract (SLA) for 90 to 120 minutes. SLA is an antigen extract prepared at Walter Reed Army Institute of Research by centrifugal isolation of the soluble proteins in a sonicate of *Leishmazia major* promastigotes) extract for 90 to 120 minutes. Removal of excess antigen was conducted as described in the "immunization procedure." The immunization was repeated 4 and 8 weeks later. Twelve weeks after the primary immunization draining (inguinal) LNs were removed and pooled from two immunized animals. The capacity to proliferate in response to media or antigen (SLA) was assessed in a standard 4 day proliferation assay using 3-H incorporation as a readout. The results are shown in Table 11.

Co-administration of SLA and CpG1 (immunostimulatory DNA containing an unmethylated CpG dinucleotide flanked by two 5' purines and two 3' pyrimidines—SEQ ID NO:2) or CT resulted in a detectable increase in the antigen specific proliferative response. However, the antigen (SLA) specific proliferative response was approximately 20 times higher in lymph node cell cultures from animals exposed simultaneously to both CpG1 and CT as compared to cultures derived from animals exposed to either adjuvant alone. Thus it appears that bacterial DNA containing appropriate motifs synergizes with ADP ribosylating exotoxins such as CT as adjuvants on the skin to induce higher immune responses than to either adjuvant alone.

TABLE 11

Synergy between immunostimulatory DNA and ADP ribosylating exotoxin (CT) as adjuvants when applied to the skin

| | proliferation (cpm) 3-H incorporation in vitro to antigens | |
|---|---|---|
| substances applied in vivo | media | SLA |
| normal LN | 180 | 219 |
| SLA | 200 | 159 |
| SLA/CpG1 | 1030 | 2804 |
| SLA/CT | 232 | 2542 |
| SLA/CpG1/CT | 2232 | 47122 |

Example 12

Transcutaneous immunization induces potent immune responses when used as a method of delivery alone. We also have found that transcutaneous immunization can be used in sequence with other routes of delivery to stimulate an immune response.

BALB/c mice 6 to 8 weeks of age On day 0 both groups of animals received a 50 μl intramuscular (im.) injection of DT (5 μg) mixed with alum (Rehydrogel-25 μg in NaCl) into the hind thigh. Eight and 16 weeks later mice in the im/tc/tc group were shaved, anesthetized and immunized by the transcutaneous route as described above for the "immunization procedure" using 100 μg cholera toxin as adjuvant and 100 μg diphtheria toxoid as antigen. The immunization solution was applied to the back for 90 to 120 minutes. Removal of excess antigen was conducted as described in the "immunization procedure." Twenty two weeks after the primary immunization the animals were bled and the anti-DT titers determined using an ELISA as described above for "ELISA IgG (H+L)". The results are shown in Table 12.

A single im. injection of 5 μg of DT induced a detectable rise in the serum anti-DT titers as compared with titers in sera collected from the same animals prior to immunization (prebleed). Boosting of the im. primed animals using the transcutaneous immunzation method resulted in an 60 fold rise in the geometric mean titer and clearly all transcutaneously boosted animals had higher anti-DT titers that those observed in the im. primed group. Thus transcutaneous immunization can be used to boost antigen specific titers in mice in which the primary immunization with the antigen was by the i.m. route. We have also found that im primed animals can be boosted by transcutaneous immunization (TCI). Various combinations of TCI priming or boosting with other routes and schedules can be visualized including oral, buccal, nasal, rectal, vaginal, intradermal, by gun or other means of delivery. Additionally, antigens may differ in route and composition including protein alternating with glycoprotein, subunit with holotoxin, DNA priming followed by protein, nucleic acid by im followed by nucleic acid by TCI. Transcutaneous immunization may be used to boost children primed in infancy or adults primed in childhood. The ease of delivery may enhance the efficacy vaccines such as the influenza vaccines by allowing multiple boosts using a patch.

TABLE 12

Boosting of im. primed animals using the transcutaneous immunization method

Anti-DT IgG (H + L) ELISA units

| Animal # | adjuvant/antigen | Route of administration | prebleed | week 22 |
|---|---|---|---|---|
| 8563 | DT | im. | | 54227 |
| 8564 | DT | im. | | 11833 |
| 8565 | DT | im. | | 106970 |
| 8566 | DT | im. | | 10830 |
| 8567 | DT | im. | | 4003 |
| geometric mean | | | | 19711 |
| pooled prebleed | | | 20 | |
| 8568 | DT/ct + dt/ct + dt | im./tc./tc. | | 628838 |
| 8569 | DT/ct + dt/ct + dt | im./tc./tc. | | 2035507 |
| 8570 | DT/ct + dt/ct + dt | im./tc./tc. | | 1164425 |
| 8571 | DT/ct + dt/ct + dt | im./tc./tc. | | not available |
| 8572 | DT/ct + dt/ct + dt | im./tc./tc. | | 1263138 |
| geometric mean | | | | 1171368 |
| pooled prebleed | | | 10 | |
| 8558 | DT/DT/DT | im./im./im. | | not available |
| 8559 | DT/DT/DT | im./im./im. | | 542669 |
| 8560 | DT/DT/DT | im./im./im. | | 770150 |
| 8561 | DT/DT/DT | im./im./im. | | 545894 |
| 8562 | DT/DT/DT | im./im./im. | | 671898 |
| geometric mean | | | | 625721 |
| pooled prebleed | | | 15 | |

Example 13

Because TCI appears to stimulate the immune system in such a potent fashion, it is possible that an adjuvant place on the skin at one site may act as an adjuvant for an antigen placed at another site. BALB/c mice 6 to 8 weeks of age were anesthetized and shaved as described in the "immunization procedure". Animals were not ear tagged but kept in cages labeled A, C or G. On the day of immunization the dorsal surface of the mouse ear was treated by gently rubbing the outer skin surface with a cotton-tipped applicator containing 70% isopropanol. After 5 minutes the excess water was blotted from water-treated ears and adjuvant (CT 50 μg) and/or antigen (100 μg of bovine serum albumin (BSA) was applied to the left or right ear surface (described in table) in 50 μl phosphate buffered saline. At two and a half hours, the ears were rinsed and blotted dry twice. Mice were boosted in a similar fashion four and eight weeks later. Twelve weeks after the primary immunization the animals were bled and the anti-BSA titers determined using an ELISA as described above for "ELISA IgG (H+L)". The results are shown in Table 13.

Application of BSA alone to the skin was poorly immunogenic with only 1 of 5 animals developing an ELISA titer above 100 EU. In contrast, 9 of 9 animals receiving CT and BSA on the skin developed titers above 100 EU. Of the animals receiving antigen and adjuvant, the mice given the materials at the same site (left ear) developed higher (10 fold) anti-BSA titers than animals receiving antigen and adjuvant in separate (left and right) ears. However, animals receiving antigen on one ear and adjuvant on another ear developed an anti-BSA immune response that was approximately 30 times higher that animals given BSA alone. Thus, antigen and adjuvant may be topically applied during TCI at different sites to elicit a humoral immune response. This immunostimulation may be expected to occur with antigen delivered by other routes and schedules can be visualized including oral, buccal, nasal, rectal, vaginal, intradermal, by gun or other means of delivery. Additionally, adjuvants may be used with nucleic acid immunization to enhance the response. Such a delivery may not need to be simultaneous to enhance the immune response. For example, an im injection of plasmid DNA may be followed later by transcutaneous administration of adjuvant. Immunostimulation by CT, LT, TNF∝, CpGs or similar adjuvants is a surprising result because it has been thought that molecules 500 daltons could not pass through the skin.

TABLE 13

Delivery of antigen and adjuvant at the same or distal sites on the skin with penetration enhancement.

Anti-BSA IgG (H + L) ELISA units

| Animal # | adjuvant/antigen | prebleed | week 12 |
|---|---|---|---|
| group G | BSA left ear | | 240 |
| group G | BSA left ear | | 99 |
| group G | BSA left ear | | 40 |
| group G | BSA left ear | | not available |
| group G | BSA left ear | | 15 |
| Geometric mean | | | 61 |
| pooled prebleed | | 6 | |
| group C | CT/BSA left ear | | 16418 |
| group C | CT/BSA left ear | | 24357 |
| group C | CT/BSA left ear | | 13949 |
| group C | CT/BSA left ear | | 70622 |
| group C | CT/BSA left ear | | not available |
| Geometric mean | | | 25053 |
| pooled prebleed | | 3 | |
| group A | CT left/BSA right ear | | 106 |
| group A | CT left/BSA right ear | | 23806 |
| group A | CT left/BSA right ear | | 1038 |
| group A | CT left/BSA right ear | | 1163 |
| group A | CT left/BSA right ear | | 8696 |
| Geometric mean | | | 1939 |
| pooled prebleed | | 15 | |

Example 14

Transcutaneous Immunization in Humans

The invention can be practiced using a suitable vehicle or carrier. For example a patch can be used as such a vehicle and can be treated with the formulation of the invention or can be used to cover the area of the skin which has been treated with the formulation of the invention. A suitable patch can be fabricated from, for example, cotton, nylon, rayon, polyester or combinations thereof. Such patches can be provided with an adhesive or non-adhesive backing. Patches with a non-adhesive backing can be secured to the animal by non-adhesive means, such as, for example, wrapping. Suitable backing can be fabricated from materials such as, for example, silicon, acrylate or rubber. Other vehicles or carriers which can be used include those listed above; such as for example, powders, oils, water, cream and the like. To evaluate the potential for TCI in humans, a Phase I trial was conducted using LT to attempt to induce serum anti-LT antibodies. Six volunteers received a dose of 500 μg of LT, a dose similar to oral adjuvant doses used for a cholera vaccine (1 mg CTB). L tions at the Swiss Serum and Vaccine Institute (Berne, Switzerland) and was provided by Oravax Inc., Cambridge, Mass. The volunteers received 500 µg of LT mixed in 500 µl of sterile saline which was absorbed on a 2 in$^2$ cotton gauze pad with polyvinyl backing and covered by a 4×4 in$^2$ Tegaderm™ dressing. The immunization was conducted by placing the patch on unmanipulated skin for 6 hours after which the site was thoroughly rinsed with 500 ml of sterile saline. Individuals were similarly reimmunized after 12 weeks. Volunteers were examined on days 1, 2, 3 and 7 for signs of inflammation at the site of immunization and interviewed for symptoms related to the vaccination. The immunization was conducted by placing the patch on unmanipulated skin for 6 hours after which the patch was removed and the site was thoroughly rinsed with saline. Individuals were reimmunized after 12 weeks. No adverse reactions were seen, either systemically or at the site of immunization after the first or second immunization. Anti-LT IgG titers were determined as previously described. Results are reported in ELISA units (EU) which are defined as the inverse dilution of sample that yields an OD of 1.0. Anti-LT IgA was determined in the same manner as anti-LT IgG using goat anti-human IgA(α)-HRP (Kirkegaard and Perry, Gaithersburg, Md.) against a standard IgA curve made using human IgA (ICN). As shown in Table 14, 6 of 6 individuals responded by producing a rise in serum anti-LT IgG or IgA antibodies, defined as a four-fold increase in antibody titers. The mean fold rise in anti-LT IgG was 10.2 and the mean fold rise in serum anti-LT IgA was 7.2. Biopsies of the immunization site and contralateral arm showed no signs of inflammation of the skin. These results confirm that TCI can be conducted in humans without skin irritation or inflammation.

Suitable patch materials have been previously described. In general the patch may consist of, for example, a pressure sensitive dressing, a matrix for or absorbant layer to carry the vaccines and adjuvant, a vaccine impermeable backing and a release liner. This and other suitable patch examples are described in U.S. Pat. Nos. 4,915,950 and 3,734,097.

Patches can be fabricated to include woven and non-woven matrices of materials to include, for example, polyester/cellulose, polypropylene, polyester, polyester/rayon and the like.

Examples of non-woven patch matrices can include:

BBA Nonwovens
   a. Grade# 1313290, wet laid non-woven, composition=polyester/cellulose, weight (gsy)=35.4, weight (gsm)=42.3, thickness (mils)=7.9, tensile MD=3.4, tensile CD=2.4.
   b. Grade# 2006086, thermal bond non-woven, composition=polypropylene, weight (gsy)=16.0, weight (gsm)=19.1, thickness (mils)=10.2, tensile MD=3.3, tensile CD=0.7.
   c. Grade# 149146, thermal bond non-woven, composition=polyester, weight (gsy)=25.6, weight (gsm)=30.6, thickness (mils)=6.5, tensile MD=5.3, tensile CD=0.9.
   d. Grade# 149020, thermal bond non-woven, composition=polyester/rayon, weight (gsy)=30.5, weight (gsm)=36.4, thickness (mils)=13.2, tensile MD=5.5, tensile CD=1.1.
   e. Grade# 140-027, hydroentangled nonwoven, composition=polyester/rayon, weight (gsy)=28.0, weight (gsm)=33.5, thickness (mils)=22.4, tensile MD=10.4, tensile CD=3.8.

Pressure sensitive adhesive that can be used in the present invention include, for example adhesive based on acrylate, silicone, rubber and the like.

TABLE 14

Mean fold rise in human anti-LT IgG and IgA

| Volunteer # | 4 week IgG | 12 week IgG | 16 week IgG |
|---|---|---|---|
| 13 | 15.2 | 9.5 | 12.5 |
| 14 | 1.4 | 1.6 | 1.7 |
| 15 | 11.7 | 15.0 | 12.9 |
| 16 | 1.3 | 0.7 | 16.0 |
| 17 | 12.5 | 51.9 | 58.6 |
| 18 | 1.3 | 2.1 | 4.3 |
| Mean rise IgG | 4.2 | 5.0 | 10.2 |

| Volunteer # | 4 week IgA | 12 week IgA | 16 week IgA |
|---|---|---|---|
| 13 | 7.2 | 4.1 | 10.1 |
| 14 | 4.9 | 4.3 | 4.3 |
| 15 | 4.9 | 5.7 | 4.5 |
| 16 | 1.4 | 1.3 | 7.0 |
| 17 | 15.3 | 29.4 | 28.1 |
| 18 | 1.3 | 1.5 | 3.5 |
| Mean rise IgA | 4.1 | 4.2 | 7.2 |

Example 15

LT has been shown to be effective for immunizing humans by the transcutaneous route. We also have found that LT acts as an adjuvant for TCI. C57BL/6 mice 6 to 8 weeks of age were anesthetized and shaved as described in the "immunization procedure". On the day of immunization the backs of the mice were wiped with isopropanol. After the alcohol had evaporated (approximately 5 minutes), 100 µl of phosphate buffered saline (PBS) containing 100 µg of heat labile enterotoxin (LT) and/or 100 µg of diphtheria toxoid (DT) was applied to the back for 90 to 120 minutes. Removal of excess antigen was conducted as described in the "immunization procedure." The immunization was repeated 4 and 8 weeks later. Ten weeks after the primary immunization the animals were bled and the anti-DT titers determined using an ELISA as described above for "ELISA IgG (H+L)". The results are shown in Table 15.

Anti-DT titers were clearly elevated in serum from animals immunized with LT and DT when compared with titers in serum from animals treated with DT alone or those in prebleed serum samples. Thus it appears that heat labile enterotoxin (LT) can be used as an adjuvant on the skin.

TABLE 15

Use of heat labile enterotoxin (LT) from *E. coli* as an adjuvant on the skin.

| | | Anti-DT IgG (H + L) ELISA units | |
|---|---|---|---|
| Animal # | adjuvant/antigen | prebleed | week 10 |
| 51 | DT | | 11 |
| 52 | DT | | 7 |
| 53 | DT | | 4 |
| 54 | DT | | 8 |
| 55 | DT | | 7 |
| geometric mean | | | 7 |
| pooled prebleed | | 4 | |
| 71 | LT/DT | | 7126 |
| 72 | LT/DT | | 46909 |
| 73 | LT/DT | | 669 |
| 74 | LT/DT | | 8480 |
| 75 | LT/DT | | 1598 |

TABLE 15-continued

Use of heat labile enterotoxin (LT) from *E. coli* as an adjuvant on the skin.

| | Anti-DT IgG (H + L) ELISA units | | |
|---|---|---|---|
| Animal # | adjuvant/antigen | prebleed | week 10 |
| geometric mean | | | 4970 |
| pooled prebleed | | 5 | |

Example 16

To assess the role of physical/mechanical penetration enhancement, the superficial layers of the stratum corneum were removed by tape stripping. Tape stripping is an intervention well known in the art to remove the outer layer of the stratum corneum. C57BL/6 mice 6 to 8 weeks of age were anesthetized and shaved as described in the "immunization procedure." Twenty four hours later, CT (25 μg) was applied to the backs of the mice in 50 μl of phosphate buffered saline; "none" intervention group. Alternatively, the skin on the backs of a second group of animals was subjected to mild tape stripping; "tape stripping" intervention group. The tape stripping procedure was accomplished by applying cellophane scotch-tape to the backs, allowing bonding to the skin surface for 3 minutes, followed by gentle removing of the tape. The bonding/removal steps were repeated 3 times. CT (25 μg) was then applied to the backs of the mice in 50 μl of phosphate buffered saline. Antigen remained on the backs for approximately 1.5 hrs at which time removal of excess antigen was conducted as described in the "immunization procedure."

The anti-CT antibody titers were determined using ELISA as described above for "ELISA IgG (H+L)" using sera collected 11 days after the primary immunization. The results are shown in Table 16. CT was immunogenic in both groups as compared to sera collected from the same animals prior to immunization (prebleed). However, the geometric mean titer in the tape stripped group was 100 fold higher and the titers were more consistent among the latter animals as compared with the "none" animals. Thus it appears that physical disruption of the skin surface using tape stripping enhances delivery of antigen by the transcutaneous route.

This simple device could be replaced by other physical penetration devices to deliver antigens and adjuvants into the epidermis such as a needle and tuberculin syringe used for intradermal injection, microneedles that are of length to penetrate only the stratum corneum or superficial dermis, devices used for TB tine testing, gas powered guns, adhesive tape for tape stripping, or other devices known to penetrate only into the epidermis or superficial dermis. Tape stripping devices could be used in conjunction with other penetration enhancers. Tape stripping devices may be used in conjunction with a marker to delineate the site for patch placement, and may be dispersed in a roll or in individual units.

TABLE 16

Enhancement of transcutaneous immunization by physical penetration enhancement: Anti-CT titers in mice that had the skin stripped using cellophane tape before application of the antigen.

| | | anti-CT IgG (H + L) Elisa units | |
|---|---|---|---|
| Animal # | intervention | prebleed | day 11 |
| 976 | none | | 155 |
| 977 | none | | 4 |
| 978 | none | | 4 |
| 979 | none | | 31 |
| 980 | none | | 23 |
| geomean | | | 16 |
| prebleed | | 2 | |
| 986 | tape strip | | 10702 |
| 987 | tape strip | | 1285 |
| 988 | tape strip | | 5832 |
| 989 | tape strip | | 997 |
| 990 | tape strip | | 782 |
| geomean | | | 2990 |
| prebleed | | 3 | |

Example 17

Nucleic acids such as plasmid DNA or RNA can be used to induce and immune response and are well known in the art. The use of Nucleic acids in transcutaneous immunization was described in previous patents (PCT/US97/21324). The use of nucleic acids (also known as genetic immunization) on the skin with penetration enhancement techniques is illustrated in the following example.

C57BL/6 mice 6 to 8 weeks of age were anesthetized and shaved as described in the "immunization procedure". For the "NP DNA" group the mice were wiped with isopropanol, after the alcohol had evaporated (approximately 10 minutes), the backs were hydrated with water using a saturated gauze pad. Approximately 10 minutes later the any excess water was blotted off and a 100 μg of a DNA plasmid (pCMV-NP) encoding for influenza nucloprotein was applied to the back in 100 μl of saline. A second group of NP-DNA mice were subjected to the same immunization protocol except that their backs were tape stripped 3× prior to alcohol swabbing; "NP DNA—tape stripping". The tape stripping procedure was accomplished by applying cellophane scotch-tape to the backs, allowing bonding to the skin surface for 5 minutes, followed by gentle removing of the tape. A third group of mice was engaged in the tape stripping/immunization protocol described and 100 μg of the adjuvant heat labile enterotoxin (LT) was included in the immunization solution. Sixteen days after the primary immunization the animals were bled and the anti-influenza NP titers determined using an ELISA as described above for "ELISA IgG (H+L)". The results are shown in Table 17.

Anti-influenza titers were determined using a split virus antigen (Fluzone) preparation to coat the ELISA plates. ELISA titers were determined in 5 individual animals and the mean optical density reading for each group is shown. All three immunization groups developed anti-influenza titers as compared with titers in serum collected from the same animals prior to immunization (prebleed). As compared with the NP DNA alone group, tape stripping prior to immunization enhanced the anti-Influenza titer in all three serum dilutions tested (1:100, 1:200, 1:400) and addition of an adjuvant (LT) further enhanced this response. Thus, DNA can be used on the skin to induce immune responses to vaccine antigens and its effectiveness can be enhanced by the addition of adjuvants and penetration enhancement such as tape stripping.

TABLE 17

Immuogenicity of DNA applied as antigen on the skin using alcohol penetration enhancement.

| | | Anti-INF IgG optical density (405 nm) | | | |
|---|---|---|---|---|---|
| | | prebleed | day 16 post immunization | | |
| Antigen/adjuvant | intervention | 1:100 | 1:100 | 1:200 | 1:400 |
| NP DNA | none | 0.21 | 0.47 | 0.20 | 0.07 |
| NP DNA | tape stripping | 0.39 | 0.64 | 0.28 | 0.13 |
| NP DNA/LT | tape stripping | 0.39 | 0.87 | 0.38 | 0.13 |

Example 18

Transcutaneous immunization (TCI), because of the ease of delivery, allows the application to be given over different draining lymph nodes. This may have an additional advantage in that it enhances the immune response. Rabbits were anesthetized, shaved, and immunized as described above. Animals were immunized with 100 µg cholera toxin (CT) and 100 µg of influenza hemagglutinin (HA) at one site or two sites on the back. HA and CT were applied at 0, 3 and 5 weeks. Seven weeks after the primary immunization, the animals were bled and the anti-HA titers determined using an ELISA as described above for "ELISA IgG (H+L)". The results are shown in Table 18.

Anti-HA titers were elevated in serum from 10 of 10 animals immunized with CT and HA when compared with titers in serum from the same animals prior to immunization (prebleed). The geometric mean titer in the two site group was 3 fold higher than that in the one site group suggesting that antigen delivery at multiple sites may be used to enhance TCI. Thus, antigens can be delivered by TCI either at a single or multiple sites on the skin.

TABLE 18

Transcutaneous delivery of antigen in a single or multiple sites.

| | | anti-HA IgG (ELISA units) | | |
|---|---|---|---|---|
| Animal | antigen/adjuvant | prebleed | 7 weeks | geomean |
| 1 | CT/HA one site | <25 | 1142 | 2596 |
| 2 | CT/HA one site | <25 | 9617 | |
| 3 | CT/HA one site | <25 | 2523 | |
| 4 | CT/HA one site | <25 | 2275 | |
| 5 | CT/HA one site | <25 | 1869 | |
| 6 | CT/HA two sites | <25 | 10348 | 8403 |
| 7 | CT/HA two sites | <25 | 18453 | |
| 8 | CT/HA two sites | <25 | 9778 | |
| 9 | CT/HA two sites | <25 | 15985 | |
| 10 | CT/HA two sites | <25 | 1404 | |

Example 19

The variety of antigens which can be delivered by TCI is further illustrated by the use of a polysaccharide conjugate vaccine to induce anti-polysaccharide antibodies. BALB/c mice 6 to 8 weeks of age were anesthetized, shaved, and immunized as described in the "immunization procedure". Mice were immunized with cholera toxin (CT) and *Haemophilus influenzae* B polysaccharide (Hib-PS) at 0, 3 and 5 weeks. Seven weeks after the primary immunization, the animals were bled and the anti-Hib-PS titers determined using an ELISA as described above for "ELISA IgG (H+L)". The results are shown in Table 19.

Anti-Hib-PS titers were elevated in serum from 4 of 10 animals immunized with CT and Hib-PS when compared with titers in serum from the same animals prior to immunization (prebleed). Thus TCI can be used to induce anti-polysaccharide antigens through the skin. This is a common human use vaccine antigen and represents and important strategy for immunization.

TABLE 19

Delivery of a conjugated polysaccharide by transcutaneous immunization

| | | anti-Hib PS IgG (µg/ml) | |
|---|---|---|---|
| ear tag # | antigen/adjuvant | prebleed | 7 weeks |
| 1 | CT/Hib-PS (100 µg/100 µg) | <0.20 | <0.20 |
| 2 | CT/Hib-PS (100 µg/100 µg) | <0.20 | <0.20 |
| 3 | CT/Hib-PS (100 µg/100 µg) | <0.20 | 1.68 |
| 4 | CT/Hib-PS (100 µg/100 µg) | <0.20 | <0.20 |
| 5 | CT/Hib-PS (100 µg/100 µg) | <0.20 | 1.86 |
| 6 | CT/Hib-PS (100 µg/25 µg) | <0.20 | 1.04 |
| 7 | CT/Hib-PS (100 µg/25 µg) | <0.20 | <0.20 |
| 8 | CT/Hib-PS (100 µg/25 µg) | <0.20 | <0.20 |
| 9 | CT/Hib-PS (100 µg/25 µg) | <0.20 | 6.30 |
| 10 | CT/Hib-PS (100 µg/25 µg) | <0.20 | <0.20 |

Example 20

Transcutaneous immunization of mice with human use vaccine antigens CT has been shown to act as adjuvant for transcutaneous immunization with single toxoids and BSA. We transcutaneously immunized mice with a variety of human-use vaccine antigens, including a multivalent toxoid vaccine (tetanus and diphtheria toxoids), a yeast expressed recombinant protein(HIV p55 gag) and whole killed rabies viruses using CT as an adjuvant as shown in Table 20. BALB/c mice (n=5) were immunized and boosted twice as previously described (Glenn, G. M., Scharton-Kersten, T., Vassell, R., Matyas, G. & Alving. C. R. Transcutaneous immunization using bacterial ADP-ribosylating exotoxins as antigens and adjuvants. Infect. Immun. (in the press). Immunizing doses included 100/50/50 µg CT/TT/DT via TCI versus 3/1/1 for alum/TT/DT IM; 100/100 µg for LT+DT versus 100 µg of DT alone. 100/100 µg for CT/p55 via TCI versus 100 µg p55 alone. Mice immunized with 17 IE of killed rabies virus (n=10) had been primed intramuscularly 2× and then boosted transcutaneously (17 IE) after light alcohol swabbing of the skin and compared to 3×IM rabies immunization. Antibody levels against DT, TT, p55 and rabies were determined using ELISA as previously described (Grassi, M., Wandler, A. & Peterhans, E. Enzyme-linked immunoabsorbant assay for determination of antibodies to the envelope glycoprotein of rabies virus. *J. Clin. Microbiol.* 27, 899-902 (1989). Miyamura, K., Tajiri, E., Ito, A., Murata, R. & Kono, R. Micro cell culture method for determination of diphtheria toxin and antitoxin titres using VERO cells. II. Comparison with the rabbit skin method and practical application for seroepidemiological studies. *J. Biol. Stand.* 2, 203-209 (1974)). TCI resulted in similar increases in the antibody responses to TT and DT and the anti-DT neutralization titers were comparable to that elicited by intramuscular immunization (IM). These data show that TCI may be used to induce immune response of comparable magnitude as those induced by existing immunization practices. TCI boosting of IM primed animals also resulted in a significant rise in anti-rabies titers in all 10 animals tested (0.53 to 1.03 IU, p<0.02, Student's t-test). Antibodies to the antigens DT and p55 administered without adjuvants were very low or undetectable, consistent with our previous observations that antigens are only weakly immunogenic when applied without adjuvant. LT also acted as adjuvant (Table 20) in a fashion similar to previous studies using CT (1,2). Although the immunizations were not optimized as compared to intramuscular delivery, these antigen-specific responses confirm that TCI may be used for a variety of human-use vaccines from a variety of sources an a variety of sizes and that LT can act as an adjuvant for coadministered vaccine antigens.

TABLE 20

Murine antibody responses to human-use vaccine antigens administered by TCI

| Immunizing Antigen(s) for TCI | Antibody specificity | TCI (ELISA Units) | IM/alum (ELISA Units) |
|---|---|---|---|
| CT + TT + DT | Anti-DT | 135,792 (86,552-146-759) | 85,493 (24,675-238,904) |
| CT + TT + DT | Anti-TT | 30,051 (13,863-53,174) | 94,544 (74,928-113,408) |
| CT + TT + DT | Diphtheria toxin neutralization | 404 (22-2816) | 1,226 (352-11,264) |
| LT + DT | Anti-DT | 4976 (669-46,909) | ND |
| CT + HIV p55 gag | Anti-p55 | 10,630 (1063-52,597) | ND |
| CT + Killed Rabies Virus | Anti-G protein | 1.03 (IU/ml) (0.31-2.77) | 7.54 (IU/ml) (3.31-17.47) |

ND = not done. ELISA units (EU) shown as geometric mean and range in brackets.

Example 21

Langerhans Cell Activation

Figure 1B:
Figure 1C:
Figure 1D:
Figure 1E:
Figure 1F:

In two subjects, the site of immunization and the contralateral unimmunized arm were biopsied, one at 24 hours post-immunization and one at 48 hours after the second immunization. Hematoxylin and eosin (H&E) staining of the specimens confirmed the clinical findings suggesting that no inflammation was seen after the immunization (FIG. 1 A,B). Although routine histologic sections were unremarkable, LCs visualized using anti-CD1a staining of specimens from the site of immunization demonstrated greatly enlarged cell bodies but otherwise normal numbers of cells when compared to the control biopsies from the opposite arm, both at 24 and 48 hours (FIG. 1 C,D,E,F). Similar findings were seen using anti-HLA-DR and anti-S-100 to visualize LCs (not shown). LC morphology in the TCI immunized skin was similar in appearance to tonsilar crypt LCs that are thought to be chronically activated by lipopolysaccharides from the flora of the mouth (Noble).

Figure 2A:
FIGS. 2a-d are photographs showing normal Langerhans cell (A,B, 200 and 400×) and Langerhan cell activation by Cholera Toxin in mouse skin (C,D. 200×, 400×).
Figure 2B:
Figure 2C:
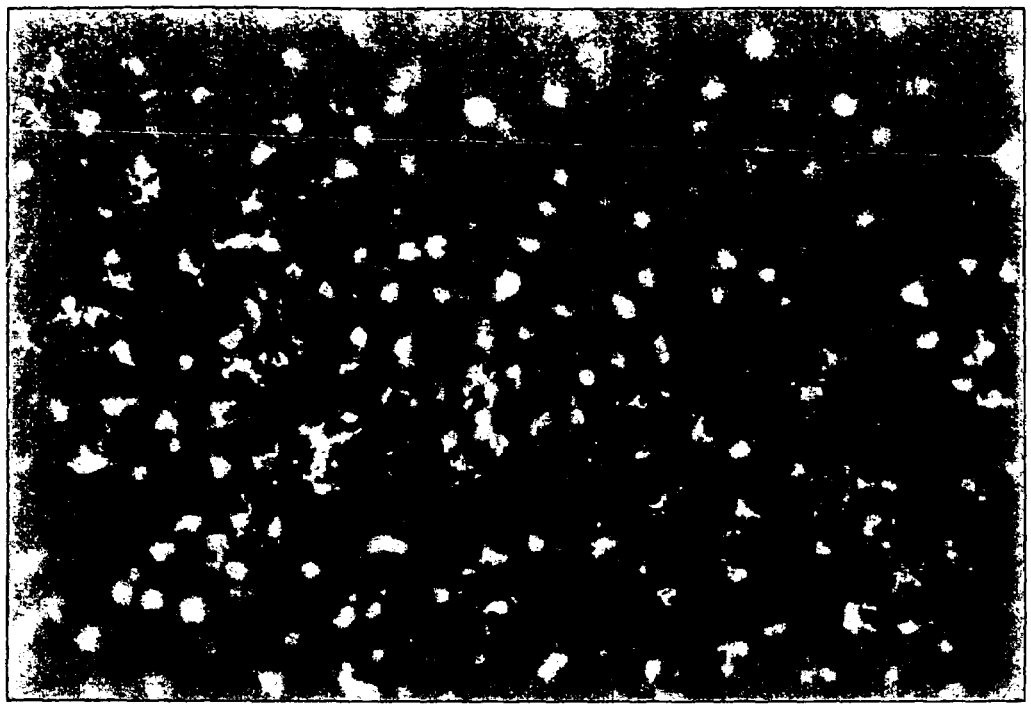
Figure 2D:

Because of the limited size and number of human skin biopsy specimens examined, complementary murine studies were performed. LC activation in murine systems using contact sensitizers, LPS, and proinflammatory cytokines is characterized by both changes in morphology (Aiba) and through elevations in surface marker expression (Jakob and Udey). Mouse ear skin is frequently used for studies of LC activation and has also been shown to be an excellent site for transcutaneous immunization (Scharton-Kersten). Epidermal sheets were prepared 24 hours after application of CT to the ear and stained for MHC class II, an LC-restricted marker in murine skin. In comparison to the PBS treated ears, FIG. 2A, LC in CT treated ears exhibited marked changes in LC morphology with loss of dendritic processes, enlarged cell bodies, and intense staining of the cells—features of LC activation (Aiba) (FIG. 2 B,C). The LC-activating potential of CT was confirmed using flow cytometry. LC from CT-treated skin expressed increased levels of MHC Class II antigens and CD 86 (B7-2) and decreased levels of E-cadherin, consistent with LC activation described elsewhere (Pierre, Aiba, Jakob).

Immunization Procedure which May be Used for Example 22.

BALB/c mice may be shaved with a #40 clipper. This shaving could be done without any signs of trauma to the skin. The shaving could be done from the mid-thorax to just below the nape of the neck. The mice can then be allowed to rest for 24 hours. Prior to this the mice could be ear-tagged for identification, and pre-bled to obtain a sample of pre-immune serum. Mice could also be transcutaneously immunized without shaving by applying 5-500 µl of immunizing solution to each ear. The mice could be immunized in the following way. Mice could be anesthetized with 0.03-0.06 ml of a 20 mg/ml solution of xylazine and 0.5 ml of 100 mg/ml ketamine and immobilized by this dose of anesthesia for approximately 1-3 hours. The mice could be placed ventral side down on a warming blanket.

The immunizing solution and penetration enhancement compound (or technique) could be placed on the dorsal shaved skin of a mouse in the following manner: a 1.2 cm×1.6 cm stencil made of polystyrene is laid gently on the back and a saline-wetted sterile gauze could be used to partially wet the skin (allowing even application of the immunizing solution), the immunizing solution could then be applied with a pipet to the area circumscribed by the stencil to yield a 2 cm$^2$ patch of immunizing solution. Care could be used not to scrape or rub the skin with the pipet tip. The immunizing solution could be spread around the area to be covered with the smooth side of the pipet tip. Alternatively, the immunizing solution could be place directly on the skin without wetting or with wetting without the use of a stencil.

The immunizing solution (between about 5 µl and about 200 µl) could be left on the back of the mouse for 60-120 minutes. At the end of the immunization period, the mouse could be held gently by the nape of the neck and the tail under a copious stream of lukewarm tap water, and washed for 10 seconds. The mouse could then be gently patted dry with a piece of sterile gauze and a second washing could then be performed for 10 seconds; the mouse could then be patted dry a second time and left in the cage. The mice would appear to exhibit no adverse effects from the anesthesia, immunization, washing procedure, or toxicity from the exotoxins. No skin irritation, swelling or redness would be seen after the immunization and the mice would appear to thrive. Immunization using the ear could be performed as described above except that fur would not be removed prior to immunization.

Antigen

The following antigens could be used for immunization and ELISA, and could be mixed using sterile PBS or normal saline. Cholera toxin or CT (List Biologicals, Cat #101B, lot #10149CB), CT B subunit (List Biologicals, Cat #BTO1, lot

CVXG-14E), CT A subunit (List Biologicals, Cat #102A, lot #CVXA-17B), CT A subunit (Calbiochem, Cat #608562); pertussis toxin, salt-free (List Biologicals, lot #181120a); tetanus toxoid (List Biologicals, lots #1913a and #1915a); *Pseudomonas* exotoxin A (List Biologicals, lot #ETA25a); diphtheria toxoid (List Biologicals, lot #15151); heat-labile enterotoxin from *E. coli* (Sigma, lot #9640625); bovine serum albumin or BSA (Sigma, Cat #3A-4503, lot #31F-0116); and *Hemophilus influenza* B conjugate (Connaught, lot#6J81401).

ELISA—IgG(H+L)

Antibodies specific for CT, LT, ETA, pertussis toxin, diphtheria toxoid, tetanus toxoid, *Hemophilus influenza* B conjugate, and BSA could be determined using ELISA in a technique similar to Glenn et al. (1995).

Example 22

Activation of LT may be performed by incubating the LT with trypsin (or trypsin immobilized on beads) with or without reducing agents (e.g., dithiotheritol) to break the disulphide bonds near the trypsin cleavage site, under standard reaction conditions. Native LT can be activated by incubation of 100 μg of protein with 0.1 μg trypsin in a total reaction volume of 100 μl for 45 min at 37° C. Alternatively, the trypsin can be fixed to beads and the LT may be eluted over the trypsin beads. Trypsin cleavage can be demonstrated by SDS-PAGE (Laemilli, U.K., 1970, Cleavage of structural proteins during the assembly of the head of bacteriophage T4, Nature 227:680-685). LT either treated or not treated with trypsin can be mixed with buffer containing dithiothreitol, and heated to 100° C. for 5 min prior to SDS-PAGE analysis. Trypsin-treated LT could have a proteolytic fragment of 21K daltons consistent with trypsin cleavage of the A1 and A2, allowing the A1 subunit to ADP-ribosylate G proteins and therefore exert its toxic effects whereas untreated LT would demonstrate a band at 28K daltons, consistent with an intact A subunit. Activation can further be demonstrated in the mouse Y-1 cell assay in which native LT would be 1,000 fold less active than CT, but trypsin-treated LT would be equally as active as CT. Activation can also be demonstrated using an enzymatic assay, the NAD:agmatine ADP-ribosyltransferase assay. In such an assay, non-trypsin-treated LT would be expected to show low or undetectable activity whereas trypsin-treated LT would be expected to show similar activity as that demonstrated by CT.

Example 23

Transcutaneous immunization may be more useful if the immunization can be performed over a short period of time. It may be useful for example for an immunization to be performed during a routine clinic visit lasting 30 minutes. In this example we show that transcutaneous immunization can be performed in hydrated, alcohol swabbed skin in such a short period.

C57BL/6 mice 6 to 8 weeks of age were anesthetized and shaved as described in the "immunization procedure". On the day of immunization the backs of the mice were wiped with isopropanol. After the alcohol had evaporated (approximately 10 minutes), 200 μl of water was applied to the back for hydration. 15 minutes later the immunization solution was applied to the back and left for the specified period of time. Removal of excess antigen was conducted as described in the "immunization procedure." Mice were immunized with CT alone (100 μg in 50 μl) at d0 and with CT plus DT (100 μg each in 100 VI volume) at 4, 6 and 9 weeks. Twelve weeks after the primary immunization the animals were bled and the anti-DT titers determined using an ELISA as described above for "ELISA IgG (H+L)". The results are shown in Table 23.

Anti-DT titers were clearly elevated in serum from all of the animals immunized with CT and DT when compared with titers in serum from the same animals prior to immunization (prebleed). Maximal effects of immunization appeared to occur in animals vaccinated for a period of 60 minutes although the titers were similar at 30 and 120 minutes. Fifteen minutes of immunization seemed less efficient as the titers in this group were approximately 10 fold less than that observed in the 30, 60 and 120 minute groups. Thus it appears that TCI can be achieved within 15 minutes of antigen application.

TABLE 23

Effect of the duration of antigen application on humoral immunity induced by transcutaneous immunization.

| ear tag # | duration of immunization | anti-DT IgG (ELISA units) | | |
|---|---|---|---|---|
| | | prebleed | 12 weeks | geomean |
| 361 | 15 min | 6 | 214 | 300 |
| 362 | 15 min | | 664 | |
| 363 | 15 min | | 314 | |
| 364 | 15 min | | 181 | |
| 365 | 15 min | | 1594 | |
| 366 | 30 min | 8 | 11953 | 13445 |
| 367 | 30 min | | 32478 | |
| 368 | 30 min | | 24346 | |
| 369 | 30 min | | 3457 | |
| 370 | 30 min | | 99776 | |
| 371 | 60 min | 12 | 75787 | 107963 |
| 372 | 60 min | | 200768 | |
| 373 | 60 min | | 102592 | |
| 374 | 60 min | | 87034 | |
| 375 | 60 min | | 9210 | |
| 376 | 120 min | 4 | 48132 | 48202 |
| 377 | 120 min | | 99362 | |
| 378 | 120 min | | 37308 | |
| 379 | 120 min | | 30255 | |
| 380 | 120 min | | 25149 | |

All publications referred to in this application are incorporated by reference herein as indicative of the state of the art.

REFERENCES

Alving, C. R., and Wassef, N. M. (1994) Cytotoxic T lymphocytes induced by liposomal antigens: Mechanisms of immunological presentation. AIDS Res. Hum. Retro., 10(sup. 2):S91-S94.

Antel, J. P., et al. (1996) Immunotherapy for multiple sclerosis: From theory to practice. Nature Medicine, 2:1074-1075.

Ausubel, F. M., et al. (1996) Current Protocols in Molecular Biology, Wiley, New York.

Bathurst, I. C., et al. (1993) An experimental vaccine cocktail for *Plasmodium falciparum* malaria. Vaccine, 11:449-456.

Blum, H. E. (1995) Variants of hepatitis B, C and D viruses: Molecular biology and clinical significance. Digestion, 56:85-95.

Bodanszky, M. (1993) Peptide Chemistry, Springer-Verlag, New York.

Bos, J. D. (1997) The skin as an organ of immunity. Clin. Exp. Immunol., 107 (suppl. 1):3-5.

Burnette, W. N., et al. (1994) Recombinant microbial ADP-ribosylating toxins of Bordetella pertussis, Vibrio cholerae, and enterotoxigenic Escherichia coli: Structure, function, and toxoid vaccine Development. In: Bioprocess Technology, (Eds. Burnette, W. N., et al.), pp. 185-203.

Chang, S. P., et al., (1989) Generalized immunological recognition of the major merozoite surface antigen (gp 195) of Plasmodium falciparum. Proc. Natl. Acad. Sci. USA, 86:6343-6347.

Chang, S. P., et al. (1992) A carboxyl-terminal fragment of Plasmodium falciparum gp 195 expressed by a recombinant baculovirus induces antibodies that completely inhibit parasite growth. J. Immunol., 139:548-555.

Chang, S. P., et al. (1994) Regulation of antibody specificity to Plasmodium falciparum merozoite surface protein-1 by adjuvant and MHC haplotype. J. Immunol., 152:3483-3490.

Clements, J. D., and Finkelstein, R. A. (1979) Isolation and characterization of homogenous heat-labile enterotoxins with high specific activity from Escherichia coli cultures. Infect. Immunol., 24:760-769.

Craig, J. (1965) The effect of cholera stool and culture filtrates on the skin guinea pigs and rabbits, In: Proceedings of the Cholera Research Symposium, Honolulu, US Public Health Service Publication No 1328, pp. 153-158.

Craig, J. (1972) Cutaneoous Responses to Cholera Skin Toxin in Man. I. Responses in Unimmunized American Males, In: The Journal of Infectious Diseases, Vol. 125, No. 3, pp. 203-215.

Dahl, M. V. (1996) Atopic dermatitis. In: Clinical Immunodermatology, 3rd Ed. Mosby, St. Louis, pp. 345-352.

Delenda, C., et al. (1994) Analysis of C-terminally truncated dengue 2 and dengue 3 virus envelope glycoproteins: Processing in insect cells and immunogenic properties in mice. J. Gen. Virol., 75:1569-1578.

Deprez, B., et al. (1996) Comparative efficiencies of simple lipopeptide constructs for in vivo induction of virus-specific CTL. Vaccine, 14:375-382.

Deutscher, M. P. (1990) Guide to Protein Purification, Academic Press, San Diego.

Dickenson, B. L., and Clements, J. D. (1995) Dissociation of Escherichia coli heat-labile entertoxin adjuvanticity from ADP-ribosyltransferase activity. Infect. Immun., 63:1617-1623.

Dragunsky, E. M., et al. (1992) Experimental evaluation of antitoxic protective effect of new cholera vaccines in mice. Vaccine, 10:735-736.

Elson, C. O., and Dertzbaugh, M. T. (1994) Mucosal adjuvants. In: Handbook of Mucosal Immunology (Eds. Ogra, P. L., et al.) Academic Press, San Diego, p. 391.

Finkelstein, R. A., and LoSpallutto, J. J. (1969) Pathogenesis of experimental cholera: Preparation and isolation of choleragen and choleragenoid, J. Exp. Med. 130:185-202.

Fonseca, B. A., et al. (1994) Recombinant vaccinia viruses co-expressing dengue-1 glycoproteins prM and E induce neutralizing antibodies in mice. Vaccine, 12:279-285.

Frankenburg, S., et al. (1996) Effective immunization of mice against cutaneous leishmaniasis using an intrinsically adjuvated synthetic lipopeptide vaccine. Vaccine, 14:923-929.

Fries, L. F., et al. (1992a) Liposomal malaria vaccine in humans: A safe and potent adjuvant strategy. Proc. Natl. Acad. Sci. USA, 89:358-362.

Fries, L. F., et al. (1992b) Safety, immunogenicity, and efficacy of a Plasmodium falciparum vaccine comprising a circumsporozoite protein repeat region peptide conjugated to Pseudomonas aeruginosa toxin A. Infect. Immun., 60:1834-1839.

Glenn, G. M., et al. (1995) Murine IgG subclass antibodies to antigens incorporated in liposomes containing lipid A. Immunol. Lett., 47:73-78.

Glenn, G. M., Scharton-Kersten, T., Vassell, R. Mallet, C. P., Hale, T. L. & Alving, C. R. Transcutaneous immunization with cholera toxin protects mice against lethal mucosal toxin challenge. J. Immunol. 161, 3211-3214 (1998).

Glenn, G. M., Rao, M., Matyas G. R. & Alving, C. R. Skin immunization made possible by cholera toxin. Nature 391, 851 (1998).

Glenn, G. M., Scharton-Kersten, T., Vassell, R., Matyas, G. & Alving. C. R. Transcutaneous immunization using bacterial ADP-ribosylating exotoxins as antigens and adjuvants. Infect. Immun. (in the press).

Goeddel, D. V. (1990) Gene Expression Technology, Academic Press, San Diego.

Gordon, Ada and Alistar Ramsey (1997) Vaccine, Vaccination and the Immune Response, Philadelphia, New York: Lipincott-Raven, pp. 13-14.

Gregoriadis, G. (1993) Liposome Preparation and Related Techniques, 2nd Ed., CRC Press, Boca Raton.

Herrington, D. A., et al. (1991) Safety and immunogenicity of a recombinant sporozoite malaria vaccine against Plasmodium vivax. Am. J. Trop. Med. Hyg., 45:695-701.

Hollingsbee, D. (1995) Use of hydrocolloid patches, In: Percutaneous Penetration Enhancers (Eds., Smith, E. and Maibach, H.), CRC Press.

Idson, B. (1978) Hydration and percutaneous absorption. Curr. Prob. Dermatol., 7:132-141.

Jahrling, P. B., et al. (1996) Passive immunization of Ebola virus-infected cynomolgus monkeys with immunoglobulin from hyperimmune horses. Arch. Virol. Suppl., 11:135-140.

Janeway, C. A., and Travers, P. (1996). Immunobiology, Churchill Livingstone, New York.

Janson, J.-C., and Ryden, L. (1989) Protein Purification, VCH, New York.

Katkov, W. N. (1996) Hepatitis vaccines. Med. Clin. North Am., 80:189-200.

Khusmith, S., et al. (1991) Protection against malaria by vaccination with sporozoite surface protein 2 plus CS protein. Science, 252:715-718.

Kounnas, M. Z., et al. (1992) The ($\alpha$2-macroglobulin receptor/low density lipoprotein receptor-related protein binds and internalizes Pseudomonas exotoxin A. J. Biol. Chem., 267:12420-12423.

Kriegler, M. (1990) Gene Transfer and Expression, Stockton Press, New York.

Krueger, K. M., and Barbieri, J. T. (1995) The family of bacterial ADP-ribosylating exotoxins. Clin. Microbiol. Rev., 8:34-47.

Lee, A., and Chen, M. (1994) Successful immunization against gastric infection with Helicobacter species: Use of a cholera toxin B-subunit-whole-cell vaccine. Infect. Immun., 62:3594-3597.

Leung, D. Y. (1997) Atopic dermatitis: Immunobiology and treatment with immune modulators. Clin. Exp. Immunol., 107 (Suppl. 1):25-30.

Lieberman, J. M., and Greenberg, D. P. (1996) Hepatitis A and B vaccines in children. Adv. Pediatr. Infect. Dis., 11:333-363.

Malik, A., et al. (1991) Human cytotoxic T lymphocytes against the *Plasmodium falciparum* circumsporozoite protein. Proc. Natl. Acad. Sci. USA, 88:3360-3304.

Mast, E. E., and Krawczynski, K. (1996) Hepatitis E: An overview. Annu. Rev. Med., 47:257-266.

Mckenzie, A. W., and Stoughton, R. B. (1962) Method for comparing percutaneous absorption of corticosteroids. Arch. Dermatol., 86:608-610.

Medzhitov, R., and Janeway, C. A. (1997) Innate immunity: Impact on the adaptive immune response. Curr. Opin. Immunol., 9:4-9.

Mekalanos, J. J., et al. (1979) Enzymatic activity of cholera toxin II. Relationships to proteolytic processing, disulphide bond reduction, and subunit composition, J. Biol. Chem., 254:5855-5861.

Migliorini, P., et al. (1993) Malaria vaccine: Immunization of mice with a synthetic T cell helper epitope alone leads to protective immunity. Eur. J. Immunol., 23:582-585.

Morein, B., and Simons, K. (1985) Subunit vaccines against enveloped viruses: Virosomes, micelles and other protein complexes. Vaccine, 3:83-93.

Munoz, E., et al. (1990) Cholera toxin discriminates between T helper 1 and 2 cells in receptor-mediated activation: Role of cAMP in T cell proliferation. J. Exp. Med., 172:95-103.

Murray, E. J. (1991) Gene Transfer and Expression Protocols. Humana Press, Clifton, N.J.

Nohria, A., and Rubin, R. H. (1994) Cytokines as potential vaccine adjuvants. Biotherapy, 7:261-269.

Paul, A., and Cevc, G. (1995) Noninvasive administration of protein antigens: Transdermal immunization with bovine serum albumin in transfersomes. Vaccine Res., 3:145-164.

Paul, A., et al. (1995) Transdermal immunization with large proteins by means of ultradeformable drug carriers. Eur. J. Immunol., 25:3521-3524, 1995.

Paul, W. E., and Seder, R. A. (1994) Lymphocyte responses and cytokines. Cell, 76:241-251.

Pessi, A., et al. (1991) Lack of H-2 restriction of the *Plasmodium falciparum* (NANP) sequence as multiple antigen peptide, Eur. J. Immunol., 24:2273-2276.

Pierce, N. F. (1978) The role of antigen form and function in the primary and secondary intestinal immune responses to cholera toxin and toxoid in rats. J. Exp. Med., 148:195-206.

Pierce, N. F., and Reynolds, H. Y. (1974) Immunity to experimental cholera. I. Protective effect of humoral IgG antitoxin demonstrated by passive immunization. J. Immunol., 113:1017-1023.

Plotkin, S. A., and Mortimer Jr., E. A. (1994) Vaccines, 2nd Ed., W.B. Saunders, Philadelphia.

Proksch, E., and Brasch, J. (1996) Integrity of the permeability barrier regulates epidermal Langerhans cell density. Br. J. Dermatol., 134:630-638.

Proksch, E., and Brasch, J. (1997) Influence of epidermal permeability barrier disruption and Langerhans' cell density on allergic contact dermatitis. Acta Derm. Venereol., 77:102-104.

Rappuoli, R., et al. (1995) Genetic detoxification of bacterial toxins: A new approach to vaccine development. Int. Archiv. Allergy Immunol., 108:327-333.

Rappuoli, R., et al. (1996) New vaccines against bacterial toxins. Adv. Exp. Med. Biol., 397:55-60.

Ribi, H. O., et al. (1988) Three-dimensional structure of cholera toxin penetrating a lipid membrane. Science, 239:1272-1276.

Richards, R. L., et al. (1995) A compendium of vaccine adjuvants and excipients. In: Vaccine Design (Eds., Powell, M. F., and Newman, M. J.), Plenum, New York.

Roberts, M. S., and Walker, M. (1993) Water, the most natural penetration enhancer. In: Pharmaceutical Skin Penetration Enhancement (Eds., Walters, K. A., and Hadgraft, J.), Marcel Dekker, New York.

Saloga, J., et al. (1996) Superantigens. Exp. Dermatol., 5:65-71.

Saukkonen, K., et al. (1992) Pertussis toxin has eukaryotic-like carbohydrate recognition domains. Proc. Natl. Acad. Sci. USA, 89:118-122.

Schneerson, R. E., et al. (1996) A toxoid vaccine for pertussis as well as diphtheria? Lessons to be relearned. Lancet 348:1289-1292.

Scopes, R. K. (1993) Protein Purification, Springer-Verlag, New York.

Seder, R. A., and Paul, W. E. (1994) Acquisition of lymphokine-producing phenotype by CD4+ T cells. Annu. Rev. Immunol., 12:635-673.

Shafara, A., et al. (1995) Hepatitis C. Ann. Intern. Med., 125:658-668.

Skeiky, Y. A. W., et al. (1995) A recombinant *Leishmania* antigen that stimulates human peripheral blood mononuclear cells to express a Th1-type cytokine profile and to produce interleukin 12. J. Exp. Med., 181:1527-1537.

Smedile, A., et al. (1994) Advances in hepatitis D virus biology and disease. Prog. Liver Dis., 12:157-175.

Smucny, J. J., et al. (1995) Murine immunoglobulin G subclass responses following immunization with live dengue virus or a recombinant dengue envelope protein. Am. J. Trop. Med. Hyg., 53:432-437.

Sniderman, D. P. (1995) The mucosal adjuvant activites of ADP-ribosylating bacterial enterotoxins. Crit. Rev. Immunol., 15:317-348.

Spangler, B. D. (1992) Structure and function of cholera toxin and the related *Escherichia coli* heat-labile enterotoxin. Microbiol. Rev., 56:622-647.

Stacey, K. J., et al. (1996) Macrophages ingest and are activated by bacterial DNA. J. Immunol., 157:2116-2122.

Stingl, G., et al. (1989) The immune functions of epidermal cells. Immunol. Ser., 46:3-42.

Streilein, J. W., and Grammer, S. F. (1989) In vitro evidence that Langerhans cells can adopt two functionally distinct forms capable of antigen presentation to T lymphocytes. J. Immunol., 143:3925-3933.

Summers, M. D., and Smith, G. E. (1987) A manual of methods for baculovirus vectors and insect cell culture procedure. Texas Agricultural Experiment Station Bulletin, No. 1555.

Tam, J. P. (1988) Synthetic peptide vaccine design: Synthesis and properties of a high-density multiple antigenic peptide system. Proc. Natl. Acad. Sci. USA, 85:5409-5413.

Tang, D. C., et al. (1997) Vaccination onto bare skin. Nature, 388:729-730.

Tew, J. G., et al. (1997) Follicular dendritic cells and presentation of antigen and costimulatory signals to B cells. Immunol. Rev., 156:39-52.

Trach, D. D., et al. (1997) Field trial of a locally produced, killed, oral cholera vaccine in Vietnam. Lancet, 349:231-235.

Udey, M. C. (1997) Cadherins and Langerhans cell immunobiology. Clin. Exp. Immunol., 107 (Suppl. 1):6-8.

van Heyningen, W. E., and Seal, J. R. (1983) Cholera: The American Scientific Experience, 1947-1980, Westview Press, Boulder, Colo.

Vandenbark, A. A., et al. (1996) Treatment of multiple sclerosis with T-cell receptor peptides: Results of a double-blind pilot trial. Nature Medicine, 2:1109-1115.

Vreden, S. G. S., et al. (1991) Phase I clinical trial of a recombinant malaria vaccine consisting of the circumsporozoite repeat region of *Plasmodium falciparum* coupled to hepatitis B surface antigen, Am. J. Trop. Med. Hyg., 45:533-538.

Wang, R., et al. (1995) Induction of protective polyclonal antibodies by immunization with a *Plasmodium yoelii* circumsporozoite protein multiple antigen peptide vaccine. J. Immunol., 154:2784-2793.

White, K., et al. (1993) Induction of cytolytic and antibody responses using *Plasmodium falciparum* repeatless circumsporozoite protein encapsulated in liposomes. Vaccine, 11: 1341-1346.

Wiesmueller, K.-H., et al. (1991) The antibody response in BALB/c mice to the *Plasmodium falciparum* circumsporozoite repetitive epitope covalently coupled to synthetic lipopeptide adjuvant. Immunology, 72:109-113.

Wisdom, G. B. (1994) Peptide Antigens, IRL Press, Oxford.

Zhang, T., et al. (1995) Oral immunization with the dodecapeptide repeat of the serine-rich *Entamoeba histolytica* protein (SREHP) fused to the cholera toxin B subunit induces a mucosal and systemic anti-SREHP antibody response. Infect. Immun., 63:1349-1355.

What we claim is:

1. A method for inducing an antigen-specific immune response in a subject comprising:
   a) pretreating an area of the skin of the subject, wherein pretreating comprises applying means for enhancing penetration and/or barrier disruption of the skin; and
   b) applying a formulation transcutaneously to the pretreated area to induce an antigen-specific immune response, wherein the formulation comprises:
      1) an antigen in an amount effective to induce an antigen-specific immune response;
      2) an adjuvant present in an amount effective to enhance the immune response to the antigen; and,
      3) a pharmaceutically acceptable carrier;
   wherein pretreating enhances the immune response.

2. The method of claim 1, wherein pretreating comprises applying to the skin a chemical means, a physical means, a mechanical means, a hydration means, or a combination thereof.

3. The method of claim 1, wherein pretreating comprises applying a chemical to the skin.

4. The method of claim 3, wherein the chemical is an alcohol, an acetone, a detergent, a depilatory agent, a keratinolytic formulation, a cream, or a combination thereof.

5. The method of claim 1, wherein pretreating comprises applying a device.

6. The method of claim 5, wherein the device is selected from the group consisting of a propellant device, a device comprising tines, a device comprising microneedles, a device comprising a tine disk, a tape stripping device, a gas powered gun, a swab, an emery board, an abrasive pad, an electroporation device, an ultrasound device, and an iontophoresis device.

7. The method of claim 1, wherein the antigen is a nucleic acid encoding an antigen, carbohydrate, a glycolipid, a glycoprotein, a lipid, a lipoprotein, phospholipid, a polypeptide, a protein, a fusion protein, or chemical conjugate of a combination thereof.

8. The method of claim 1, wherein the antigen is derived from a pathogen.

9. The method of claim 8, wherein the pathogen is a virus, a bacterium, a parasite, or a fungus.

10. The method of claim 9, wherein the virus is an influenza virus or a rabies virus.

11. The method of claim 10, wherein the antigen is hemagglutinin A.

12. The method of claim 9, wherein the bacterium is *E. coli* or *Bacillus anthracis*.

13. The method of claim 12, wherein the antigen is *E. coli* heat-labile enterotoxin (LT).

14. The method of claim 12, wherein the antigen is a nucleic acid encoding E. coli heat-labile enterotoxin (LT).

15. The method of claim 1, wherein the antigen is a pathogen.

16. The method of claim 15, wherein the pathogen is a virus, a bacterium, a parasite, or a fungus.

17. The method of claim 16, wherein the virus is a whole virus, a live virus, an attenuated live virus, an inactivated virus, a detergent treated virus, or a combination thereof.

18. The method of claim 17, wherein the virus is an influenza virus or a rabies virus.

19. The method of claim 18, wherein the influenza virus comprises hemagglutinin A.

20. The method of claim 16, wherein the bacterium is E coli or Bacillus anthracis.

21. The method of claim 20, wherein the E. coli comprises E. coli heat-labile enterotoxin (LT).

22. The method of claim 1, wherein the antigen is a multivalent antigen.

23. The method of claim 1, wherein the adjuvant comprises a molecule selected from the group consisting of a bacterial ADP-ribosylating exotoxin (bARE), a binding B subunit of a bARE, a toxoid of a bARE, a genetically altered bARE, and a genetically detoxified mutant of a bARE.

24. The method of claim 23, wherein the antigen is an influenza antigen.

25. The method of claim 1, wherein the adjuvant is a nucleic acid encoding a molecule selected from the group consisting of a bacterial ADP-ribosylating exotoxin (bARE), a binding B subunit of a bARE, a toxoid of a bARE, a genetically altered bARE, and a genetically detoxified mutant of a bARE.

26. The method of claim 25, wherein the nucleic acid encodes E. coli heat labile enterotoxin (LT).

27. The method of claim 1, wherein the antigen and the adjuvant are the same molecule.

28. The method of claim 27, wherein the molecule is E. coli heat-labile enterotoxin (LT).

29. The method of claim 27, wherein the molecule is hemagglutinin A.

30. The method of 1, wherein the formulation is applied using a patch.

31. The method of claim 1, wherein the adjuvant is selected from the group consisting of nucleic acid encoding an adjuvant, bacterial exotoxin, cytokine, chemokine, lipopolysaccharide, a molecule containing unmethylated CpG motifs, a heat shock protein, a derivative of a heat shock protein, tumor necrosis factor, genetically detoxified toxin, and combinations thereof.

32. The method of claim 1, wherein the adjuvant is provided as a nucleic acid comprising a sequence encoding the adjuvant.

33. The method of claim 1, wherein the antigen or adjuvant activates an antigen presenting cell.

34. The method of claim 33, wherein the antigen presenting cell is a Langerhans cell or a dermal dendritic cell.

35. The method of claim 1, wherein the antigen is a whole microorganism, a whole cell, or a virion.

36. A method for inducing an antigen-specific immune response in a subject comprising concurrently,
    a) treating an area of the skin of the subject, wherein treating comprises applying means for enhancing penetration and/or barrier disruption of the skin; and
    b) applying a formulation transcutaneously to the treated area to induce an antigen-specific immune response, wherein the formulation comprises:
        1) an antigen in an amount effective to induce an antigen-specific immune response;
        2) an adjuvant present in an amount effective to enhance the immune response to the antigen; and,
        3) a pharmaceutically acceptable carrier;
    wherein treating enhances the immune response.

37. The method of claim 36, wherein treating comprises applying to the skin a chemical means, a physical means, a mechanical means, a hydration means, or a combination thereof.

38. The method of claim 36, wherein treating comprises applying a chemical to the skin.

39. The method of claim 38, wherein the chemical is an alcohol, an acetone, a detergent, a depilatory agent, a keratinolytic formulation, a cream, or a combination thereof.

40. The method of claim 36, wherein treating comprises applying a device.

41. The method of claim 40, wherein the device is selected from the group consisting of a propellant device, a device comprising tines, a device comprising microneedles, a device comprising a tine disk, a tape stripping device, a gas powered gun, a swab, an emery board, an abrasive pad, an electroporation device, an ultrasound device, and an iontophoresis device.

42. The method of claim 36, wherein the antigen is a nucleic acid encoding an antigen, carbohydrate, a glycolipid, a glycoprotein, a lipid, a lipoprotein, phospholipid, a polypeptide, a protein, a fusion protein, or chemical conjugate of a combination thereof.

43. The method of claim 36, wherein the antigen is derived from a pathogen.

44. The method of claim 43, wherein the pathogen is a virus, a bacterium, a parasite, or a fungus.

45. The method of claim 44, wherein the virus is an influenza virus or a rabies virus.

46. The method of claim 45, wherein the antigen is hemagglutinin A.

47. The method of claim 44, wherein the bacterium is E. coli or Bacillus anthracis.

48. The method of claim 47, wherein the antigen is E. coli heat-labile enterotoxin (LT).

49. The method of claim 47, wherein the antigen is a nucleic acid encoding E. coli heat-labile enterotoxin (LT).

50. The method of claim 34, wherein the antigen is a pathogen.

51. The method of claim 50, wherein the pathogen is a virus, a bacterium, a parasite, or a fungus.

52. The method of claim 51, wherein the virus is a whole virus, a live virus, an attenuated live virus, an inactivated virus, a detergent treated virus, or a combination thereof.

53. The method of claim 52, wherein the virus is an influenza virus or a rabies virus.

54. The method of claim 53, wherein the influenza virus comprises hemagglutinin A.

55. The method of claim 51, wherein the bacterium is E coli or Bacillus anthracis.

56. The method of claim 55, wherein the E. coli comprises E. coli heat-labile enterotoxin (LT).

57. The method of claim 34, wherein the antigen is a multivalent antigen.

58. The method of claim 34, wherein the adjuvant comprises a molecule selected from the group consisting of a bacterial ADP-ribosylating exotoxin (bARE), a binding B subunit of a bARE, a toxoid of a bARE, a genetically altered bARE, and a genetically detoxified mutant of a bARE.

59. The method of claim 58, wherein the antigen is an influenza antigen.

60. The method of claim 34, wherein the adjuvant is a nucleic acid encoding a molecule selected from the group consisting of a bacterial ADP-ribosylating exotoxin (bARE), a binding B subunit of a bARE, a toxoid of a bARE, a genetically altered bARE, and a genetically detoxified mutant of a bARE.

61. The method of claim 60, wherein the nucleic acid encodes *E. coli* heat labile enterotoxin (LT).

62. The method of claim 36, wherein the antigen and the adjuvant are the same molecule.

63. The method of claim 62, wherein the molecule is *E. coli* heat-labile enterotoxin (LT).

64. The method of claim 62, wherien the molecule is hemagglutinin A.

65. The method of 36, wherein the formulation is applied using a patch.

66. The method of claim 36, wherein the adjuvant is selected from the group consisting of nucleic acid encoding an adjuvant, bacterial exotoxin, cytokine, chemokine, lipopolysaccharide, a molecule containing unmethylated CpG motifs, a heat shock protein, a derivative of a heat shock protein, tumor necrosis factor, genetically detoxified toxin, and combinations thereof.

67. The method of claim 36, wherein the adjuvant is provided as a nucleic acid comprising a sequence encoding the adjuvant.

68. The method of claim 36, wherein the antigen or adjuvant activates an antigen presenting cell.

69. The method of claim 68, wherein the antigen presenting cell is a Langerhans cell or a dermal dendritic cell.

70. The method of claim 36, wherein the antigen is a whole microorganism, a whole cell, or a virion.

71. A method for inducing an antigen-specific immune response in a subject comprising:
   a) delivering parenterally a first formulation comprising an antigen to a subject;
   b) treating an area of the skin of the subject, wherein treating comprises applying means for enhancing penetration and/or barrier disruption of the skin to enhance the immune response; and
   c) applying transcutaneously a second formulation comprising an adjuvant to the area of the skin, thereby inducing an antigen-specific immune response.

72. The method of claim 71, wherein treating comprises applying to the skin a chemical means, a physical means, a mechanical means, a hydration means, or a combination thereof.

73. The method of claim 71, wherein treating comprises applying a chemical to the area of the skin.

74. The method of claim 73, wherein the chemical is an acetone, a detergent, a depilatory agent, a keratinolytic formulation, or a combination thereof.

75. The method of claim 71, wherein treating comprises applying a device.

76. The method of claim 75, wherein the device is selected from the group consisting of a propellant device, a device comprising tines, a device comprising microneedles, a device comprising a tine disk, a tape stripping device, a gas powered gun, a swab, an emery board, an abrasive pad, an electroporation device, an ultrasound device, and an iontophoresis device.

77. The method of claim 71, wherein the antigen is a nucleic acid encoding an antigen, a carbohydrate, a glycolipid, a glycoprotein, a lipid, a lipoprotein, phospholipid, a polypeptide, a protein, a fusion protein, or chemical conjugate of a combination thereof.

78. The method of claim 71, wherein the antigen is derived from a pathogen.

79. The method of claim 78, wherein the pathogen is a virus, a bacterium, a parasite, or a fungus.

80. The method of claim 79, wherein the virus is an influenza virus or a rabies virus.

81. The method of claim 80, wherein the antigen is hemagglutinin A.

82. The method of claim 79, wherein the bacterium is *E. coli* or *Bacillus anthracis*.

83. The method of claim 82, wherein the antigen is *E. coli* heat-labile enterotoxin (LT).

84. The method of claim 81, wherein the antigen is a nucleic acid encoding *E. coli* heat-labile enterotoxin (LT).

85. The method of claim 71, wherein the antigen is a pathogen.

86. The method of claim 85, wherein the pathogen is a virus, a bacterium, a parasite, or a fungus.

87. The method of claim 86, wherein the virus is a whole virus, a live virus, an attenuated live virus, an inactivated virus, a detergent treated virus, or a combination thereof.

88. The method of claim 87, wherein the virus is an influenza virus or a rabies virus.

89. The method of claim 88, wherein the influenza virus comprises hemagglutinin A.

90. The method of claim 86, wherein the bacterium is *E coli* or *Bacillus anthracis*.

91. The method of claim 90, wherein the *E. coli* comprises *E. coli* heat-labile enterotoxin (LT).

92. The method of claim 71, wherein the antigen is a multivalent antigen.

93. The method of claim 71, wherein the adjuvant comprises a molecule selected from the group consisting of a bacterial ADP-ribosylating exotoxin (bARE), a binding B subunit of a bARE, a toxoid of a bARE, a genetically altered bARE, and a genetically detoxified mutant of a bARE.

94. The method of claim 93, wherein the antigen is an influenza antigen.

95. The method of claim 71, wherein the adjuvant is a nucleic acid encoding a molecule selected from the group consisting of a bacterial ADP-ribosylating exotoxin (bARE), a binding B subunit of a bARE, a toxoid of a bARE, a genetically altered bARE, and a genetically detoxified mutant of a bARE.

96. The method of claim 95, wherein the nucleic acid encodes *E. coli* heat labile enterotoxin (LT).

97. The method of claim 71, wherein the adjuvant is selected from the group consisting of nucleic acid encoding an adjuvant, bacterial exotoxin, cytokine, chemokine, lipopolysaccharide, a molecule containing umethylated CpG motifs, a heat shock protein, a derivative of a heat shock protein, tumor necrosis factor, genetically detoxified toxin, and combinations thereof.

98. The method of claim 71, wherein the adjuvant is provided as a nucleic acid comprising a sequence encoding the adjuvant.

99. The method of claim 71, wherein the antigen or adjuvant activates an antigen presenting cell.

100. The method of claim 99, wherein the antigen presenting cell is a Langerhans cell or a dermal dendritic cell.

101. The method of claim 71, wherein the antigen is a whole microorganism, a whole cell, or a virion.

102. The method of claim 71, wherein the first formulation is administered subcutaneously, intradermally, or intramuscularly.

103. The method of claim 71, wherein the second formulation is applied using a patch.

104. The method of claim 7, wherein the nucleic acid is a DNA encoding an influenza protein.

105. The method of claim 42, wherein the nucleic acid is a DNA encoding an influenza protein.

106. The method of claim 77, wherein the nucleic acid is a DNA encoding an influenza protein.

107. The method of claim 28, wherein the LT is a genetically altered toxin.

108. The method of claim 63, wherein the LT is a genetically altered toxin.

* * * * *

UNITED STATES PATENT AND TRADEMARK OFFICE
CERTIFICATE OF CORRECTION

PATENT NO. : 7,378,097 B2 Page 1 of 1
APPLICATION NO. : 10/790715
DATED : May 27, 2008
INVENTOR(S) : Gregory M. Glenn et al.

It is certified that error appears in the above-identified patent and that said Letters Patent is hereby corrected as shown below:

Column 56,   Claim 50, line 44, please delete "34" and insert therefore --36--;

Claim 57, line 59, please delete "34" and insert therefore --36--;

Claim 58, line 61, please delete "34" and insert therefore --36--; and

Column 57,   Claim 60, line 1, please delete "34" and insert therefore --36--.

Signed and Sealed this

Twenty-third Day of December, 2008

JON W. DUDAS
*Director of the United States Patent and Trademark Office*